(12) United States Patent
Filvaroff et al.

(10) Patent No.: US 7,268,112 B2
(45) Date of Patent: *Sep. 11, 2007

(54) USE OF INSULIN FOR THE TREATMENT OF CARTILAGINOUS DISORDERS

(75) Inventors: Ellen H. Filvaroff, San Francisco, CA (US); Franklin W. Okumu, Oakland, CA (US)

(73) Assignee: Genetech, Inc., S. San Francisco, CA (US)

(*) Notice: Subject to any disclaimer, the term of this patent is extended or adjusted under 35 U.S.C. 154(b) by 431 days.

This patent is subject to a terminal disclaimer.

(21) Appl. No.: 10/740,098

(22) Filed: Dec. 17, 2003

(65) Prior Publication Data

US 2004/0138101 A1     Jul. 15, 2004

Related U.S. Application Data

(63) Continuation of application No. 09/815,229, filed on Mar. 22, 2001, now Pat. No. 6,689,747.

(60) Provisional application No. 60/192,103, filed on Mar. 24, 2000.

(51) Int. Cl.
    *A61K 38/28*     (2006.01)

(52) U.S. Cl. .............................. 514/3; 514/4; 424/85.1

(58) Field of Classification Search ............. None
    See application file for complete search history.

(56) References Cited

U.S. PATENT DOCUMENTS

| | | | |
|---|---|---|---|
| 3,773,919 A | 11/1973 | Boswell et al. | |
| 4,430,266 A | 2/1984 | Frank | |
| 4,530,840 A | 7/1985 | Tice et al. | |
| 4,622,219 A | 11/1986 | Haynes | |
| 4,725,442 A | 2/1988 | Haynes | |
| 4,767,628 A | 8/1988 | Hutchinson | |
| 4,891,225 A | 1/1990 | Langer et al. | |
| 4,957,744 A | 9/1990 | della Valle et al. | |
| 5,019,400 A | 5/1991 | Gombotz et al. | |
| 5,444,047 A | 8/1995 | DiPasquale | |
| 5,506,302 A | 4/1996 | Shiono et al. | |
| 5,514,646 A | 5/1996 | Chance et al. | |
| 5,654,010 A | 8/1997 | Johnson et al. | |
| 5,656,722 A | 8/1997 | Dorschug | |
| 5,891,722 A | 4/1999 | Fuks et al. | |
| 6,689,747 B2 * | 2/2004 | Filvaroff et al. .......... | 514/3 |

FOREIGN PATENT DOCUMENTS

| | | |
|---|---|---|
| EP | 0 055 945 A2 | 7/1982 |
| EP | 0 324 274 A1 | 7/1989 |
| EP | 0 375 437 B1 | 6/1990 |
| EP | 0 427 296 A1 | 5/1991 |
| EP | 0 534 705 A2 | 9/1991 |
| EP | 0 195 691 B1 | 11/1991 |
| EP | 0 519 750 A2 | 12/1992 |
| EP | 0 171 147 B1 | 3/1993 |
| EP | 0 171 886 B1 | 3/1993 |
| EP | 0 171 887 B1 | 3/1993 |
| EP | 0 544 466 A1 | 6/1993 |
| EP | 0 557 976 B1 | 9/1993 |
| EP | 0 560 723 A1 | 9/1993 |
| EP | 0 214 826 B1 | 10/1994 |
| EP | 0 434 652 B1 | 11/1994 |
| EP | 0 436 469 B1 | 2/1995 |
| EP | 0 704 527 A2 | 4/1996 |
| WO | 86/01540 | 3/1986 |
| WO | 89/10937 | 11/1989 |
| WO | 91/19510 | 12/1991 |
| WO | 92/13565 | 8/1992 |
| WO | 94/04569 | 3/1994 |
| WO | 95/07931 | 3/1995 |
| WO | 95/22614 | 8/1995 |
| WO | 96/04307 | 2/1996 |
| WO | 96/07399 | 3/1996 |
| WO | 96/20724 | 7/1996 |
| WO | 96/40072 | 12/1996 |
| WO | 97/03692 | 2/1997 |
| WO | 97/35563 | 10/1997 |
| WO | 97/39032 | 10/1997 |
| WO | 98/45427 | 10/1998 |
| WO | 99/51262 | 10/1999 |

OTHER PUBLICATIONS

Amin and Abramson., "The Role of Nitric Oxide in Articular Cartilage Breakdown in Osteoarthritis." *Curr. Opin. Rheum.* 10(3):263-268 (1998).

Arend W. P. et al., "Interleukin-1 Receptor Antagonist: Role in Biology" *Ann. Rev. Immunol.* 16:27-55.

Athanasiou et al., "Effects of diabetes mellitus on the biomechanical properties of human ankle cartilage". *Clin. Orthop. Rel. Res.* 368:182-189 (1999).

(Continued)

*Primary Examiner*—Gary B. Nickol
*Assistant Examiner*—Dong Jiang
(74) *Attorney, Agent, or Firm*—Craig G. Svoboda

(57) ABSTRACT

The present invention relates to methods for the treatment and repair of cartilage, including cartilage damaged by injury or cartilaginous disorders, including arthritis, comprising the administration of insulin and/or insulin variants. Optionally, the administration may be in combination with a cartilage agent (e.g., peptide growth factor, catabolism antagonist, osteo-, synovial, anti-inflammatory factor), in an extended- or sustained-release form. Alternatively, the method provides for the treatment and repair of cartilage damaged by injury or cartilaginous disorders comprising the administration of insulin and/or insulin in combination with standard surgical techniques. Alternatively, the method provides for the treatment and repair of cartilage damaged by injury or cartilaginous disorders comprising the administration of chondrocytes previously treated with an effective amount of insulin and/or insulin variant.

43 Claims, 26 Drawing Sheets

OTHER PUBLICATIONS

Baker et al., "The structure of 2Zn pig insulin crystals at 1.5 . . . resolution" *Philos. Trans. Royal Soc. London. Ser. B. Biol. Sci.* 319(1195):369-456 (Jul. 6, 1988).

Balschmidt, P., "Prepn. of active (B28-Asp) -human insulin—using the lysyl specific endopeptides from Achromobacter lyticus to convert (B28-Asp) -human insulin precursor" *Research Disclosure* (RD 365030 (Acct. 94-308986)) pp. 487-488 (1994).

Baragi et al., "Transplantation of Adenovirally Transduced Allogenic Chondrocytes into Articular Cartilage Defects In Vivo." *Osteoarthritis and Cartilage.* 5(4):275-282 (1997).

Baragi et al., "Transplantation of Transduced Chondrocytes Protects Articular Cartilage from Interleukin 1-Induced Extracellular Matrix Degradation" *J. Clin. Invest.* 96(5):2454-2460 (Nov. 1995).

Bell et al., "Sequence of the human insulin gene" *Nature* 284:26-32 (Mar. 1980).

Bendele and Hulman, "Effects of body weight restriction on the development and progression of spontaneous osteoarthritis in guinea pigs" *Arthritis Rheum.* 34(9):1180-1184 (Sep. 1991).

Bendele and Hulman, "Spontaneous cartilage degeneration in guinea pigs" *Arthritis Rheum.* 31(4):561-565 (Apr. 1988).

Bentley et al., "Role of B13 Glu in Insulin Assembly: The Hexamer Structure of Recombinant Mutant (B13 Glu-Gln) Insulin" *J. Mole. Biol.* 228:1163-1176 (1992).

Berridge and Tan, "Characterization of the cellular reduction of 3-(4.5-dimethylthiazol-2-y)-2,5-diphenyltetrazolium bromide, etc." *Archives of Biochemistry & Biophysics* 303(2):474-482 (1993).

Bhakta et al., "The Insulin-like Growth Factors (IGFs) and I and II Bind to Articular Cartilage via the IGF-binding Proteins" *Journal of Biological Chemistry* 275(8):5860-5866 (Feb. 25, 2000).

Binder, C., "A Theoretical Model for the Absorption of Soluble Insulin" *Artifical Systems for Insulin Delivery*, P. Brunetti et al. Eds., New York:Serono Symposia Publs. from Raven Press vol. 6:53-57 (1983).

Blundell et al., "Insulin: The structure in the crystal and its reflection, etc." (Laboratory of Molecular Biophysics, South Parks Road, Oxform, England) pp. 279-402.

Brader et al., "Insulin hexamers: new conformations and applications" *TIBS* 16:341-345 (Sep. 1991).

Brange and Langkjaer, "Chemical stability of insulin. 3. Influence of excipients, formulation, and pH" *Acta Pharm. Nord.* 4(3):149-158 (1992).

Brange and Langkjaer, "Insulin formulation and delivery" *Protein Delivery: Physical Systems*, Sanders and Hendren, New York:Plenum Press, Chapter 13, pp. 343-410 (1997).

Brange et al., "Chemical Stability of Insulin. 1. Hydrolytic Degradation During Storage of Pharmaceutical Preparations" *Pharm. Res.* 9(6):715-726 (1992).

Brange et al., "Chemical Stability of Insulin. 2. Formulation of Higher Molecular Weight Transformation Products During Storage of Pharmaceutical Preparations" *Pharm. Res.* 9(6):727-734 (1992).

Brange et al., "Designing insulin for diabetes therapy by protein engineering" *Curr. Opin. Struct. Biol.* 1:934-940 (1991).

Brange et al., "Monomeric insulins and their experimental and clinical implications" *Diabetes Care* 13(9):923-954 (Sep. 1990).

Brems et al., "Improved insulin stability through amino acid substitution" *Protein Engineering* 5(6):519-525 (1992).

Buckwalter et al., "Restoration of Injured or Degenerated Articular Cartilage" *J. Am. Acad. Orthop. Surg.* 2(4):192-201 (1994).

Chance et al., "Chemical, physical, and biologic properties of biosynthetic human insulin" *Diabetes Care* 4(2):147-154 (1981).

Chen et al., "Chondrocyte Transplantation and Experimental Treatment Options for Articular Cartilage Defects" *Amer. J. Orthop.* 26(6):396-406 (1997).

Chevalier and Tyler, "Production of binding proteins and role of the insulin-like growth factor I binding protein 3 in human articular cartilage explants" *Brit. J. Rheum.* 35:515-522 (1996).

Chin et al., "Interactions Between Interleukin-1 and Basic Fibroblast Growth Factor on Articular Chondrocytes. Effects on Cell Growth, Prostanoid Production, and Receptor Modulation" *Arthritis Rheum.* 34(3):314-324 (Mar. 1991).

Cleland and Jones, "Stable formulation of recombinant human growth hormone and interferon-γ for Microencapsulation in biodegradable microspheres" *Pharm. Res.* 13(10):1464-1475 (1996).

Cleland, J.L., "Design and production of single-immunization vaccines using polyactide polyglycolide microsphere systems" *Vaccine Design: The Subunit and Adjuvant Approach*, M.F. Powell and M.J. Newman, New York:Plenum Press, Chapter 18, pp. 439-462 (1995).

Cohen and Foglia, "Effect of insulin in vitro on C-acetate and S-sulfate uptake into aortic mucopolysaccharides in normal and diabetic rats" *Proc. Soc. Exp. Biol. Med.* 135:113-115 (1970).

Cohen and Foglia, "Effect of pancreatectomy, hypophysectomy, and hypophysectomy-pancreatectomy on sulfate uptake in rat aortas" *Proc. Soc. Exp. Biol. Med.* 133:1275-1278 (1970).

Cohen and Foglia, "Sulfate uptake and incorporation into aortic mucopolysaccharides in experimental diabetes" *Proc. Soc. Exp. Biol. Med.* 132:376-378 (1969).

Coletti, Jr. et al., "A comparison of the physical behavior of normal articular cartilage and the arthroplasty surface" *J. Bone Joint Surg.* 54-A(1):147-160 (Jan. 1972).

Collett-Solberg and Cohen, "The Role of the Insulin-Like Growth Factor Binding Proteins and the IGFBP Proteases in Modulating IgF Action" *Endocrin. Metab. Clin. N. Amer.* 25(3):591-614 (Sep. 1996).

Coutts et al., "Cartilage repair using a porous polylactic acid matrix with allogeneic perichondrial cells" (40th Annual Meeting, Orthop. Res. Soc., Feb. 21-24, New Orleans, LA) pp. 240-241 (1994).

Coutts et al., "Effect of Growth Factors on Cartilage Repair" *Amer. Acad. Orthop. Surg.* (Instructional Course Lect.), Chapter 47, pp. 487-494 (1997).

Craig et al., "A chemically modified tetracycline inhibits streptozotcin-induced diabetic depression of skin collagen synthesis and steady-state type I procollagen mRNA" *Biochimica et Biophysica Acta* 1402:250-260 (1998).

Davidson, M.B., "Effect of growth hormone on carbohydrate and lipid metabolism" *Endocrine Rev.* 8(2):115-131 (May 1987).

Derewenda et al., "Phenol Stabilizes More Helix in a New Symmetrical Zinc Insulin Hexamer." *Nature.* 338:594-596 (Apr. 1989).

Desai et al., "Surface Modifications of Polymeric Biomaterials for Reduced Thrombogenicity" *Polym. Mater. Sci. Eng.* 62:731-735 (1991).

DiMarchi et al., "Synthesis of a fast-acting insulin based on structural homology with insulin-like growth factor I" *Proc. 12th Amer. Peptide Sympos.* (Lilly Res. Labs, Indianapolis, Indiana) pp. 26-28 (1992).

Dubaquie and Lowman, "Total Alanine-Scanning Mutagenesis of Insulin-Like Growth Factor I (IGF-I) Identifies Differential Binding Epitopes for IGFBP-1 and IGFBP-3" *Biochemistry* 38(20):6386-6396 (1999).

Evans and Robbins, "Getting Genes Into Human Synovium" *J. Rheumatol.* 24(11):2061-2063 (1997).

Evans et al., "Blocking Cytokines with Genes" *J. Leukocyte Biol.* 64:55-61 (Jul. 1998).

Farndale et al., "Improved quantitation and discrimination of sulphated glycosaminoglycans by use of dimethylmethylene blue" *Biochimica et Biophysica Acta* 883:173-177 (1986).

Fernihough et al., "Local disruption of the insulin-like growth factor system in the arthritic joint" *Arthritis Rheum.* 39(9):1556-1565 (1996).

Florini and Roberts, "Effect of Rat Age on Blood Levels of Somatomedin-like Growth Factors" *J. Gerontol.* 35(1):23-30 (1980).

Frank and Chance, "Two routes for producing human insulin utilizing recombinant DNA technology" *Munch. med. Wschr.* (Supp. 1) 125:S14-S20 (1983).

Frenkel and Di Cesare, "Degradation and Repair of Articular Cartilage" *Front. Biosci.* 4:d671-685 (Oct. 15, 1999).

Gey and Thalhimer, "Observation on the effects of insulin introduced into the medium of tissue cultures" *J. Amer. Med. Assoc.* 82(20):1609 (1924).

Goeddel et al., "Expression in *Escherichia coli* of chemically synthesized genes for human insulin" *Proc. Natl. Acad. Sci. USA* 76(1):106-110 (1979).

Green, Jr., "Articular Cartilage Repair: Bahavior of Rabbit Chondrocytes During Tissue Culture and Subsequent Allografting." *Clin. Orthop. Relat. Res.* (Sect. III, Basic Science and Pathology) 124:237-250 (May 1977).

Guerne et al., "Growth Factor Responsiveness of Human Articular Chondrocytes: Distinct Profiles in Primary Chondrocytes, Subcultured Chondrocytes, and Fibroblasts." *J. Cellular Physiology* 158(3):476-484 (1994).

Hadley, M., "Pancreatic hormones and metabolic regulation" *Endocrinology*, 2d edition, Englewood Cliffs, NJ:Prentice-Hall, Chapter 11, pp. 10-12, 237-265 (1988).

Hajek and Solursh, "Stimulation of Growth and Mucopolysaccaraide Synthesis by Insulin Treatment of Chick Embryo, etc." *Gen. Compar. Endocrin.* 25:432-446 (1975).

Hering, T.M., "Regulation of Chondrocyte Gene Expression." *Front. Biosci.* 4:d743-761 (Oct. 15, 1999).

Hill and Logan, "Peptide Growth Factors and their Interactions During Chondrogenesis" *Progress in Growth Factor Research* 4(1):45-68 (1992).

Hora et al., "Controlled Release of Interleukin-2 from Biodegradable Microspheres" *Bio/Technology* 8:755-758 (Aug. 1990).

Hunziker and Rosenberg, "Induction of Repair in Partial Thickness Articular Cartilage Lesions by Timed Release of TGFβ" (40th Annual Meeting, Orthop. Res. Soc., Feb. 21-24, New Orleans, LA) 19:236-241 (1994).

Ippolito et al., "Insulin stimulation therapy in collagen disease" *Reumatismo* (translation from Italian by RWS Group LLC, San Francisco, CA) XX(5):561-564 (1968).

Jimenez et al., "Spontaneous Osteoarthritis in Dunkin Hartley Guinea Pigs: Histologic, Radiologic, and Biochemical Changes" *Laboratory Animal Science*, Amer. Assn. for Lab. Animal Sci., Rockville, MD vol. 47(6):598-601 (Dec. 1997).

Johnson et al., "A month-long effect from a single injection of microencapsulated human growth hormone" *Nature Medicine* 2(7):795-799 (Jul. 1996).

Jones and Clemmons., "Insulin-Like Growth Factors and Their Binding Proteins: Biological Actions." *Endocrine Rev.* 16(1):3-34 (1995).

Joosten et al., "IL-1αβ Blockade Prevents Cartilage and Bone Destruction in Murine Type II Collagen-Induced Arthritis, Whereas TNF-α Blockade Only Ameliorates Joint Inflammation" *J. Immunol.* 163:5049-5055 (1999).

Kang et al., "Ex Vivo Gene Transfer to Chondrocytes in Full-Thickness Articular Cartilage Defects: A Feasibility Study." *Osteoarthritis and Cartilage.* 5(2):139-143 (1997).

Kang et al., "Gene Therapy for Arthritis: Principles and Clinical Practice." *Biochemical Society Transactions.* 25(2):533-537 (1997).

Kelley et al., "An insulin-like growth factor I-resistant state in cartilage of diabetic rats, etc." *Diabetes* 42(3):463-469 (1993).

Kemmler et al., "Studies on the conversion of proinsulin to insulin" *Journal of Biological Chemistry* 246(22):6786-6791 (1971).

Kimura et al., "Chondorcytes Embedded in Collagen Gels Maintain Cartilage Phenotype During Long-Term Cultures." *Clin. Orth. Relat. Res.* (Basic Science and Pathology, Sect. III) 186:231-239 (Jun. 1984).

Klyushnichenko et al., "High-performance liquid chromatography and high-performance capillary electrophoresis control in the analysis, etc." *J. Chromatography* 661:83-92 (1994).

Kong et al., "Activated T Cells Regulate Bone Loss and Joint Destruction in Adjuvant Arthritis through Osteoprotegerin Ligand" *Nature* 402(6759):304-309 (1999).

Kroeff et al., "Production scale purification of biosynthetic human insulin by reversed-phase high-performance liquid chromatography" *J. Chromatography* 461:45-61 (1989).

Kulkarni et al., "Polylactic acid for surgical implants" *Arch. Surg.* 93:839-843 (Nov. 1966).

Lewis, D., "Controlled release of bioactive agents from lactide/glycolide polymers", New York:Biodegradable Polymers as Drug Delivery Systems pp. 1-41 (1990).

Lieberman and Ove, "Growth factors for mammalian cells in culture" *Journal of Biological Chemistry* 234(10):2754-2758 (1959).

Lowman et al., "Molecular Mimics of Insulin-Like Growth Factor I (IGF-1) for Inhibiting IGF-1: IGF-Binding Protein Interactions." *Biochemistry* 37(25):8870-8878 (1998).

Maor et al., "Insulin Enhances the Growth of Cartilage in Organ and Tissue Cultures of Mouse Neonatal Mandibular Condyle" *Calcif. Tissue Int.* 52:291-299 (1993).

Martel-Pelletier et al., "Cytokines and Their Role in the Pathophysiology of Osteoarthritis." *Front. Bioscience.* 4:d694-703 (Oct. 1999).

Martel-Pelletier et al., "IGF/IGFBP axis in cartilage and bone in osteoarthritis pathogenesis" *Inflamm. Res.* 47:90-100 (1998).

Martel-Pelletier et al., "The interleukin-1 receptor in normal and osteoarthritic human articular chondrocytes. Identification as the type I receptor and analysis of binding kinetics and biologic function" *Arthritis and Rheumatism* 35(5):530-540 (1992).

Martin et al., "Age-Related Decline in Chondrocyte Response to Insulin-Like Growth Factor-I: The Role of Growth Factor Binding Proteins" *J. Orthop. Res.* 15:491-498 (1997).

*The Merck Manual*, 17th edition pp. 449.

Messner, K., "Hydroxylapatite supported dacron plugs for repair of isolated full-thickness defects of the rabbit femoral condyle" (40th Annual Meeting, Orthop. Res. Soc., Feb. 21-24, New Orleans, LA) pp. 239-241 (1994).

Monod et al., "On the nature of allosteric translations: a plausible model" *J. Mol. Biol.* 12:88-118 (1965).

Morales, T. I., "The Role and Content of Endogenous Insulin-Like Growth Factor-Binding Proteins in Bovine Articular Cartilage" *Arch Biochem. Biophys.* 343(2):164-172 (Jul. 1997).

Moriyama et al., "Hyaluronic acid grafted with poly(ethylene glycol) as a novel peptide formulation" *Journal of Controlled Release* 59:77-86 (1999).

Moses, A.C., "Recombinant insulinlike growth factor-I as therapy in states of altered carbohydrate homeostasis" *Curr. Opin. Endocrin. Diab.* 4:16-25 (1997).

Mow et al., "Cartilage and diarthrodial joints as paradigms for hierarchical materials and structures" *Biomaterials* 13(2):67-97 (1992).

Nixon et al., "Long-term survival and neocartilage maturation following extensive articular resurfacing with chondrocyte laden collagen scaffolds" (40th Annual Meeting, Orthop. Res. Soc., Feb. 21-24, New Orleans, LA) pp. 237-241 (1994).

Olney et al., "Chondrocytes from Osteoarthritic Cartilage Have Increased Expression of Insulin-Like Growth Factor I (IGF-I) and IGF-Binding Protein-3 (IGFBP-3) and -5, but not IGF-II or IGFBP-4" *J. Clin. Endo. and Metab.* 81(3):1096-1103 (1996).

Osborn et al., "Growth Factor Stimulation of Adult Articular Cartilage" *J. Orthoped. Res.* 7(1):35-42 (1989).

Paul and Pearson, "The action of insulin on the metabolism of cell cultures" *J. Endocrinol.* 21:287-294 (1960).

Pelletier et al., "Cytokines and inflammation in cartilage degradation" *Osteoarthritis Ed. of Rheum.* 19(3):545-568 (Aug. 1993).

Pelletier et al., "Reduced progression of experimental osteoarthritis in vivo by selective inhibition of inducible nitirc oxide synthase" *Arthritis Rheum.* 41(7):1275-1286 (1998).

Pietta and Mauri, "Application of micellar electrokinetic capillary chromatography to the determination of flavonoid drugs" *J. Chromatography* 549:367-373 (1991).

Portha et al., "The rat models of non-insulin dependent diabetes induced by neonatal streptozotocin" *Diabete & Metabolisme* (Paris) 15:61-75 (1989).

Posever et al., "Effects of Basic Fibroblast Growth Factor, Transforming Growth Factor-B1, Insulin-like Growth Factor-1, etc." *J. Orthoped. Res.* 13:832-837 (1995).

Prasad and Rajan, "Effect of insulin on bone in tissue culture" *Acta orthop. scand.* 41:44-56 (1970).

Renoux et al., "Release of mast cell mediators and nitrites into knee joint fluid in osteoarthritis-comparison with articular chondrocalcinosis and rheumatoid arthritis" *Osteoarth. and Cartil.* 4:175-179 (1996).

Rich et al., "The use of periosteal cell/polymer tissue constructs for the repair of articular cartilage defects" (40th Annual Meeting, Orthop. Res. Soc., Feb. 21-24, New Orleans, LA) pp. 241-241 (1994).

Robinson et al., "Changes in Proteoglycans of Intervertegral Disc in Diabetic Patients" *SPINE* 23(8):849-856 (1998).

Rogachefsky et al., "Treatment of canine osteoarthritis with insulin-like growth factor-1 (IGF-1) and sodium pentosan polysulfate" *Osteoarthritis and Cartilage* 1:105-114 (1993).

Rogachefsky et al., "Treatment of Canine Osteoarthritis with Sodium Pentosan Polysulfate and Insulin-Like Growth Factor-1" *Annals NY Acad. Sci.* 732:392-394 (1994).

Roszkowski-Sliz, W., "Effect of the Somatotropic Hormone, Insulin and Durabolin on Postadjuvant Polyarthritis in Rats" *Acta Physiol. Pol.*, Warsaw:Dept. of Pathophysiology, Reumathological Inst. vol. XXIV(2):371-376 (1973).

Sah et al., "Differential Effects of bFGF and IGF-1 on Matrix Metabolism in Calf and Adult Bovine Cartilage Explants" *Arch. Biochem. and Biophys.*, Academic Press, Inc. vol. 308(1):137-147 (1994).

Salmon Jr., W., "Importance of amino acids in the actions of insulin and serum sulfation factor to stimulate sulfate uptake by cartilage from hypophysectomized rats" *J. Lab. & Clin. Med.* 56:673-681 (Nov. 1960).

Salmon, Jr. et al., "Stimulation by insulin in vitro of incorporation of (S)sulfate and (C)leucine into protein-polysaccharide complexes, (H)uridine into RNA, and (H)thymidine into DNA of costal cartilage from hypophysectomized rats" *Endocrinology* 82:493-499 (Mar. 1968).

Sato and Urist., "Bone Morphogenetic Protein-Induced Cartilage Development in Tissue Culture." *Clin. Ortho. Rel. Res.* (Sect. II, Basic Science and Pathology) 183:180-187 (Mar. 1984).

Schafer et al., "Proteoglycan Metabolism is Age Related and Modulated by Isoforms of Platelet-Derived Growth Factor, etc." *Archives of Biochemistry & Biophysics* 302(2):431-438 (1993).

Schalkwijk et al., "Chondrocyte nonresponsiveness to insulin-like growth factor 1 in experimental arthritis" *Arthritis and Rheumatism* 32(7):894-900 (1989).

Schiller and Dorfman, "The metabolism of mucopolysaccharides in animals", Chapter IV, 227:625-632 (1957).

Schwartz and Amos, "Insulin Dependence of Cells in Primary Culture: Influence on Ribosome Integrity" *Nature* 219:1366-1367 (1968).

Smith, R.L., "Degradative Enzymes in Osteoarthritis" *Front. Bioscience* 4:d704-712 (Oct. 15, 1999).

Spanheimer, R., "Correlation Between Decreased Collagen Production in Diabetic Animals and in Cells Exposed, etc." *Matrix* 12:101-107 (1992).

Stevens and Hascall, "Characterization of Proteoglycans Synthesized by Rat Chondrosarcoma Chondrocytes Treated with Multiplication-stimulating Activity and Insulin" *Journal of Biological Chemistry*, Bethesda, MD:Lab. of Biochem., Natl. Inst. of Dental Res. vol. 256(4):2053-2058 (Feb. 25, 1981).

Stichtenoth and Frolich, "Nitric oxide and inflammatory joint diseases" *Brit. J. Rheum.* 37:246-257 (1998).

Thim et al., "Secretion and processing of insulin precursors in yeast" *Proc. Natl. Acad. Sci. USA* 83:6766-6770 (Sep. 1986).

Toolan et al., "Development of Novel Osteochondral Graft for Cartilage Repair." *J. Biomed. Mater. Res.* 41(2):244-250 (1998).

Umpierrez et al., "Correction of Altered Collagen Metabolism in Diabetic Animals with Insulin Therapy" *Matrix* (XP-001064200) 9:336-342 (1989).

van Heuningen et al., "Protection From Interleukin 1 Induced Destruction of Articular Cartilage by Transforming Growth Factor β: Studies in Anatomically Intact Cartilage In Vitro and In Vivo." *Annals of Rheum. Diseases.* 52(3):185-191 (1993).

van de Loo et al., "Reduced cartilage proteoglycan loss during zymosan-induced gonarthritis in NOS2-deficient mice and in anti-interleukin-1-treated wild-type mice with unabated joint inflammation" *Arthritis Rheum.* 41(4):634-646 (1998).

van de Loo et al., "Role of interleukin-1, tumor necrosis factor α, and interleukin-6 in cartilage proteoglycan metabolism and destruction. Effect of in situ blocking in murine antigen- and zymosan-induced arthritis" *Arthritis Rheum.* 38(2):164-172 (Feb. 1995).

van den Berg et al., "The Mouse Patella Assay" *Rheum. Int.* 1:165-169 (1982).

van der Kraan et al., "Inhibition of Proteoglycan Synthesis by Transforming Growth Factor β in Anatomically Intact Articular Cartilage of Murine Patellae" *Annals Rheum. Dis.* 51(5):643-647 (1992).

Verschure et al., "Responsiveness of articular cartilage from normal and inflamed mouse knee joints to various growth factors" *Annals Rheum. Dis.* 53(7):455-460 (1994).

Wakitani et al., "Repair of large cartilage defects in weight-bearing and partial weight-bearing articular surfaces with allograft articular chondrocytes embedded in collagen gels" (40th Annual Meeting, Orthop. Res. Soc., Feb. 21-24, New Orleans, LA) pp. 238-241 (1994).

Wei et al., "Mechanical Load and Primary Guinea Pig Osteoarthrosis." *Acta Orthop. Scand.* 69(4):351-357 (1998).

Williams et al., "Cytoplasmic inclusion bodies in *Escherichia coli* producing biosynthetic human insulin proteins" *Science* 215:687-689 (Feb. 1982).

Yanaihara et al., "Syntheses of C-peptides and human proinsulin" *Diabetes* 27:149-160 (1978).

Yasuda et al., "Long-acting pharmaceutical interferon" *Biomed. & Thera.* 27(10):1221-1223 (1993), English translation.

Young et al., "Osteoarthritis (osteoarthritis; degenerative joint disease)" *Spontaneous animal models*, Chapter 274, 2:257-261.

Younger et al., "Hepatic proliferative response to insulin in severe alloxan diabetes" *Cancer Research* (Part 1) 26:1408-1414 (Jul. 1966).

\* cited by examiner

Insulin has anabolic effects on articular cartilage explants

*p<0.05

Insulin or IGF-1 decreases Nitric Oxide release by AC explants

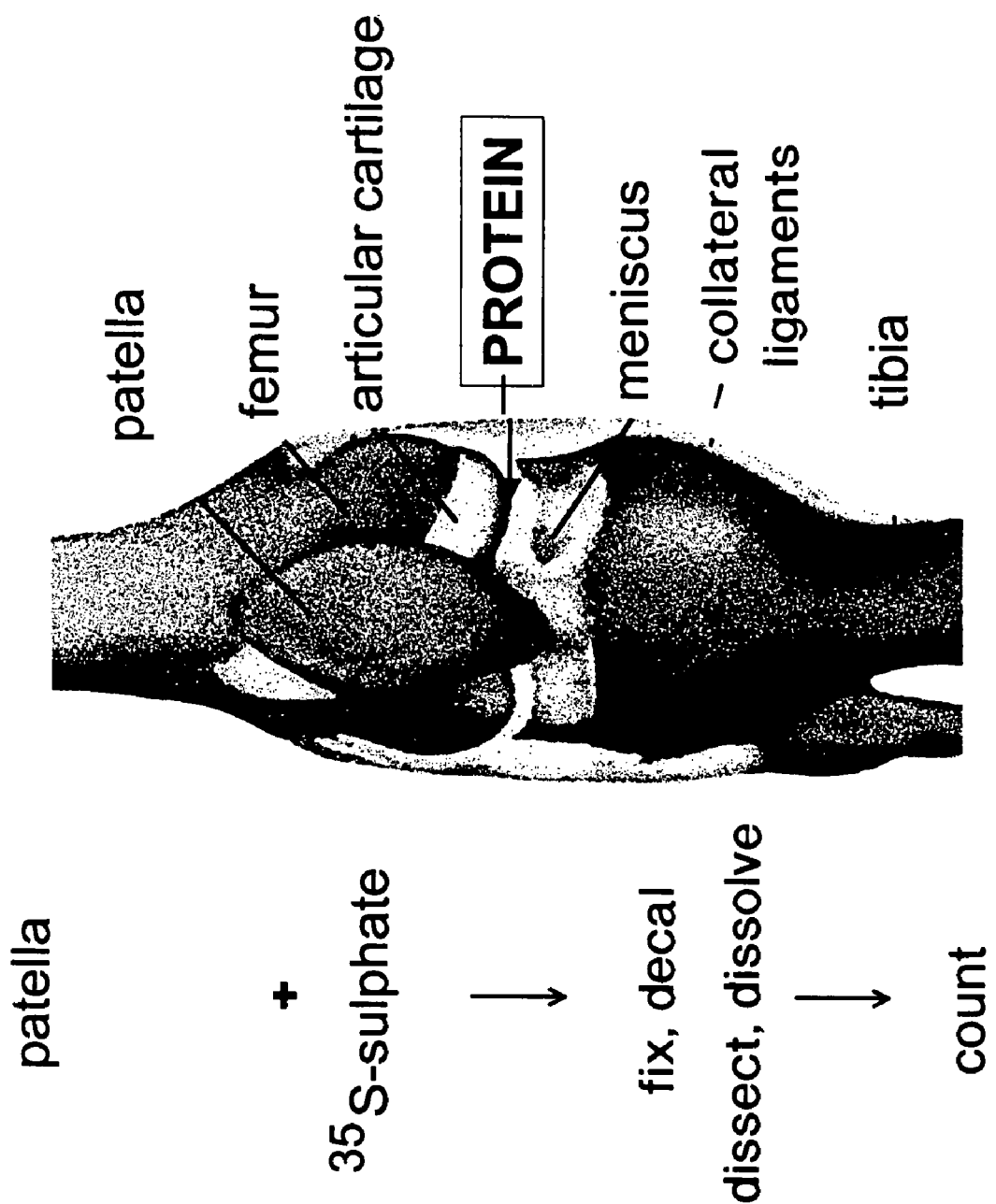

Effect of insulin on mouse patellae

Insulin has anabolic effects on normal and diseased cartilage

*$p<0.05$  **$p<0.005$

**p<0.005

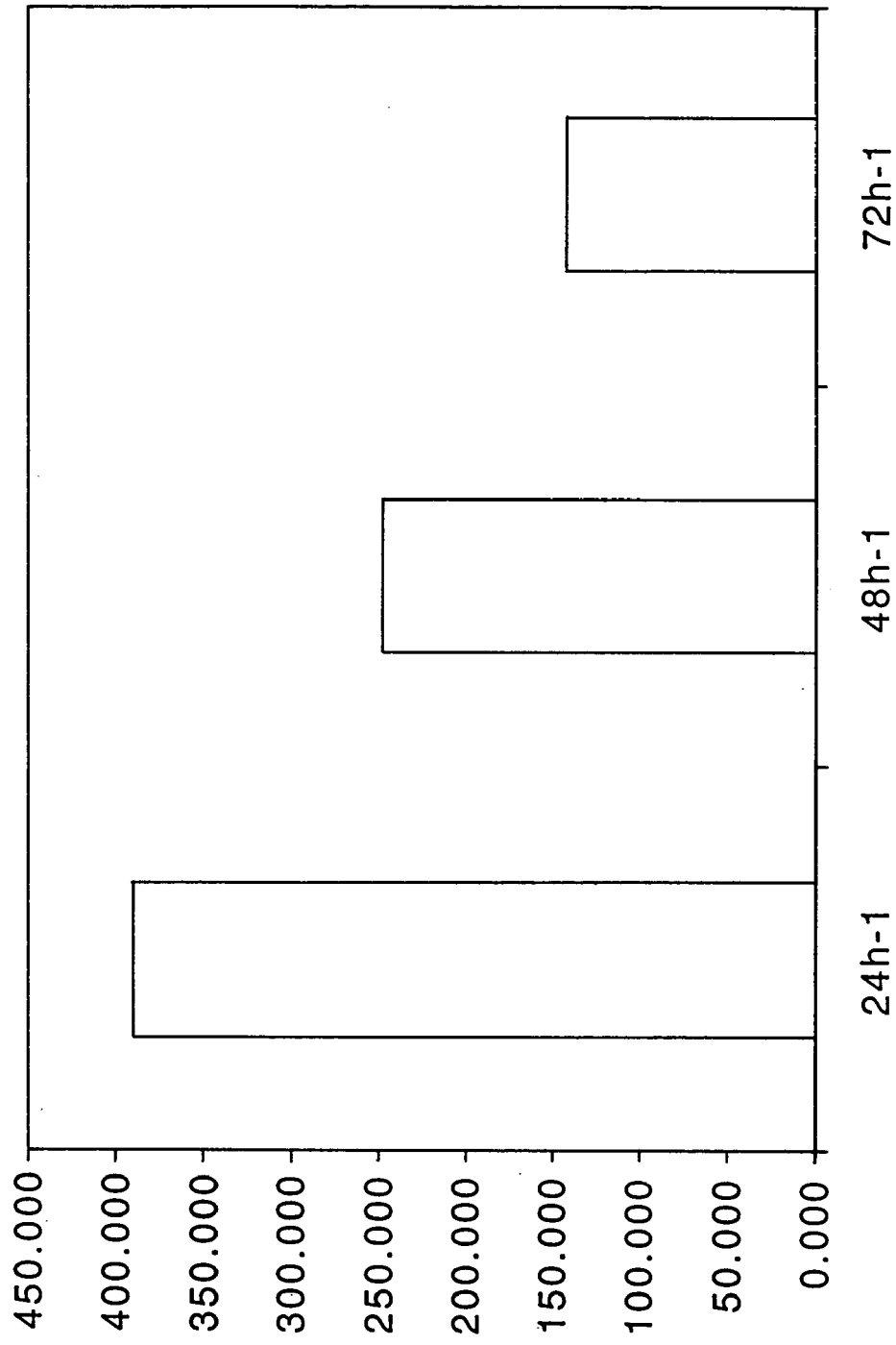

PLGA-Ins increases matrix synthesis

PLGA-Ins blocks IL-1a-suppression of matrix synthesis

GIVEQCCTSICSLYQLENYCN

FIG. 18A

FVNQHLCGSHLVEALYLVCGERGFFYTPKT

FIG. 18B

MALWMRLLPLLALLALWGPDPAAAFVNQHLCGSHLVEALYLVCGERGFFYTPKTRREAED
LQVGQVELGGGPGAGSLQPLALEGSLQKRGIVEQCCTSICSLYQLENYCN

FIG. 18C

RREAEDLQVGQVELGGGPGAGSLQPLALEGSLQKR

FIG. 18D

SEQUENCE LISTING

```
<160> NUMBER OF SEQ ID NOS: 17

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln
 1               5                  10                  15

Leu Glu Asn Tyr Cys Asn
                20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys Thr
                20                  25                  30

<210> SEQ ID NO 3
<211> LENGTH: 110
<212> TYPE: PRT
<213> ORGANISM: Homo sapiens

<400> SEQUENCE: 3

Met Ala Leu Trp Met Arg Leu Leu Pro Leu Leu Ala Leu Leu Ala
 1               5                  10                  15

Leu Trp Gly Pro Asp Pro Ala Ala Ala Phe Val Asn Gln His Leu
                20                  25                  30

Cys Gly Ser His Leu Val Glu Ala Leu Tyr Leu Val Cys Gly Glu
                35                  40                  45

Arg Gly Phe Phe Tyr Thr Pro Lys Thr Arg Arg Glu Ala Glu Asp
                50                  55                  60

Leu Gln Val Gly Gln Val Glu Leu Gly Gly Pro Gly Ala Gly
                65                  70                  75

Ser Leu Gln Pro Leu Ala Leu Glu Gly Ser Leu Gln Lys Arg Gly
                80                  85                  90

Ile Val Glu Gln Cys Cys Thr Ser Ile Cys Ser Leu Tyr Gln Leu
                95                  100                 105

Glu Asn Tyr Cys Asn
                110
```

-continued

```
<210> SEQ ID NO 4
<211> LENGTH: 35
<212> TYPE: PRT
<213> ORGANISM: Homo sapiens

<400> SEQUENCE: 4

Arg Arg Glu Ala Glu Asp Leu Gln Val Gly Gln Val Glu Leu Gly
 1               5                  10                  15

Gly Gly Pro Gly Ala Gly Ser Leu Gln Pro Leu Ala Leu Glu Gly
                20                  25                  30

Ser Leu Gln Lys Arg
                35

<210> SEQ ID NO 5
<211> LENGTH: 5
<212> TYPE: PRT
<213> ORGANISM: Artificial sequence
<220> FEATURE:
<223> OTHER INFORMATION: proteolytic cleavage site
<220> FEATURE:
<221> NAME/KEY: unsure
<222> LOCATION: 3
<223> OTHER INFORMATION: unknown amino acid

<400> SEQUENCE: 5

Lys Arg Xaa Lys Arg
 1               5

<210> SEQ ID NO 6
<211> LENGTH: 4
<212> TYPE: PRT
<213> ORGANISM: Artificial sequence
<220> FEATURE:
<223> OTHER INFORMATION: proteolytic cleavage site
<220> FEATURE:
<221> NAME/KEY: unsure
<222> LOCATION: 3
<223> OTHER INFORMATION: unknown amino acid

<400> SEQUENCE: 6

Lys Arg Xaa Met
 1

<210> SEQ ID NO 7
<211> LENGTH: 4
<212> TYPE: PRT
<213> ORGANISM: Artificial sequence
<220> FEATURE:
<223> OTHER INFORMATION: proteolytic cleavage site
<220> FEATURE:
<221> NAME/KEY: unsure
<222> LOCATION: 2
<223> OTHER INFORMATION: unknown amino acid

<400> SEQUENCE: 7

Asn Xaa Lys Arg
 1

<210> SEQ ID NO 8
<211> LENGTH: 6
<212> TYPE: PRT
<213> ORGANISM: Artificial sequence
<220> FEATURE:
<223> OTHER INFORMATION: alternative C-peptide

<400> SEQUENCE: 8

Arg Arg Gly Ser Lys Arg
```

<210> SEQ ID NO 9
<211> LENGTH: 33
<212> TYPE: PRT
<213> ORGANISM: Artificial sequence
<220> FEATURE:
<223> OTHER INFORMATION: C-terminal addition to Beta-peptide disclosed
      in US 5,514,646

<400> SEQUENCE: 9

Glu Ala Glu Asp Leu Gln Val Gly Gln Val Glu Leu Gly Gly Gly
 1               5                  10                  15

Pro Gly Ala Gly Ser Leu Gln Pro Leu Ala Leu Gly Gly Ser Leu
                20                  25                  30

Gln Lys Arg

<210> SEQ ID NO 10
<211> LENGTH: 56
<212> TYPE: PRT
<213> ORGANISM: Artificial sequence
<220> FEATURE:
<223> OTHER INFORMATION: Portion of insulin variant from EP 171,886.

<400> SEQUENCE: 10

Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys Thr
                20                  25                  30

Arg Arg Glu Ala Glu Asp Leu Gln Val Gly Gln Val Glu Leu Gly
                35                  40                  45

Gly Gly Pro Gly Ala Gly Ser Leu Gln Pro Leu
                50                  55

<210> SEQ ID NO 11
<211> LENGTH: 7
<212> TYPE: PRT
<213> ORGANISM: Artificial sequence
<220> FEATURE:
<223> OTHER INFORMATION: Portion of insulin variant from EP 171,886.

<400> SEQUENCE: 11

Ala Leu Glu Gly Ser Leu Gln
 1               5

<210> SEQ ID NO 12
<211> LENGTH: 9
<212> TYPE: PRT
<213> ORGANISM: Artificial sequence
<220> FEATURE:
<223> OTHER INFORMATION: Portion of insulin variant from EP 171,886.

<400> SEQUENCE: 12

Ala Leu Glu Gly Ser Leu Gln Lys Arg
 1               5

<210> SEQ ID NO 13
<211> LENGTH: 54
<212> TYPE: PRT
<213> ORGANISM: Artificial sequence
<220> FEATURE:
<223> OTHER INFORMATION: Portion of insulin variant from EP 171,147.

<400> SEQUENCE: 13

```
Glu Ala Glu Asp Leu Gln Val Gly Gln Val Glu Leu Gly Gly Gly
 1               5                  10                  15

Pro Gly Ala Gly Ser Leu Gln Pro Leu Ala Leu Glu Gly Ser Leu
                 20                  25                  30

Gln Lys Arg Gly Ile Val Glu Gln Cys Cys Thr Ser Ile Cys Ser
                 35                  40                  45

Leu Tyr Gln Leu Glu Asn Tyr Cys Asn
                 50
```

<210> SEQ ID NO 14
<211> LENGTH: 32
<212> TYPE: PRT
<213> ORGANISM: Artificial sequence
<220> FEATURE:
<223> OTHER INFORMATION: Portion of insulin variant from EP 171,147.

<400> SEQUENCE: 14

```
Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys Thr
                 20                  25                  30

Arg Arg
```

<210> SEQ ID NO 15
<211> LENGTH: 30
<212> TYPE: PRT
<213> ORGANISM: Artificial sequence
<220> FEATURE:
<223> OTHER INFORMATION: Portion of insulin variant from EP 171,147
      and EP 171,887.

<400> SEQUENCE: 15

```
Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys Thr
                 20                  25                  30
```

<210> SEQ ID NO 16
<211> LENGTH: 30
<212> TYPE: PRT
<213> ORGANISM: Artificial sequence
<220> FEATURE:
<223> OTHER INFORMATION: Portion of insulin variant from EP 171,887.

<400> SEQUENCE: 16

```
Ala Leu Glu Gly Ser Leu Gln Lys Arg Gly Ile Val Glu Gln Cys
 1               5                  10                  15

Cys Thr Ser Ile Cys Ser Leu Tyr Gln Leu Glu Asn Tyr Cys Asn
                 20                  25                  30
```

<210> SEQ ID NO 17
<211> LENGTH: 26
<212> TYPE: PRT
<213> ORGANISM: Artificial sequence
<220> FEATURE:
<223> OTHER INFORMATION: Portion of insulin variant from EP 171,887.

<400> SEQUENCE: 17

```
Arg Arg Glu Ala Glu Asp Leu Gln Val Gly Gln Val Glu Leu Gly
 1               5                  10                  15

Gly Gly Pro Gly Ala Gly Ser Leu Gln Pro Leu
                 20                  25
```

USE OF INSULIN FOR THE TREATMENT OF CARTILAGINOUS DISORDERS

RELATED APPLICATIONS

This application is a continuation of U.S. Ser. No. 09/815,229 filed Mar. 22, 2001, now U.S. Pat. No. 6,689,747, which claims priority under 35 USC 119(e) to provisional application No. 60/192,103 filed Mar. 24, 2000; all of which are incorporated herein by reference.

FIELD OF THE INVENTION

The present invention relates generally to the repair of cartilage and the treatment of cartilaginous disorders.

BACKGROUND OF THE INVENTION

Cartilaginous disorders broadly describe a collection of diseases characterized by degeneration of or metabolic abnormalities in the connective tissues which are manifested by pain, stiffness and limitation of motion of the affected body parts. The origin of these disorders can be pathological or as a result of trauma or injury.

Osteoarthritis (OA), also known as osteoarthrosis or degenerative joint disease, is the result of a series of localized degenerative processes that affect the articular structure and result in pain and diminished function. The incidence of OA increases with age, and evidence of OA can be detected at least one joint in the majority of the population by age 65. OA is often accompanied by a local inflammatory component that may accelerate joint destruction.

OA is characterized by disruption of the smooth articulating surface of cartilage, with early loss of proteoglycans (PG) and collagens, followed by formation of clefts and fibrillation, and ultimately by full-thickness loss of cartilage. Coincident with the cartilaginous changes are alterations in periarticular bone. The subchondral bone thickens and is slowly exposed. Bony nodules or osteophytes also often form at the periphery of the cartilage surface and occasionally grow over the adjacent eroded areas. OA symptoms include local pain at the affected joints, especially after use. With disease progression, symptoms may progress to a continuous aching sensation, local discomfort and cosmetic alterations such as deformity of the affected joint.

In contrast to the localized nature of OA, rheumatoid arthritis (RA) is a systemic, inflammatory disease which likely begins in the synovium, the tissues surrounding the joint space. The prevalence of RA is about ⅙ that of OA in the general population of the United States. RA is a chronic autoimmune disorder characterized by symmetrical synovitis of the joint and typically affects small and large diarthrodial joints, leading to their progressive destruction. As the disease progresses, the symptoms of RA may also include fever, weight loss, thinning of the skin, multiorgan involvement, scleritis, corneal ulcers, the formation of subcutaneous or subperiosteal nodules and premature death. While the cause of RA and OA are distinctly different, the cytokines and enzymes involved in cartilage destruction appear to be similar.

Because mature chondrocytes have little potential for replication, and since recruitment of other cell types is limited by the avascular nature of cartilage, mature cartilage has limited ability to repair itself. For this reason, transplantation of cartilage tissue or isolated chondrocytes into defective joints has been used therapeutically. However, tissue transplants from donors run the risk of graft rejection as well as possible transmission of infectious diseases. Although these risks can be minimized by using the patient's own tissue or cells, this procedure requires further surgery, creation of a new lesion in the patient's cartilage, and expensive culturing and growing of patient-specific cells. Better healing is achieved if the subchondral bone is penetrated, either by injury/disease or surgically, because the penetration into the vaculature allows recruitment and proliferation of undifferentiated cells to effect repair. Unfortunately, the biochemical and mechanical properties of this newly formed fibrocartilage differ from those of normal hyaline cartilage, resulting in inadequate or altered function. Fibrocartilage does not have the same durability and may not adhere correctly to the surrounding hyaline cartilage. For this reason, the newly synthesized fibrocartilage may be more prone to breakdown and loss than the original articular hyaline cartilage tissue.

Peptide growth factors are very significant regulators of cartilage growth and cartilage cell (chondrocyte) behavior (i.e., differentiation, migration, division, and matrix synthesis or breakdown) F. S. Chen et al., *Am J. Orthop.* 26: 396-406 (1997). Growth factors that have been previously proposed to stimulate cartilage repair include insulin-like growth factor (IGF-1), Osborn, *J. Orthop. Res.* 7: 35-42 (1989); Florini & Roberts, *J. Gerontol.* 35: 23-30 (1980); basic fibroblast growth factor (bFGF), Toolan et al., *J. Biomec. Mat. Res.* 41: 244-50 (1998); Sah et al., *Arch. Biochem. Biophys.* 308: 137-47 (1994); bone morphogenetic protein (BMP), Sato & Urist, *Clin. Orthop. Relat. Res.* 183: 180-87 (1984); Chin et al., *Arthritis Rheum.* 34: 314-24 (1991) and transforming growth factor beta (TGF-β), Hill & Logan, *Prog. Growth Fac. Res.* 4: 45-68 (1992); Gueme et al., *J. Cell Physiol.* 158: 476-84 (1994); Van der Kraan et al., *Ann. Rheum. Dis.* 51: 643-47 (1992). Treatment with peptide growth factors alone, or as part of an engineered device for implantation, could in theory be used to promote in vivo repair of damaged cartilage or to promote expansion of cells ex vivo prior to transplantation. However, because of their relatively small size, growth factors are rapidly absorbed and/or degraded, thus creating a great therapeutic challenge in trying to make them available to cells in vivo in sufficient quantity and for sufficient duration.

The present invention proposes to overcome this limitation by delivery of a growth factor with a vehicle, and/or as a slow-release formulation. The ideal delivery vehicle is biocompatible, resorbable, has the appropriate mechanical properties, and results in no harmful degradation products.

Another method of stimulating cartilage repair is to inhibit the activity of molecules which induce cartilage destruction and/or inhibit matrix synthesis. One such molecule is the cytokine IL-1α, which has detrimental effects on several tissues within the joint, including the generation of synovial inflammation and up-regulation of matrix metalloproteinases and prostaglandin expression. V. Baragi, et al., *J. Clin. Invest.* 96: 2454-60 (1995); V. M. Baragi et al., *Osteoarthritis Cartilage* 5: 275-82 (1997); C. H. Evans et al., *J. Leukoc. Biol.* 64: 55-61 (1998); C. H Evans and P. D. Robbins, *J. Rheumatol.* 24: 2061-63 (1997); R. Kang et al., *Biochem. Soc. Trans.* 25: 533-37 (1997); R. Kang et al., *Osteoarthritis Cartilage* 5: 139-43 (1997). One means of antagonizing IL-1α is through treatment with soluble IL-1 receptor antagonist (IL-1ra), a naturally occurring protein that prevents IL-1 from binding to its receptor, thereby inhibiting both direct and indirect effects of IL-1 on cartilage. Other cytokines, such as IL-1β, tumor necrosis factor alpha (TNF-α), interferon gamma (IFN-γ), IL-6 and IL-8 have been linked to increased activation of synovial fibroblast-like cells, chondrocytes and/or macrophages. The inhibition of these cytokines may be of therapeutic benefit in preventing inflammation and cartilage destruction. In fact, molecules which inhibit TNF-α activity have been shown to have potent beneficial effects on the joints of patients with rheumatoid arthritis.

Nitric oxide also likely plays a substantial role in destruction of cartilage. [Ashok et al., *Curr. Opin. Rheum.* 10: 263-268 (1998)]. Unlike normal joint tissue which does not produce NO unless stimulated with cytokines such as IL-1, synovial membranes or cartilage obtained from arthritic joints spontaneously produce large amounts of nitric oxide for up to 3 days after removal from the joint. In addition, increased concentrations of nitrites are found in synovial fluid of arthritic patients. In addition to its direct stimulation of cartilage catabolism, nitric oxide present in an inflamed joint would likely lead to increased vasodilation and permeability, further release of cytokines such as TNF-α and IL-1 from leukocytes, and stimulation of angiogenesis. Evidence for a causative role of NO in arthritis, comes from animal models where inhibition of NO has been shown to prevent IL-1 mediated cartilage destruction and chondrocyte death as well as progression of osteoarthritis. Finally, several agents (such as auranofin, glucocorticoids, cyclosporins, tetracyclines, and at least some nonsteroidal anti-inflammatory drugs including aspirin) currently used for the treatment of human rheumatic diseases, have been shown to reduce NO production and/or activity.

Prior studies in diabetic (with altered serum insulin levels) or abnormal (hypophysectomized) animals suggests that insulin is required for optimal production of sulfated mucopolysaccharides and collagen, two major components of connective tissue. As early as 1957, insulin was shown to increase the otherwise abnormally low uptake of labeled sulfate into the skin of diabetic rats Schiller and Dorfman, *J. Biol. Chem.* 227: 625-632 (1957). Similarly, insulin increased the otherwise low level of sulfate uptake in aortae from diabetic rats. Cohen, M. P. and Foglia, V. G. *Proc. Soc. Exp. Biol. Med.* 132: 376-378 (1969); *Proc. Soc. Exp. Biol. Med.* 133: 1275-1278 (1970); *Proc. Soc. Exp. Biol. Med.* 135: 113-115 (1970). Subsequently, insulin was shown to stimulate uptake of sulfate into cartilage, but the identity of the molecules into which the sulfate was incorporated was not determined. Furthermore, the effect of insulin on endogenous matrix turnover (i.e. protein breakdown or retention within the matrix) was not assessed. Salmon, W. D., Jr., and Daughaday, W H. *Endocrinol.* 82: 493-499 (1957); J. Posever et al., *J. Orthopaedic Res.* 13: 832-827 (1995). While insulin may have direct effects on connective tissues, at least some data suggests that the defects in connective tissue metabolism found in diabetic animals, which can be at least partially reversed by systemic administration of insulin, could be due to circulating factor(s) induced by insulin and not due to direct effects of insulin on connective tissues (Spanheimer, R. G., *Matrix* 12: 101-107 (1992).

Insulin has also been found to stimulate the growth of mouse fibroblast cultures, Paul and Pearson, *J. Endocrinol.* 21: 287-294 (1960), cartilage cells from hypophysectomized rats (Salmon, W. D., Jr., *J. Lab. Clin. Med.* 56: 673-681 (1960), cells in bone cultures (Prasad, G. C. and Rajan, K. T., *Acta Orthop. Scand.* 41: 44-56 (1970), as well as cells in many other systems (Gey, G. O. and Thalhimer, W., *J. Amer. Med. Assoc.* 82: 1609 (1924); Lieberman, I., and Ove, P. O., *J. Biol. Chem.* 234: 2754-2758 (1959); Younger, L. R., King, J. and Steiner, O. F., *Cancer Res.* 26: 1408-1413 (1966); Schwartz, A. G. and Amos, H., *Nature* 219: 1366-1367 (1968). Most of these very early studies were performed on whole animals, organs, or tissues. Hajek and Solursh, *Gene Comp. Endocrin.* 25: 432-446 (1975) were among the first to show a direct effect of insulin on chondrocytes, derived from chick embryo sternal cartilage, in serum-free cultures. The stimulation of growth and mucopolysaccharide synthesis by insulin in these cultures may not be surprising given that the hormone insulin increases amino acid uptake, promotes a positive nitrogen balance, and favors overall protein synthesis. Similarly the increase in proteoglycan synthesis stimulated by insulin in rat tumor cells derived from a Swarm rat chondrosarcoma was accompanied by an increase in incorporation of radioisotope into total protein and thus may reflect a general increase in protein synthesis (Stevens, R. L. and Hascall, V. C., *JBC* 256: 2053-2058 (1981). Finally, it should be understood that high levels of insulin (10 µg/ml for the chick cultures, Hajek and Solursh, supra) were used in many of these studies. At such high concentrations insulin binds to, and activates, the insulin-like growth factor (IGF)-1 receptor, thus mimicking the effects of IGF-1 itself. Thus, the observed physiological effects could be the result of IGF-1 receptor signalling and merely the result of insulin signalling. Finally, systemic administration of insulin had no effect in an inflammatory, polyarthritic model in rats in which only the number of swollen joints was monitored. Roszkowski-Sliz, W., *Acta Physiol. Pol. XXIV,* 371-376 (1973). Since inflammation can occur in the absence of cartilage and bone destruction and vice versa in animal models, Joosten et al., *J. Immunol.* 163: 5049-5055 (1999), how insulin may have affected the underlying joint tissues in this study is not clear.

More than thirty years ago, high doses of insulin were injected subcutaneously into 10 patients, 7 of whom had rheumatoid arthritis, with the goal of inducing a hypoglycemic crisis, increasing corticosteroid levels, and thus altering adrenal gland activity (M. Ippolito et al., *Reumatismo* 20(5): 561-64 (1967). Insulin treatment associated with cortisone resulted in overall beneficial effects for the patients including regain of appetite, an increase in body weight, and improvement in pain. These effects may be due to indirect activities of insulin, for example the ability of insulin to increase plasma corticosteroid levels Since the authors were most interested in the effects of systemic insulin on the "diencephalohypophysial system", the anabolic effects of insulin on cartilage were not examined or considered. Furthermore, given the avascular nature of cartilage and the rapid clearance of insulin in vivo, it is unlikely that much if any of the subcutaneously-delivered insulin would have been available to chondrocytes within the joints of the insulin-treated individuals.

Unlike OA, bone loss is a common feature of RA. Japanese patent application JO 59-234,826, filed Nov. 7, 1984 also speculated on the potential application of insulin for the treatment of rheumatoid arthritis based on its induction of a bone marker, i.e. alkaline phosphatase activity, in the osteoblastic (bone) cell line, MC3T3-E1. However, the effects of insulin on cartilage tissue itself was not examined or considered.

As the population ages, and the incidence of arthritis increases, an effective therapy to induce repair of cartilage, including cartilage damaged as a result of injury and/or disease, is urgently needed.

SUMMARY OF THE INVENTION

The present invention concerns methods for the treatment, repair and protection of cartilage damaged as a result of a cartilaginous disorder, including that which results from disease and/or injury. More specifically, the invention concerns a method for the treatment, repair and protection of cartilage comprising administering an effective amount of insulin or an insulin variant. More specifically, the method provides for administration of insulin or insulin variant in a sustained- or extended-release form.

In a further embodiment, the present invention concerns a method for the treatment of cartilage damaged as a result of a cartilaginous disorder comprising contacting said cartilage with an effective amount of insulin and/or an insulin variant. Optionally, the cartilage is articular cartilage, and is contained within a mammal and the amount administered is a therapeutically effective amount. Optionally, the cartilaginous disorder is osteoarthritis, rheumatoid arthritis or an in injury.

In a further embodiment, the present invention concerns a method for the treatment of cartilage damaged by injury or preventing the initial or continued damage comprising contacting said cartilage with an effective amount of insulin or insulin variant. More specifically, the injury treated is microdamage or blunt trauma, a chondral fracture, an osteochondral fracture, or damage to tendons, menisci, or ligaments. More specifically, the cartilage is contained within a mammal, including humans, and the amount administered is a therapeutically effective amount. In a specific aspect, the injury can be the result of excessive mechanical stress or other biomechanical instability resulting from a sports injury or obesity. Alternatively, the present invention concerns a method of treating or facilitating the repair of bone fractures comprising contacting the region of the bone injury with an effective amount of insulin or insulin variant.

In a further embodiment, the present invention concerns a method for the treatment of cartilage damaged or preventing initial or continued damage by a cartilaginous disorder and/or injury comprising contacting said cartilage with an effective amount of a composition further comprising insulin or insulin variant. Alternatively, the composition further comprises a carrier, excipient or stabilizer. Alternatively, the cartilage is present in a mammal and the amount administered is a therapeutically effective amount. Alternatively, the composition may be administered via injection or infusion by intravenous, intraarterial, intraperitoneal, intramuscular, intralesional, intraarticular or topical administration to a mammal and the amount administered is a therapeutically effective amount. Alternatively, the composition is injected directly into the afflicted cartilaginous region or joint.

In a further embodiment, the present invention concerns a method for the treatment of cartilage damaged or preventing initial or continued damage by a cartilaginous disorder and/or injury comprising administrating a therapeutically effective amount of a sustained or extended-release composition containing insulin or insulin variant. Alternatively, the cartilage is present in a mammal and the amount administered is a therapeutically effective amount. More specifically, the extended- or sustained-release composition contains insulin or insulin variant formulated in a microencapsulation, a semi-permeable membrane of solid hydrophobic polymers, a biodegradable polymer(s), or a dispersion (e.g., suspension or emulsion). More specifically, the semi-permeable membrane of solid hydrophobic polymer is polylactic-co-glycolic acid (PLGA), and the biodegradable polymer is cross-linked hyaluronic acid (HA). Alternatively, the extended- or sustained-release insulin or insulin variant composition further comprises a water-soluble polyvalent metal salt. More specifically, the polyvalent metal salt includes the salt formed from a metallic cation and an inorganic or organic acid.

In a further embodiment, the invention concerns a method for treating cartilage damaged or preventing initial or continued damage as a result of injury or a cartilaginous disorder comprising contacting the cartilage with an effective amount of insulin or insulin variant in combination with an effective amount of a cartilage agent. Optionally, the cartilage is present inside a mammal and the amount administered is a therapeutically effective amount.

In another embodiment, the invention concerns a method of maintaining, enhancing or promoting the growth of chondrocytes in serum-free culture by contacting the chondrocytes with an effective amount of insulin or insulin variant. Alternatively, the method concerns contacting the chondrocyte with an effective amount of insulin or insulin variant in a sustained or extended-release formulation. Alternatively, the present invention concerns a method of stimulating the regeneration or preventing the degradation of cartilage resulting from injury or a cartilaginous disorder by transplantation of an effective amount of chondrocytes previously treated with an effective amount of insulin or insulin variant.

In a further embodiment, the present invention concerns a method for the treatment of cartilage damaged or preventing initial or continued damage as a result of injury or a cartilaginous disorder comprising contacting said cartilage with an effective amount of insulin and/or an insulin variant in combination with any standard cartilage surgical technique. The present invention may be administered prior, after and/or simultaneous to the standard cartilage surgical technique. In a specific aspect, the standard surgical technique may be selected from the following procedures: cartilage shaving, abrasion chondroplasty, laser repair, debridement, chondroplasty, microfracture with or without subchondral bone penetration, mosaicplasty, cartilage cell allografts, stem cell autografts, costal cartilage grafts, chemical stimulation, electrical stimulation, perichondral autografts, periosteal autografts, cartilage scaffolds, shell (osteoarticular) autografts or allografts, or osteotomy.

In a further embodiment, the invention concerns nucleic acid encoding insulin and/or insulin variants, and vectors and recombinant host cells comprising such nucleic acid.

In another embodiment, the present invention concerns a therapeutic kit, comprising insulin and/or an insulin variant and a carrier, excipient or stabilizer (e.g. a buffer) in suitable packaging. The kit preferably contains instructions for using insulin to treat cartilage damaged or to prevent initial or continued damage to cartilage as a result of a cartilaginous disorder. Alternatively, the kit may contain instructions for using insulin to treat a cartilaginous disorder.

In a further embodiment, the invention concerns an article of manufacture, comprising:

a container;

an instruction on the container; and a composition comprising an active agent contained within the container;

wherein the composition is effective for treating a cartilaginous disorder, the instruction on the container indicates that the composition can be used to treat a cartilaginous disorder, and the active agent in the composition is an agent stimulating the repair and/or preventing the degradation of cartilage. In a preferred aspect, the active agent is insulin or an insulin variant.

BRIEF DESCRIPTION OF THE DRAWINGS

FIG. 6 shows a pictorial diagram of the patella assay. Following intra-articular injection of a given "protein" into mouse knee joints, patellae were harvested, labelled with $^{35}$S-sulfate, fixed, decalcified, dissected away from the underlying bone, and counted. The amount of radioactivity incorporated into the cartilage is an indication of the extent of matrix synthesis.

FIG. 11 shows the effect of insulin on cartilage from diabetic mice. Patellae from diabetic, hypo-insulinemic mice (streptozotocin-treated) were harvested, and matrix synthesis was measured after culturing (18 hours) in the absence (−) or presence (+Ins) of 100 nM insulin (FIG. 6). Basal synthesis was lower in the diabetic (Diab−) than in the control mice (Con−). However, treatment with insulin brought synthesis levels in the cartilage from diabetic mice (Diab+Ins) to levels comparable to that of the untreated control (Con−Ins). Furthermore, the extent of induction in control and diabetic tissues was similar.

FIG. 13A shows release from days 1-3, whereas FIG. 13B is an expanded graph of data from FIG. 13A with release on days 2 and 3. Results are expressed as nM concentration of active insulin.

FIGS. 15A-B examine the effect on matrix breakdown. PLGA-Ins was added once (at time 0) to explants in the absence (FIG. 15A −) or presence (FIG. 15B +) of IL-1α (1 ng/ml), and the amount of proteoglycans in the media (i.e., released by the explants) was measured using the DMMB assay. Media was changed at 24 h, and 48 hr, without adding additional PLGA-Ins. In contrast, samples treated with insulin (10 nM) (Ins10) received fresh insulin with the media change at each timepoint (0, 24 h, 48 h). Results are expressed as proteoglycans (μg) released over 24 hours. A single treatment with PLGA-Ins was able to decrease both basal and IL-1α-induced matrix breakdown. FIGS. 15C-D examines the effect of PLGA-Ins on matrix synthesis. PLGA-Ins was added to explants in the absence (top) or presence (bottom, +) of IL-1α (1 ng/ml) for 3 days. PLGA-Ins was added only at time 0, while insulin (10 nM) (Ins10) was added with the media change at each timepoint (0, 24 h, 48 h). During the last 15 hours of treatment, explants were labelled with $^{35}$S-sulfate, and labelled matrix proteins were precipitated and counted (cpm). As shown here, PLGA-Ins induced matrix synthesis, and overcame IL-1α induced inhibition of proteoglycan synthesis. FIGS. 15E-F examines the effect on nitric oxide (NO) production. PLGA-Ins was added to explants in the absence (top) or presence (bottom, +) of IL-1α (1 ng/ml) and the amount of nitrite (μM) in the media was determined. PLGA-Ins was added only at time 0, while insulin (10 nM) (Ins10) was added with the media change at each timepoint (0, 24 h, 48 h). A single treatment with PLGA-Ins decreased basal nitric oxide production, and inhibited induction of nitric oxide synthesis by IL-1α.

FIG. 18 shows the human native sequence of the A-chain of native sequence A-chain (FIG. 18A)(SEQ ID NO:1), B-chain (FIG. 18B)(SEQ ID NO:2), native sequence proinsulin (FIG. 18C)(SEQ ID NO:3) and C-chain (FIG. 18D) (SEQ ID NO:4).

FIG. 19A shows the results on tissue removed from a 63 year old white male with degenerative joint disease (DJD) which was treated with IGF-1 (100 ng/ml), desIGF (100 ng/ml) or insulin (13.15 nM—equivalent molar concentration as 100 ng/ml IGF-1). FIG. 19B shows the results on tissue removed from a 70 year old female with osteoarthritis (OA) which was treated with IGF-1 (80 ng/ml), desIGF (80 ng/ml), or insulin (10.54 nM—equivalent molar concentration as 80 ng/ml IGF-1).

DETAILED DESCRIPTION OF THE INVENTION

Figure 1:
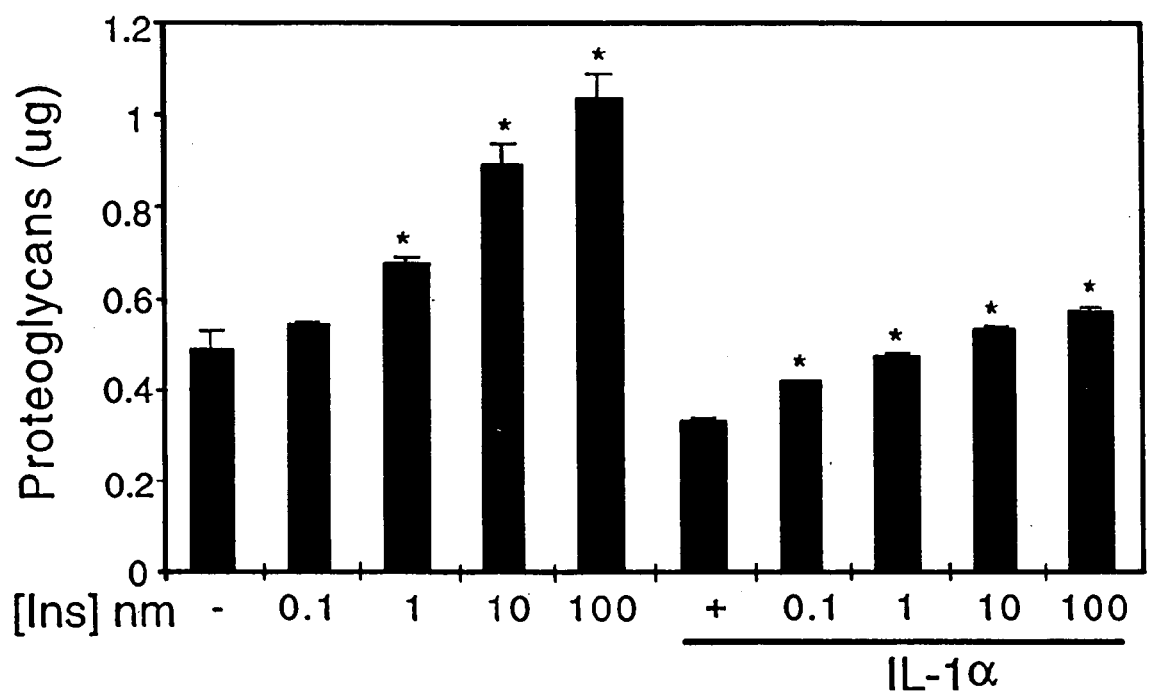
FIG. 1 shows the effect insulin has on matrix synthesis in primary articular chondrocytes (ACs). Insulin at various concentrations (0.1-100 nM) in serum-free media induced primary chondrocytes from porcine articular cartilage to increase proteoglycan synthesis relative to the untreated control samples (−) and was able to overcome interleukin 1α (IL-1α)-induced inhibition of synthesis. Media was analyzed for proteoglycan content using the colorimetric DMMB assay. "*" indicates a significant (p<0.05) difference from that of the corresponding control (− or +IL1α).

Osteoarthris v. Rheumatoid Arthritis:

Rheumatoid arthritis (RA) is a systemic, autoimmune, degenerative disease that causes symmetrical disruptions in the synovium of both large and small diarthroidal joints alike. As the disease progresses, symptoms of RA may include fever, weight loss, thinning of the skin, multiorgan involvement, scleritis, corneal ulcers, the formation of subcutaneous or subperiosteal nodules and premature death. In contrast to OA, RA symptoms appear during youth, extra-articular manifestations can affect any organ system, and joint destruction is symmetrical and occurs in both large and small joints alike. Extra-articular symptoms can include vasculitis, atrophy of the skin and muscle, subcutaneous nodules, lymphadenopathy, splenomegaly, leukopaenia and chronic anaemia. Furthermore, RA is heterogeneous in nature with a variable disease expression and is associated with the formation of serum rheumatoid factor in 90% of patients sometime during the course of the illness.

Interestingly, patients with RA also have a hyperactive immune system. The great majority of people with RA have a genetic susceptibility associated with increased activation of class II major histocompatibility complex molecules on monocytes and macrophages. These histocompatibility complex molecules are involved in the presentation of antigen to activated T cells bearing receptors for these class II molecules. The genetic predisposition to RA is supported by the prevalence of the highly conserved leukocyte antigen DR subtype Dw4, Dw14 and Dw15 in human patients with very severe disease.

The activated monocytes and macrophages, in interacting with the appropriate T cells stimulate a cascade of events including further activation of additional monocytes and macrophages, T cells, B cells and endothelial cells. With the upregulation of adhesion molecules, additional mononuclear cells and polymorphonuclear cells are attracted to the inflamed joint. This influx stimulates secretion of additional chemotactic cytokines, thereby enhancing the influx of inflammatory cells into the synovium and synovial fluid.

Osteoarthritis (OA) is a localized degenerative disease that affects articular cartilage and bone and results in pain and diminished joint function. OA may be classified into two types: primary and secondary. Primary OA refers to the spectrum of degenerative joint diseases for which no underlying etiology has been determined. Typically, the joint affected by primary OA are the interphalangeal joints of the hands, the first carpometacarpal joints, the hips, the knees, the spine, and some joints in the midfoot. Interestingly, it appears that large joints, such as the ankles, elbows and shoulders tend to be spared in primary OA. In contrast, secondary OA often occurs as a result of defined injury or trauma. Secondary arthritis can also be found in individuals with metabolic diseases such as hemochromatosis and alkaptonuria, developmental abnormalities such as developmental dysplasia of the hips (congenital dislocation of the hips) and limb-length discrepancies, obesity, inflammatory arthritides such as rheumatoid arthritis or gout, septic arthritis, and neuropathic arthritis.

OA is a progressive, degenerative disorder. The degradation associated with OA initially appears as fraying and fibrillation of the articular cartilage surface as proteoglycans are lost from the matrix. With continued joint use, surface fibrillation progresses, defects penetrate deeper into the cartilage, and pieces of cartilage tissue are lost. In addition, bone underlying the cartilage (subchondral bone) thickens, and, as cartilage is lost, bone becomes slowly exposed. With asymmetric cartilage destruction, disfigurement can occur. Bony nodules, called osteophytes, often form at the periphery of the cartilage surface and occasionally grow over the adjacent eroded areas. If the surface of these bony outgrowths is permeated, vascular outgrowth may occur and cause the formation of tissue plugs containing fibrocartilage.

Since cartilage is avascular, damage which occurs to the cartilage layer but does not penetrate to the subchondral bone, leaves the job of repair to the resident chondrocytes, which have little intrinsic potential for replication. However, when the subchondral bone is penetrated, its vascular supply allows a triphasic repair process to take place. The suboptimal cartilage which is synthesized in response to this type of damage, termed herein "fibrocartilage" because of its fibrous matrix, has suboptimal biochemical and mechanical properties, and is thus subject to further wear and destruction. In a diseased or damaged joint, increased release of metalloproteinases (MMPs) such as collagenases, gelatinases, stromelysins, aggrecanases, and other proteases, leads to further thinning and loss of cartilage. In vitro studies have shown that cytokines such as IL-1$\alpha$, IL-1$\beta$, TNF-$\alpha$, PDGF, GM-CSF, IFN-$\gamma$, TGF-$\beta$, LIF, IL-2 and IL-6, IL-8 can alter the activity of synovial fibroblast-like cells, macrophage, T cells, and/or osteoclasts, suggesting that these cytokines may regulate cartilage matrix turnover in vivo. As such, any of these cytokines could amplify and perpetuate the destructive cycle of joint degeneration in vivo. In fact, inhibition of IL-1 or TNF-$\alpha$ activity in arthritic animals and humans has been shown to be an effective way in which to at least slow the progression of arthritis. While the initiating events in RA and OA are clearly different, subsequent cartilage and bone loss in these two degenerative disorders appears to involve many of the same cytokines and proteinases.

The mechanical properties of cartilage are determined by its biochemical composition. While the collagen architecture contributes to the tensile strength and stiffness of cartilage, the compressibility (or elasticity) is due to its proteoglycan component. In healthy articular cartilage, type II collagen predominates (comprising about 90-95%), however, smaller amounts of types V, VI, IX, and XI collagen are also present. Cartilage proteoglycans (PG) include hydrodynamically large, aggregating PG, with covalently linked sulfated glycosaminoglycans, as well as hydrodynamically smaller non-aggregating PG such as decorin, biglycan and lumican.

Types of Injuries to Cartilage

Injuries to cartilage fall into three categories: (1) microdamage or blunt trauma, (2) chondral fractures, and (3) osteochondral fractures.

Microdamage to chondrocytes and cartilage matrix may be caused by a single impact, through repetitive blunt trauma, or with continuous use of a biomechanically unstable joint. In fact, metabolic and biochemical changes such as those found in the early stages of degenerative arthritis can be replicated in animal models involving repetitive loading of articular cartilage. Radin et al., *Clin. Orthop. Relat. Res.* 131: 288-93 (1978). Such experiments, along with the distinct pattern of cartilage loss found in arthritic joints, highlight the role that biomechanical loading plays in the loss of homeostasis and integrity of articular cartilage in disease. Radin et al., *J Orthop Res.* 2: 221-234 (1984); Radin et al., *Semin Arthritis Rheum* (suppl. 2) 21: 12-21 (1991); Wei et al., *Acta Orthop Scand* 69: 351-357 (1998). While chondrocytes may initially be able to replenish cartilage matrix with proteoglycans at a basal rate, concurrent damage to the collagen network may increase the rate of loss and result in irreversible degeneration. Buckwalter et al., *J. Am. Acad. Orthop. Surg.* 2: 192-201 (1994).

Chondral fractures are characterized by disruption of the articular surface without violation of the subchondral plate. Chondrocyte necrosis at the injury site occurs, followed by increased mitotic and metabolic activity of the surviving chondrocytes bordering the injury which leads to lining of the clefts of the articular surface with fibrous tissue. The increase in chondrocyte activity is transitory, and the repair response results in insufficient amount and quality of new matrix components.

Osteochondral fractures, the most serious of the three types of injuries, are lesions crossing the tidemark into the underlying subchondral plate. In this type of injury, the presence of subchondral vasculature elicits the three-phase response typically encountered in vascular tissues: (1) necrosis, (2) inflammation, and (3) repair. Initially the lesion fills with blood and clots. The resulting fibrin clot activates an inflammatory response and becomes vascularized repair tissue, and the various cellular components release growth factors and cytokines including transforming growth factor beta (TGF-beta), platelet-derived growth factor (PDGF), bone morphogenic proteins, and insulin-like growth factors I and II. Buckwalter et al., *J. Am. Acad. Orthop. Surg.* 2: 191-201 (1994).

The initial repair response associated with osteochondral fractures is characterized by recruitment, proliferation and differentiation of precursors into chondrocytes. Mesenchymal stem cells are deposited in the fibrin network, which eventually becomes a fibrocartilaginous zone. F. Shapiro et al., *J. Bone Joint Surg.* 75: 532-53 (1993); N. Mitchell and N. Shepard, *J. Bone Joint Surg.* 58: 230-33 (1976). These stem cells, which are believed to come from the underlying bone marrow rather than the adjacent articular surface, progressively differentiate into chondrocytes. At six to eight weeks after injury, the repair tissue contains chondrocyte-like cells in a matrix of proteoglycans and predominantly type II collagen, with some type I collagen. T. Furukawa et al., *J. Bone Joint Surg.* 62: 79-89 (1980); J. Cheung et al., *Arthritis Rheum.* 23: 211-19 (1980); S. O. Hjertquist & R. Lemperg, *Calc. Tissue Res.* 8: 54-72 (1971). However, this newly deposited matrix degenerates, and the chondroid tissue is replaced by more fibrous tissue and fibrocartilage and a shift in the synthesis of collagen from type II to type I. H. S. Cheung et al., *J. Bone Joint Surg.* 60: 1076-81 (1978); D. Hamerman, "Prospects for medical intervention in cartilage repair," *Joint cartilage degradation: Basic and clinical aspects*, Eds. Woessner J F et al., (1993); Shapiro et al., *J. Bone Joint Surg.* 75: 532-53 (1993); N. Mitchell & N. Shepard, *J. Bone Joint Surg.* 58: 230-33 (1976); S. O.

Hjertquist & R. Lemperg, *Calc. Tissue Res.* 8: 54-72 (1971). Early degenerative changes include surface fibrillation, depletion of proteoglycans, chondrocyte cloning and death, and vertical fissuring from the superficial to deep layers. At one year post-injury, the repair tissue is a mixture of fibrocartilage and hyaline cartilage, with a substantial amount of type I collagen, which is not found in appreciable amounts in normal articular cartilage. T. Furukawa, et al., *J. Bone Joint Surg.* 62: 79-89 (1980).

From a clinical viewpoint, the fibrocartilaginous repair tissue may function satisfactorily for a certain length of time. However, fibrocartilage has inferior biomechanical properties relative to that of normal hyaline cartilage. Collagen fibers are arrayed in a random orientation with a lower elastic modulus in fibrocartilage than in normal hyaline cartilage. J. Colletti et al., *J. Bone Joint Surg.* 54: 147-60 (1972). The permeability of the repair tissue is also elevated, thus reducing the fluid-pressure load-carrying capacity of the tissue. H. Mankin et al., "Form and Function of Articular Cartilage", *Orthopaedic Basic Science*, Ed: Simon & Schuster, American Academy of Orthopeadic Surgeons, Rosemont, Ill. (1994). These changes result in increased viscoelastic deformation, making the repair tissue less able to withstand repetitive loading than normal articular cartilage. Glycosaminoglycan (GAG) levels in the cartilage adjacent to osteochondral defects have been reported to be reduced by 42% of normal values, indicating that injury leads to degeneration beyond the initial defect. *Osteoarthritis Cartilage* 3: 61-70 (1995).

Chondrocyte Transplantation and Survival

The transplantation of chondrocytes, the cells responsible for secreting cartilage matrix, has also been suggested as a means of effecting cartilage repair. However, the disadvantages of allografts e.g. the possibility of the host's immunogenic response as well as the transmission of viral and other infectious diseases, has effectively limited the scope of allogenic chondrocyte transplantation. Although these risks can be minimized by using the patient's own tissue or cells, this procedure requires further surgery, creation of a new lesion in the patient's cartilage, and expensive culturing and growing of patient-specific cells.

When cultured as monolayers on tissue culture dishes, isolated chondrocytes will de-differentiate, and with time in culture, come to resemble fibroblasts. For example, collagen production will switch from predominantly type II to type I, and cells will synthesize an increased proportion of hyaluronic acid relative to the total glycosaminoglycan (GAG) content. W. Green, *Clin. Orthop. Relat. Res.* 124: 237-50 (1977). However, chondrocytes grown in collagen gels or as aggregate cultures will maintain normal morphology, proteoglycan and type II collagen synthesis as well as and retain their ability to accumulate metachromatic matrix in vitro. Thus, under these conditions, chondocytes will remain relatively differentiated and phenotypically stable for up to several weeks in vitro. T. Kimura et al., *Clin. Orthop. Relat. Res.* 186: 231-39 (1984).

Tissue Engineering:

The difficulties and expense associated with the culturing of chondrocytes has led to the design of chondrocyte-seeded or cell-free implants for articular cartilage repair using a variety of biomaterials, including: demineralized or enzymatically treated bone, L. Dahlberg. et al., *J. Orthop. Res.* 9: 11-19 (1991); B. C. Toolan et al., *J. Biotned. Mat. Res.* 41: 244-50 (1998); C. R., Chu et al., *J. Biomed. Mat. Res.* 29: 1147-54 (1995); polyglycolic acid C. A. Vacanti et al., *Mat. Res. Soc. Symp. Proc.* 252: 367-74 (1992); hydroxyapaptite/Dacron composites, K. Messner & J. Giliquist, *Biomaterials* 14: 513-21 (1993); fibrin, D. A. Hendrickson et al., *J. Orthop. Res.* 12: 485-97 (1994); collagen gels, D. Grande et al., *J. Orthop. Res.* 7: 208-18 (1989), S. Wakitani et al., *J. Bone Joint Surg.* 71: 74-80 (1989), S. Wakitani et al., *J. Bone Joint Surg.* 76: 579-92 (1994); and collagen fibers, J. M. Pachence et al., "Development of a tissue analog for cartilage repair," *Tissue inducing biomaterials*, Eds, L. Cima & E. Ron, Materials Research Soc. Press., Pittsburgh, Pa. (1992); B. C. Toolan et al., *J. Biomed. Mat. Res.* 31: 273-80 (1996). Alternative tissues employed include synovial tissue, A. G. Rothwell, *Orthopedics* 13: 433-42 (1990); or tissues rich in mesenchymal stem cells (e.g., bone marrow or periosteal tissue), K. Messner & J. Gillquist, *Mat. Res. Soc. Symp. Proc.* 252: 367-74 (1992).

Standard Cartilage Surgical Techniques:

The present method may also be administered in combination with any standard cartilage surgical technique. Standard surgical techniques are surgical procedures which are commonly employed for therapeutic manipulations of cartilage, including: cartilage shaving, abrasion chondroplasty, laser repair, debridement, chondroplasty, microfracture with or without subchondral bone penetration, mosaicplasty, cartilage cell allografts, stem cell autografts, costal cartilage grafts, chemical stimulation, electrical stimulation, perichondral autografts, periosteal autografts, cartilage scaffolds, shell (osteoarticular) autografts or allografts, or osteotomy. These techniques are described and discussed in greater detail in Frenkel et al., *Front. Bioscience* 4: d671-685 (1999).

Cartilage Agents:

In combination with or in lieu of tissue engineering, the administration of cartilage agents (e.g., peptide growth factors) has been considered as a way to augment cartilage repair. Cartilage agents are very significant regulators of cartilage cell differentiation, migration, adhesion, and metabolism. F. S. Chen et al., *Am J. Orthop.* 26: 396-406 (1997). Because cartilage agents are soluble proteins of relative small molecular mass and are rapidly absorbed and/or degraded, a great challenge exists in making them available to cells in sufficient quantity and for sufficient duration. Secreted proteins may thus need to be incorporated into engineered, implantable devices for maximum effectiveness. The ideal delivery vehicle is biocompatible, resorbable, has the appropriate mechanical properties, and degrades into non-toxic by-products.

Several secreted peptides have the potential to induce host cartilage repair without transplantation of cells. Insulin-like growth factor (IGF-1) stimulates both matrix synthesis and cell proliferation in culture, K. Osborn. *J. Orthop. Res.* 7: 35-42 (1989), and insufficiency of IGF-1 may have an etiologic role in the development of osteoarthritis. R. D. Coutts, et al., *Instructional Course Lect.* 47: 487-94, Amer. Acad. Orthop. Surg. Rosemont, Ill. (1997). Some studies indicate that serum IGF-1 concentrations are lower in osteoarthritic patients than control groups, while other studies have found no difference. Nevertheless, both serum IGF-1 levels and chondrocyte responsiveness to IGF-1 decrease with age. J. R. Florini & S. B. Roberts, *J. Gerontol.* 35: 23-30 (1980). Thus, both the decreased availability of IGF-1 as well as diminished chondrocyte responsiveness to IGF-1 may contribute to cartilage homeostasis and lead to degeneration with advancing age.

IGF-1 has been proposed for the treatment of prevention of osteoarthritis. In fact, intra-articular administration of IGF-1 in combination with sodium pentosan polysulfate (a chondrocyte catabolic activity inhibitor) caused improved histological appearance, and near-normal levels of degradative enzymes (neutral metalloproteinases and collagenase), tissue inhibitors of metalloproteinase and matrix collagen. R. A. Rogachefsky, et al., *Ann. NY Acad. Sci.* 732: 889-95 (1994). The use of IGF-1 either alone or as an adjuvant with other growth factors to stimulate cartilage regeneration has been described in WO 91/19510, WO 92/13565, U.S. Pat. No. 5,444,047, EP 434,652, Bone morphogenetic proteins (BMPs) are members of the large transforming growth factor beta (TGF-β) family of growth factors. In vitro and in vivo studies have shown that BMP induces the differentiation of mesenchymal cells into chondrocytes. K. Sato & M. Urist, *Clin. Orthop. Relat. Res.* 183: 180-87 (1984). Furthermore, skeletal growth factor and cartilage-derived growth factors have synergistic effects with BMP, as the combination of these growth factors with BMP and growth hormone initiates mesenchymal cell differentiation. Subsequent proliferation of the differentiated cells are stimulated by other factors. D. J. Hill & A Logan, *Prog. Growth Fac. Res.* 4: 45-68 (1992).

Transforming growth factor beta (TGF-β) is produced by osteoblasts, chondrocytes, platelets, activated lymphocytes, and other cells. R. D. Coutts et al., supra. TGF-β can have both stimulatory and inhibitory properties on matrix synthesis and cell proliferation depending on the target cell, dosage, and cell culture conditions. P. Guerne et al., *J. Cell Physiol.* 158: 476-84 (1994); H. Van Beuningen et al., *Ann. Rheum. Dis.* 52: 185-91 (1993); P. Van der Kraan et al., *Ann. Rheum. Dis.* 51: 643-47 (1992). Furthermore, as with IGF-1, TGF-β, responsiveness is decreased with age. P. Guerne et al., *J. Cell Physiol.* 158: 476-84 (1994). However, TGF-β is a more potent stimulator of chondrocyte proliferation than other growth factors, including platelet-derived growth factor (PDGF), bFGF, and IGF-1 (Guerne et al., supra), and can stimulate proteoglycan production by chondrocytes. TGF-β also down-regulates the effects of cytokines which stimulate chondrocyte catabolism Van der Kraan et al., supra. In vivo, TGF-β induces proliferation and differentiation of mesenchymal cells into chondrocytes and enhances repair of partial-thickness defects in rabbit articular cartilage. E. B. Hunziker & L. Rosenberg, *Trans. Orthopaed. Res. Soc.* 19: 236 (1994).

Antagonism of Cartilage Catabolism

Cartilage matrix degradation is believed to be due to cleavage of matrix molecules (proteoglycans and collagens) by proteases (reviewed in Woessner J F Jr., "Proteases of the extracellular matrix", in Mow, V., Ratcliffe, A. (eds): *Structure and Function of Articular Cartilage*. Boca Raton, Fla., CRC Press, 1994 and Smith R. L., *Front. In Biosci.* 4:d704-712. While the key enzymes involved in matrix breakdown have not yet been clearly identified, matrix metalloproteinases (MMPs) and "aggrecanases" appear to play key roles in joint destruction. In addition, members of the serine and cysteine family of proteinases (for example the cathepsins and urokinase or tissue plasminogen activator (uPA and tPA)) may also be involved. Plasmin, urokinase plasminogen activator (uPA) and tissue plasminogen activator (tPA may play an important role in the activation pathway of the metalloproteinases. Evidence connects the closely related group of cathepsin B, L and S to matrix breakdown, and these cathepsins are somewhat increased in OA. Many cytokines, including IL-1, TNF-α and LIF induce MMP expression in chondrocytes. Induction of MMPs can be antagonized by TGF-β and 1L-4 and potentiated, at least in rabbits, by FGF and PDGF. As shown by animal studies, inhibitors of these proteases (MMPs and aggrecanases) may at least partially protect joint tissue from damage in vivo.

Other methods of stimulating cartilage repair include blocking the effects of molecules which are associated with cartilage destruction. For example, both IL-1 (α and β) and nitric oxide are substances with known catabolic effects on cartilage. The cytokine IL-1 causes cartilage breakdown, including the generation of synovial inflammation and up-regulation of matrix metalloproteinases and aggrecanases. V. Baragi, et al., *J. Clin. Invest.* 96: 2454-60 (1995); V. M. Baragi et al., *Osteoarthritis Cartilage* 5: 275-82 (1997); C. H. Evans et al., *J. Leukoc. Biol.* 64: 55-61 (1998); C. H Evans and P. D. Robbins, *J. Rheumatol.* 24: 2061-63 (1997); R. Kang et al., *Biochem. Soc. Trans.* 25: 533-37 (1997); R. Kang et al., *Osteoarthritis Cartilage* 5: 13943 (1997). Because high levels of IL-1 are found in diseased joints and IL-1 is believed to play a pivotal role in initiation and development of arthritis, inhibition of IL-1 activity may prove to be a successful therapy. In mammals only one protease, named interleukin 1β-convertase (ICE), can specifically generate mature, active IL-1β. Inhibition of ICE has been shown to block IL-1β production and may slow arthritic degeneration (reviewed in Martel-Pelletier J. et al. *Front. Biosci.* 4: d694-703). The soluble IL-1 receptor antagonist (IL-1ra), a naturally occurring protein that can inhibit the effects of IL-1 by preventing IL-1 from interacting with chondrocytes, has also been shown to be effective in animal models of arthritis and is currently being tested in humans for its ability to prevent the incidence or progression of arthritis.

Nitric oxide (NO) plays a substantial role in the destruction of cartilage. Ashok et al., *Curr. Opin. Rheum.* 10: 263-268 (1998). Unlike normal cartilage which does not produce NO unless stimulated with cytokines such as IL-1α, cartilage obtained from osteoarthritic joints produces large amounts of nitric oxide for over 3 days in culture despite the absence of added stimuli. Moreover, inhibition of NO production has been shown to prevent IL-1α mediated cartilage destruction and chondrocyte death as well as progression of osteoarthritis in animal models. Thus, inhibition of NO may be one way to prevent cartilage destruction.

As with IL1α and β, TNF-α is synthesized by chondrocytes, induces matrix breakdown, inhibits matrix synthesis, and is found at high levels in arthritic joints. TNF-α also synergizes with IL-1 in terms of cartilage destruction. Inhibition of TNF-α activity, in arthritic animals and humans has been shown to inhibit progression of arthritis.

Leukemia inhibitory factor (LIF), which is synthesized by both cartilage and synovium, is present in human synovial fluids. Because LIF induces the synthesis of matrix metalloproteinases (MMPs) by chondrocyte, it may be involved in the breakdown of the cartilaginous matrix.

Interferon-gamma (IFN-γ) inhibits proteoglycan synthesis by human chondrocytes without enhancing its breakdown. Indeed, IFN-γ may suppress proteoglycan loss by inhibiting the induction of MMPs.

Interleukin 8, a potent chemotactic cytokine for polymorphonuclear neutrophils (PMN), is synthesized by a variety of cells including monocytes/macrophages, chondrocytes and fibroblasts and is induced by TNF-α. In OA patients, IL-β, IL-6, TNF-α and IL-8 are all found in the synovial fluid. IL-8 can enhance the release of inflammatory cytokines in human mononuclear cells, including that of IL-1β, IL-6 and TNF-α, which may further modulate the inflammatory reaction (reviewed in Martel-Pelletier J. et al., *Front. Biosci.* 4: d694-703).

IL-6 has also been proposed as a contributor to the OA pathological process by increasing inflammatory cells in the synovial tissue and by stimulating the proliferation of chondrocytes. In addition, IL-6 can amplify the effects of IL-1 on MMP synthesis and inhibition of proteoglycan production (reviewed in Martel-Pelletier J. et al. *Front. Biosci.* 4: d694-703).

Interleukin 17 upregulates production of IL-1β, TNF-α, IL-6 and MMPs in human macrophages. IL-17 also induces NO production in chondrocytes, and is expressed in arthritic, but not normal joints (reviewed in Martel-Pelletier J. et al. *Front. Biosci.* 4: d694-703).

Basic fibroblast growth factor (bFGF), which is synthesized by chondrocytes, can induce articular chondrocyte replication. B. C. Toolan et al., *J. Biomed. Mat. Res.* 41: 244-50 (1998). In explants taken from young animals, bFGF in small amounts (e.g., 3 ng/ml) stimulates synthesis and inhibits breakdown of proteoglycans, while higher levels (e.g., 30-300 ng/ml) has exactly the opposite effect (i.e., synthesis inhibition and enhanced breakdown). In adult tissues, higher doses of FGF stimulated proteoglycan, protein and collagen synthesis with no cell proliferation. R. L. Sah et al., *Arch. Biochem. Biophys.* 308: 137-47 (1994). bFGF also regulates cartilage homeostasis by inducing the autocrine release from chondrocytes of interleukin 1 (IL-1), a potent stimulator of catabolic behavior in cartilage. bFGF further enhances IL-1-mediated protease release, perhaps through its ability to upregulate IL-1 receptors on chondrocytes. J. E. Chin et al., *Arthritis Rheum.* 34: 314-24 (1991)]. Similarly, platelet-derived growth factor (PDGF) can potentiate the catabolic effects of IL-1 and presumably of TNF-α. However, some evidence suggests that in human cartilage bFGF and PDGF may have an anticatabolic effect; whether this phenomenon is species-specific or an effect of age remains to be determined.

While inflammation does not appear to be the initiating even in osteoarthritis, inflammation does occur in osteoarthritic joints. The inflammatory cells (i.e. monocytes, macrophages, and neutrophils) which invade the synovial lining after injury and during inflammation produce metalloproteinases as well as catabolic cyokines which can contribute to further release of degradative enzymes. Although inflammation and joint destruction do not show perfect correlation in all animal models of arthritis, agents such as IL-4, IL-10 and IL-13 which inhibit inflammation also decrease cartilage and bone pathology in arthritic animals (reviewed in Martel-Pelletier J. et al. *Front. Biosci.* 4: d694-703). Application of agents which inhibit inflammatory cytokines may slow OA progression by countering the local synovitis which occurs in OA patients.

Numerous studies show that members of the tetracycline family of antibiotics are effective in inhibiting collagenase and gelatinase activity. Oral administration of one of these, doxycycline, proved to decrease both collagenase and gelatinase activity in cartilage from endstage hip osteoarthritis. These data suggest that an effective oral dose of doxycycline may slow down progression of osteoarthritis. Smith R. L. *Front. Biosci.* 4: d704-712.

OA involves not only the degeneration of articular cartilage leading to eburnation of bone, but also extensive remodelling of subchondral bone resulting in the so-called sclerosis of this tissue. These bony changes are often accompanied by the formation of subchondral cysts as a result of focal resorption. Agents which inhibit bone resorption, i.e. osteoprotegerin or bisphosphonates have shown promising results in animal model of arthritis. Kong et al. *Nature* 402: 304-308.

I. Definitions

The term "cartilaginous disorder" refers to a collection of diseases which are further manifested by symptoms of pain, stiffness and/or limitation of motion of the affected body parts, including that which results for disease or injury. Included within the scope of "cartilaginous disorders" is "degenerative cartilaginous disorders"—a collection of disorders characterized, at least in part, by degeneration or metabolic derangement of connective tissues of the body, including not only the joints or related structures, including muscles, bursae (synovial membrane), tendons and fibrous tissue, but also the growth plate. In one embodiment, the term includes "articular cartilage disorders" which are characterized by disruption of the smooth articular cartilage surface and degradation of the cartilage matrix. Additional pathologies include nitric oxide production, and inhibition or reduction of matrix synthesis.

Included within the scope of "articular cartilage disorder" are osteoarthritis (OA) and rheumatoid arthritis (RA). OA defines not a single disorder, but the final common pathway of joint destruction resulting from multiple processes. OA is characterized by localized asymmetric destruction of the cartilage commensurate with palpable bony enlargements at the joint margins. OA typically affects the interphalangeal joints of the hands, the first carpometacarpal joint, the hips, the knees, the spine, and some joints in the midfoot, while large joints, such as the ankles, elbows and shoulders tend to be spared. OA can be associated with metabolic diseases such as hemochromatosis and alkaptonuria, developmental abnormalities such as developmental dysplasia of the hips (congenital dislocation of the hips), limb-length discrepancies, including trauma and inflammatory arthritides such as gout, septic arthritis, neuropathic arthritis. OA may also develop after extended biomechanical instability, such as that resulting from sports injury or obesity.

Rheumatoid arthritis (RA) is a systemic, chronic, autoimmune disorder characterized by symmetrical synovitis of the joint and typically affects small and large diarthroid joints alike. As RA progresses, symptoms may include fever, weight loss, thinning of the skin, multiorgan involvement, scieritis, corneal ulcers, the formation of subcutaneous or subperiosteal nodules and even premature death. The symptoms of RA often appear during youth and can include vasculitis, atrophy of the skin and muscle, subcutaneous nodules, lymphadenopathy, splenomegaly, leukopaenia and chronic anaemia.

Furthermore, the term "degenerative cartilaginous disorder" may include systemic lupus erythematosus and gout, amyloidosis or Felty's syndrome. Additionally, the term covers the cartilage degradation and destruction associated with psoriatic arthritis, osteoarthrosis, acute inflammation (e.g., yersinia arthritis, pyrophosphate arthritis, gout arthritis (arthritis urica), septic arthritis), arthritis associated with trauma, inflammatory bowel disease (e.g., Crohn's disease, ulcerative colitis, regional enteritis, distal ileitis, granulomatous enteritis, regional ileitis, terminal ileitis), multiple sclerosis, diabetes (e.g., insulin-dependent and non-insulin dependent), obesity, giant cell arthritis and Sjögren's syndrome.

Examples of other immune and inflammatory diseases, at least some of which may be treatable by the methods of the invention include, juvenile chronic arthritis, spondyloarthropathies, systemic sclerosis (scleroderma), idiopathic inflammatory myopathies (dermatomyositis, polymyositis), systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis) autoimmune inflammatory diseases (e.g., allergic encephalomyelitis, multiple sclerosis, insulin-dependent diabetes mellitus, autoimmune uveoretinitis, thyrotoxicosis, autoimmune thyroid disease, pernicious anemia) and allograft rejection, diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases including viral diseases such as AIDS (HIV infection), herpes, etc., bacterial infections, fungal infections, protozoal infections, parasitic infections, and respiratory syncytial virus, human immunodeficiency virus, etc.) and allergic disorders, such as anaphylactic hypersensitivity, asthma, allergic rhinitis, atopic dermatitis, vernal conjunctivitis, eczema, urticaria and food allergies, etc.

"Treatment" is an intervention performed with the intention of preventing the development or altering the pathology of a disorder. Accordingly, "treatment" refers to both therapeutic treatment and prophylactic or preventative measures, wherein the object is to prevent or slow down (lessen) the targeted pathological condition or disorder. Those in need of treatment include those already with the disorder as well as those in which the disorder is to be prevented. In treatment of a cartilaginous disorder, a therapeutic agent may directly decrease or increase the magnitude of response of a pathological component of the disorder, or render the disease more susceptible to treatment by other therapeutic agents, e.g. antibiotics, antifungals, anti-inflammatory agents, chemotherapeutics, etc.

The term "effective amount" is the minimum concentration of insulin and/or variant thereof which causes, induces or results in either a detectable improvement or repair in damaged cartilage or a measureable protection from the continued or induced cartilage destruction in an isolated sample of cartilage matrix (e.g., retention of proteoglycans in matrix, inhibition of proteoglycan release from matrix, stimulation of proteoglycan synthesis). Furthermore a "therapeutically effective amount" is the minimum concentration (amount) of insulin and/or variant thereof administered to a mammal which would be effective in at least attenuating a pathological symptom (e.g. causing, inducing or resulting in either a detectable improvement or repair in damaged articular cartilage or causing, inducing or resulting in a measureable protection from the continued or initial cartilage destruction, improvement in range of motion, reduction in pain, etc.) which occurs as a result of injury or a cartilaginous disorder.

"Cartilage agent" may be a growth factor, cytokine, small molecule, antibody, piece of RNA or DNA, virus particle, peptide, or chemical having a beneficial effect upon cartilage, including peptide growth factors, catabolism antagonists and osteo-, synovial- or anti-inflammatory factors. Alternatively, "cartilage agent" may be a peptide growth factor—such as any of the fibroblast growth factors (e.g., FGF-1, FGF-2, . . . FGF-21, etc.), IGF's (I and II), TGF-βs (1-3), BMPs (1-7), or members of the epidermal growth factor family such as EGF, HB-EGF, TGF-α—which could enhance the intrinsic reparative response of cartilage, for example by altering proliferation, differentiation, migration, adhesion, or matrix production by chondrocytes. Alternatively, a "cartilage agent" may be a factor which antagonizes the catabolism of cartilage (e.g., IL-1 receptor antagonist (IL-1ra), NO inhibitors, IL1-β convertase (ICE) inhibitors, factors which inhibit activity of IL-6, IL-8, LIF, IFNγ, TNF-α activity, tetracyclines and variants thereof, inhibitors of apoptosis, MMP inhibitors, aggrecanase inhibitors, inhibitors of serine and cysteine proteinases such as cathepsins and urokinase or tissue plasminogen activator (uPA and tPA). Alternatively still, cartilage agent includes factors which act indirectly on cartilage by affecting the underlying bone (i.e., osteofactors, e.g. bisphosphonates or osteoprotegerin) or the surrounding synovium (i.e., synovial factors) or anti-inflammatory factors (e.g., anti-TNF-α, IL1ra, IL-4, IL-10, IL-13, NSAIDs). For a review of cartilage agent examples, please see Martel-Pelletier et al., *Front. Biosci.* 4: d694-703 (1999); Hering, T. M., *Front. Biosci.* 4: d743-761 (1999).

"Standard surgical techniques" are surgical procedures which are commonly employed for therapeutic manipulations of cartilage, including: cartilage shaving, abrasion chondroplasty, laser repair, debridement, chondroplasty, microfracture with or without subchondral bone penetration, mosaicplasty, cartilage cell allografts, stem cell autografts, costal cartilage grafts, chemical stimulation, electrical stimulation, perichondral autografts, periosteal autografts, cartilage scaffolds, shell (osteoarticular) autografts or allografts, or osteotomy. These techniques are reviewed and described in better detail in Frenkel et al., *Front. Bioscience* 4: d671-685 (1999).

An "IGFBP" or an "IGF binding protein" refers to a protein or polypeptide normally associated with or bound or complexed to IGF-1 or IGF-2, whether or not it is circulatory (ie., in serum or tissue). Such binding proteins do not include receptors. This definition includes IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs. Mac 25 is described, for example, in Swisshelm et al., *Proc. Natl. Acad. Sci. USA,* 92: 4472-4476 (1995) and Oh et al., *J. Biol. Chem.,* 271: 30322-30325 (1996). PSF is described in Yamauchi et al., *Biochem. J.,* 303: 591-598 (1994). ESM-1 is described in Lassalle et al., *J. Biol. Chem.,* 271: 20458-20464 (1996). For other identified IGFBPs, see, e.g., EP 375,438 published 27 Jun. 1990; EP 369,943 published 23 May 1990; WO 89/09268 published 5 Oct. 1989; Wood et al., *Molec. Endocrin.,* 2: 1176-1185 (1988); Brinkman et al., *The EMBO J.,* 7: 2417-2423 (1988); Lee et al., *Mol. Endocrinol.,* 2: 404-411 (1988); Brewer et al., *BBRC,* 152: 1289-1297 (1988); EP 294,021 published 7 Dec. 1988; Baxter et al., *BBRC,* 147: 408-415 (1987); Leung et al., *Nature,* 330: 537-543 (1987); Martin et al., *J. Biol. Chem.,* 261: 8754-8760 (1986); Baxter et al., *Comp. Biochem. Physiol.,* 91B: 229-235 (1988); WO 89/08667 published 21 Sep. 1989; WO 89/09792 published 19 Oct. 1989; and Binkert et al., *EMBO J.,* 8: 2497-2502 (1989).

"Chronic" administration refers to administration of the factor(s) in a continuous mode as opposed to an acute mode, so as to maintain the initial therapeutic effect (activity) for an extended period of time. "Intermittent" administration is treatment that is done not consecutively without interruption, but rather is cyclic in nature.

The "pathology" of a cartilaginous disorder includes any physiological phenomena that compromise the well-being of the patient. This includes, without limitation, cartilage destruction, diminished cartilage repair, abnormal or uncontrollable cell growth or differentiation, antibody production, auto-antibody production, complement production and activation, interference with the normal functioning of neighboring cells, production of cytokines or other secretory products at abnormal levels, suppression or aggravation of any inflammatory or immunological response, infiltration of inflammatory cells (neutrophilic, eosinophilic, monocytic, lymphocytic) into tissue spaces, induction of pain, or any tissue effect which results in impairment of joint function or mobility etc.

"Mammal" for purposes of treatment refers to any animal classified as a mammal, including humans, domestic and farm animals, and zoo, sports, or pet animals, such as dogs, horses, cats, cattle, pigs, hamsters, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®, hyaluronic acid (HA).

The term "insulin" and/or "insulin variant" when used herein encompass both (1) native sequence insulin and (2) insulin variants (which are further defined herein). The insulin molecule may be isolated from a variety of sources, such as from human tissue types or from another source, or prepared by recombinant and/or synthetic methods.

A "native sequence insulin" comprises a polypeptide having the same amino acid sequence as insulin derived from nature. Such native sequence insulin polypeptide can be isolated from nature or can be produced by recombinant and/or synthetic means. The term "native sequence insulin" specifically encompasses naturally-occurring truncated or secreted forms (e.g., an extracellular domain sequence), naturally-occurring truncated forms (e.g., alternatively spliced forms) and naturally-occurring allelic variants of insulin. In one embodiment of the invention, the native sequence human insulin is a mature or full-length native sequence insulin comprising an alpha ($\alpha$) or A chain of amino acids 1 to 21 of SEQ ID NO: 1 and a beta or B ($\beta$) chain of amino acids 1 to 30 of SEQ ID NO:2.

"Insulin variant polypeptide" means an active insulin polypeptide as defined below having at least about 80% amino acid sequence identity with the amino acid sequence of: (a) residues 1 to 21 of the A-chain of the human insulin polypeptide shown in FIG. 18A (SEQ ID NO:1) in combination with residues 1 to 30 of the B-chain of the human insulin polypeptide shown in FIG. 18B (SEQ ID NO:2), or (b) another specifically derived fragment of the amino acid sequences shown in FIGS. 18A and 18B (SEQ ID NO:1-2), or as described herein. In addition, the secondary structure depicted in FIGS. 18A and 18B, namely the disulfide bonds between cysteine residues A6-A11, A7-B7 and A20-B19 are also believed necessary for activity, thus the scope of variants under this definitions should also drawn so as to preserve this secondary structure as much as possible.

Insulin variant polypeptides include, for instance, polypeptides wherein one or more amino acid residues are added, or deleted, at the N- and/or C-terminus, as well as within one or more internal domains, of the sequences shown in FIGS. 18A & 18B (SEQ ID NO:1-2). Ordinarily, an insulin variant polypeptide will have at least about 80% amino acid sequence identity, alternatively at least about 81% amino acids sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity, alternatively at least about 99% amino acid sequence identity with: (a) residues 1 to 21 of the A-chain of the human insulin polypeptide shown in FIG. 18A (SEQ ID NO:1) in combination with residues 1 to 30 of the B-chain of the human insulin polypeptide shown in FIG. 18B (SEQ ID NO:2), or (b) another specifically derived fragment of the amino acid sequences shown in FIGS. 18A and 18B (SEQ ID NO:1-2), or as described herein.

Insulin variant polypeptides have an A chain length of at least about 15 residues, alternatively at least about 16 residues, alternatively at least about 17 residues, alternatively at least about 18 residues, alternatively at least about 19 residues, alternatively at least about 20 residues, alternatively at least about 21 residues, alternatively at least about 22 residues, alternatively at least about 23 residues, alternatively at least about 24 residues, alternatively at least about 25 residues, alternatively at least about 26 residues, alternatively at least about 27 residues, alternatively at least about 28 residues, alternatively at least about 29 residues, alternatively at least about 30 residues, alternatively at least about 35 residues, or more. Insulin variant polypeptides have an B chain length of at least about 25 residues, alternatively at least about 26 residues, alternatively at least about 27 residues, alternatively at least about 28 residues, alternatively at least about 29 residues, alternatively at least about 29 residues, alternatively at least about 30 residues, alternatively at least about 31 residues, alternatively at least about 32 residues, alternatively at least about 33 residues, alternatively at least about 34 residues, alternatively at least about 35 residues, alternatively at least about 36 residues, alternatively at least about 37 residues, alternatively at least about 38 residues, alternatively at least about 39 residues, alternatively at least about 40 residues, alternatively at least about 41 residues, alternatively at least about 42 residues, alternatively at least about 42 residues, alternatively at least about 43 residues, alternatively at least about 44 residues, alternatively at least about 45 residues, alternatively at least about 50 residues.

The term "proinsulin" and/or "proinsulin variant" when used herein encompass both native sequence and proinsulin variants (which are further defined herein). The proinsulin molecule may be isolated from a variety of sources, such as from human tissue types or from another source, or prepared by recombinant and/or synthetic means.

A "native sequence proinsulin" comprises a polypeptide having the same amino acid sequence as a proinsulin derived from nature. Such native sequence insulin polypeptide can be isolated from nature or can be produced by recombinant and/or synthetic means. The term "native sequence proinsulin" specifically encompasses naturally-occurring truncated or secreted forms (e.g., an extracellular domain sequence), naturally-occurring truncated forms (e.g., alternatively spliced forms) and naturally-occurring allelic variants of insulin. In one embodiment of the invention, the native sequence human proinsulin is a mature or full-length native sequence insulin comprising residues 1 to 84 of FIG. 18C (SEQ ID NO:3). SEQ ID NO:3 contains three distinct segments: (1) a B-chain of residues 1 to 30 (SEQ ID NO:2); (2) a C-chain (connecting peptide) of residues 31-63 (SEQ ID NO:4) and an A chain of amino acids 64 to 84 (counting from the N-terminal side)(SEQ ID NO:1 ).

"Proinsulin variant" means an insulin precursor polypeptide capable of being processed into a mature insulin which is active, as defined below, comprising at least two distinct regions of contiguous residues; wherein one distinct region has at least about 80% amino acid sequence identity with the amino acid residues 1 to 21 of the A-chain of the human insulin polypeptide shown in FIG. 18A (SEQ ID NO:1), and the other distinct region has at least about 80% amino acid sequence identity with the amino in combination with the amino acid residues 1 to 30 of the B-chain of the human insulin polypeptide shown in FIG. 18B (SEQ ID NO:2), or (b) another specifically derived fragment of the amino acid sequences shown in FIGS. 18A and 18B (SEQ ID NO:1-2), or as described herein. Alternatively, a proinsulin variant will have at least 80% amino acid sequence identity, alternatively at least about with residues 1 to 110 of FIG. 18C (SEQ ID NO:3), or another specifically derived fragment of the amino acid sequences shown in FIG. 18C (SEQ ID NO:3). Additional regions may include a lengthened or abbreviated c-peptide and/or additional sequence 5'- or 3'- to the N-terminal and C-terminal residues, respectively, which provide for signaling and/or facilitate proper refolding into the mature active form.

In addition, the secondary structure depicted in FIGS. 18A and 18B, namely the disulfide bonds between cysteine residues A6-A11, A7-B7 and A20-B19 are also believed necessary for activity, thus the scope of variants under this definition should also drawn so as to preserve this secondary structure of the mature molecule as much as possible The length of proinsulin variants is the function of the length of the three main component parts, namely the A, B and C peptides. The length of the C-peptide can vary widely, from as few as no residues (i.e., deleted entirely) or as many as 50 peptide residues. The length of the A and B chain components of a proinsulin variant vary similarly as described previously for the full length molecule. Moreover, additional N-terminal sequence may be added for signaling purposes (e.g., to direct the translation product to the secretory pathway of the host cell) or to enhance or control expression (e.g., promoters, operons, etc.). The length of such N-terminal residues may comprise from 1 to 100 residues, including any integer contained within the range (i.e., 1, 2, 3 . . . 97, 98, 99, etc.).

"Percent (%) amino acid sequence identity" with respect to the polypeptide sequences identified herein is defined as the percentage of amino acid residues in a candidate sequence that are identical with the amino acid residues in a sequence of the insulin polypeptide, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2, wherein the complete source code for the ALIGN-2 program is provided in Table 1. The ALIGN-2 sequence comparison computer program was authored by Genentech, Inc. and the source code shown in Table 1 has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations, Table 2 and Table 3 demonstrate how to calculate the % amino acid sequence identity of the amino acid sequence designated "Comparison Protein" to the amino acid sequence designated "PRO".

Unless specifically stated otherwise, all % amino acid sequence identity values used herein are obtained as described above using the ALIGN-2 sequence comparison computer program. However, % amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from or otherwise obtained from the National Institutes of Health, Bethesda, Md., USA 20892. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Also included within the term "insulin variants" are polypeptides which in the context of the amino acid sequence identity comparisons performed as described above, include amino acid residues in the sequences compared that are not only identical, but also those that have similar properties. These polypeptides are termed "positives". Amino acid residues that score a positive value to an amino acid residue of interest are those that are either identical to the amino acid residue of interest or are a preferred substitution (as defined in Table 6 below) of the amino acid residue of interest. For purposes herein, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

"Insulin variant polynucleotide" or "Insulin variant nucleic acid sequence" means a nucleic acid molecule which encodes an active insulin polypeptide as defined below and which has at least about 80% nucleic acid sequence identity with a nucleic acid sequence which encodes: (a) amino acid residues 1-21 of the A-chain of the human insulin polypeptide shown in FIG. 18A (SEQ ID NO:1) in combination with residues 1 to 30 of the B-chain of the human insulin polypeptide shown (with substitution of the human residue B30Thr) in FIG. 18B (SEQ ID NO:2), or (b) a nucleic acid sequence which encodes another specifically derived fragment of the amino acid sequence shown in FIGS. 18A and B (SEQ ID NO:1-2). Ordinarily, an insulin variant polynucleotide will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with a nucleic acid sequence encoding amino acid residues: (a) amino acid residues 1-21 of the A-chain of the human insulin polypeptide shown in FIG. 18A (SEQ ID NO:1) in combination with residues 1 to 30 of the B-chain of the human insulin polypeptide shown (with substitution of the human residue B30Thr) in FIG. 18B (SEQ ID NO:2), or (b) a nucleic acid sequence which encodes another specifically derived fragment of the amino acid sequence shown in FIGS. 18 and B (SEQ ID NO:1-2).

Ordinarily, insulin variant polynucleotides contain nucleic acid encoding an A chain of insulin of at least about 45 nucleotides, alternatively at least about 48 nucleotides, alternatively at least about 51 nucleotides, alternatively at least about 54 nucleotides, alternatively at least about 57 nucleotides, alternatively at least about 60 nucleotides, alternatively at least about 63 nucleotides, alternatively at least about 66 nucleotides, alternatively at least about 69 nucleotides, alternatively at least about 72 nucleotides, alternatively at least about 75 nucleotides, alternatively at least about 78 nucleotides, alternatively at least about 81 nucleotides, alternatively at least about 84 nucleotides, alternatively at least about 87 nucleotides, alternatively at least about 90 nucleotides, alternatively at least about 105 nucleotides. Insulin variant polynucleotides contain nucleic acid encoding a B chain of insulin of at least about 75 nucleotides, alternatively at least about 78 nucleotides, alternatively at least about 81 nucleotides, alternatively at least about 84 nucleotides, alternatively at least about 87 nucleotides, alternatively at least about 90 nucleotides, alternatively at least about 93 nucleotides, alternatively at least about 96 nucleotides, alternatively at least about 99 nucleotides, alternatively at least about 102 nucleotides, alternatively at least about 105 nucleotides, alternatively at least about 108 nucleotides, alternatively at least about 111 nucleotides, alternatively at least about 114 nucleotides, alternatively at least about 117 nucleotides, alternatively at least about 120 nucleotides, alternatively at least about 123 nucleotides, alternatively at least about 126 nucleotides, alternatively at least about 129 nucleotides, alternatively at least about 132 nucleotides, alternatively at least about 135 nucleotides, alternatively at least about 150 nucleotides.

"Percent (%) nucleic acid sequence identity" with respect to the insulin polypeptide-encoding nucleic acid sequences identified herein is defined as the percentage of nucleotides in a candidate sequence that are identical with the nucleotides in an invention polypeptide-encoding sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine the appropriate parameters for measuring alignment, including any algorithms needed to achieve maximal alignment over the full-length of the sequences being compared. For purposes herein, however, % nucleic acid sequence identity values are obtained as described below by using the sequence comparison computer program ALIGN-2, wherein the complete source code for the ALIGN-2 program is provided in Table 1. The ALIGN-2 sequence comparison computer program was authored by Genentech, Inc. and the source code shown in Table 1 has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1. The ALIGN-2 program should be compiled for use on a UNIX operating system, preferably digital UNIX V4.0D. All sequence comparison parameters are set by the ALIGN-2 program and do not vary.

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5 demonstrate how to calculate the % nucleic acid sequence identity of the nucleic acid sequence designated "Comparison DNA" to the nucleic acid sequence designated "PRO-DNA".

Unless specifically stated otherwise, all % nucleic acid sequence identity values used herein are obtained as described above using the ALIGN-2 sequence comparison computer program. However, % nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from or otherwise obtained from the National Institutes of Health, Bethesda, Md. USA 20892. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, invention variant polynucleotides are nucleic acid molecules that encode an active polypeptide of the invention and which are capable of hybridizing, preferably under stringent hybridization and wash conditions, to nucleotide sequences encoding the full-length invention polypeptide. Invention variant polypeptides include those that are encoded by an invention variant polynucleotide.

The term "positives", in the context of the amino acid sequence identity comparisons performed as described above, includes amino acid residues in the sequences compared that are not only identical, but also those that have similar properties. Amino acid residues that score a positive value to an amino acid residue of interest are those that are either identical to the amino acid residues of interest or are a preferred substitution (as defined in Table 6 below) of the amino acid residue of interest.

For purposes herein, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 in that program's alignment of A and B, and where Y is the total number of amino acids residues in B. It will be appreciated that where the length of amino acid sequence A is not equal to the length of amino acid sequence B, the % positives of A to B will not equal the % positives of B to A.

An "isolated" nucleic acid molecule encoding a insulin or insulin variant polypeptide is a nucleic acid molecule that is identified and separated from at least one contaminant nucleic acid molecule with which it is ordinarily associated in the natural source of the insulin or insulin variant-encoding nucleic acid. Preferably, the isolated nucleic acid is free of association with all components with which it is naturally associated. An isolated insulin or insulin variant-encoding nucleic acid molecule is other than in the form or setting in which it is found in nature. Such isolated nucleic acid molecules therefore are distinguished from the insulin or insulin variant-encoding nucleic acid molecule as it exists in natural cells. However, an isolated nucleic acid molecule encoding an insulin or insulin variant polypeptide includes insulin or insulin variant-encoding nucleic acid molecules, respectively, contained in cells that ordinarily express such molecules where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 µg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a polypeptide of the invention fused to a "tag polypeptide". The tag polypeptide has enough residues to provide an epitope against which an antibody can be made, yet is short enough such that it does not interfere with the activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" in the context of variants of the polypeptide of the invention refers to form(s) of proteins of the invention which retain the biologic and/or immunologic activities of a native or naturally-occurring insulin polypeptide, wherein "biological" activity refers to a biological function (either inhibitory or stimulatory) caused by a native or naturally-occurring insulin other than the ability to serve as an antigen in the production of an antibody against an antigenic epitope possessed by a native or naturally-occurring polypeptide of the invention. Similarly, an "immunological" activity refers to the ability to serve as an antigen in the production of an antibody against an antigenic epitope possessed by a native or naturally-occurring polypeptide of the invention.

"Biological activity" in the context of an antibody or another molecule that can be identified by the screening assays disclosed herein (e.g. an organic or inorganic small molecule, peptide, etc.) is used to refer to the ability of such molecules to promote the regeneration of and/or prevent the destruction of cartilage. Optionally, the cartilage is articular cartilage and the regeneration and/or destruction of the cartilage is associated with an injury or a cartilaginous disorder. For example, biological activity may be quantified by the inhibition of proteoglycan (PG) release from articular cartilage, the increase in PG synthesis in articular cartilage, the inhibition of the production of NO, etc.

A "small molecule" is defined herein to have a molecular weight below about 600 daltons, and is generally an organic compound.

The term "isolated" when it refers to the various polypeptides of the invention means a polypeptide which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the polypeptide of the invention will be purified (1) to greater than 95% by weight of the compound as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated compound, e.g. antibody or polypeptide, includes the compound in situ within recombinant cells since at least one component of the compound's natural environment will not be present. Ordinarily, however, isolated compound will be prepared by at least one purification step.

The word "label" when used herein refers to a detectable compound or composition which is conjugated directly or indirectly to the compound, e.g. antibody or polypeptide, so as to generate a "labelled" compound. The label may be detectable by itself (e.g. radioisotope labels or fluorescent labels) or, in the case of an enzymatic label, may catalyze chemical alteration of a substrate compound or composition which is detectable. The word "instruction" by contrast, as used herein refers to language affixed to the packaging of containers indicating a use in conformity with the claimed methods.

By "solid phase" is meant a non-aqueous matrix to which the compound of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the insulin and insulin variants disclosed herein) to a mammal. The components of the liposome are commonly arranged in a bilayer formation, similar to the lipid arrangement of biological membranes.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The term "extended-release" or "sustained-release" formulations in the broadest possible sense means a formulation of active insulin or insulin variant polypeptide resulting in the release or activation of the active polypeptide for a sustained or extended period of time—or at least for a period of time which is longer than if the polypeptide was made available in vivo in the native or unformulated state. Optionally, the extended-release formulation occurs at a constant rate and/or results in sustained and/or continuous concentration of the active polypeptide. Suitable extended release formulations may comprise microencapsulation, semi-permeable matrices of solid hydrophobic polymers, biodegradable polymers, biodegradable hydrogels, suspensions or emulsions (e.g., oil-in-water or water-in-oil). Optionally, the extended-release formulation comprises poly-lactic-co-glycolic acid (PLGA) and can be prepared as described in Lewis, "Controlled Release of Bioactive Agents form Lactide/Glycolide polymer," in Biodegradable Polymers as Drug Delivery Systems, M. Chasin & R. Langeer, Ed. (Marcel Dekker, New York), pp. 1-41. Optionally, the extended-release formulation is stable and the activity of the insulin or insulin variant does not appreciably diminish with storage over time. More specifically, such stability can be enhanced through the presence of a stabilizing agent such as a water-soluble polyvalent metal salt.

Table 1 below provides the complete source code for the ALIGN-2 sequence comparison computer program. This source code may be routinely compiled for use on a UNIX operating system to provide the ALIGN-2 sequence comparison computer program.

Tables 2-5 below shows hypothetical exemplifications for using the below described method to determine % amino acid sequence identity (Tables 2-3) and % nucleic acid sequence identity (Tables 4-5) using the ALIGN-2 sequence comparison computer program, wherein "PRO" represents the amino acid sequence of a hypothetical polypeptide of the invention of interest, "Comparison Protein" represents the amino acid sequence of a polypeptide against which the "PRO" polypeptide of interest is being compared, "PRO-DNA" represents a hypothetical "PRO"-encoding nucleic acid sequence of interest, "Comparison DNA" represents the nucleotide sequence of a nucleic acid molecule against which the "PRO-DNA" nucleic acid molecule of interest is being compared, "X," "Y" and "Z" each represent different hypothetical amino acid residues and "N", "L" and "V" each represent different hypothetical nucleotides.

TABLE 2

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| | | |
|---|---|---|
| PRO | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| | | |
|---|---|---|
| PRO-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| | | |
|---|---|---|
| PRO-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Modes for Carrying Out the Invention

A. Articular Cartilage Explant Assay

In this assay, the synthetic and prophylactic potential of the test compound on intact cartilage is described. To this end, proteoglycan (PG) synthesis and breakdown, and nitric oxide release are measured in treated articular cartilage explants. Proteoglycans are the second largest component of the organic material in articular cartilage (Kuettner, K. E. et al., *Articular Cartilage Biochemistry*, Raven Press, New York, USA (1986), p. 456; Muir, H., *Biochem. Soc. Tran.* 11: 613-622 (1983); Hardingham, T. E., *Biochem. Soc. Trans.* 9: 489-497 (1981). Since proteoglycans help determine the physical and chemical properties of cartilage, the decrease in cartilage PGs which occurs during joint degeneration leads to loss of compressive stiffness and elasticity, an increase in hydraulic permeability, increased water content (swelling), and changes in the organization of other extracellular components such as collagens. Thus, PG loss is an early step in the progression of cartilaginous disorders, one which further perturbs the biomechanical and biochemical stability of the joint. PGs in articular cartilage have been extensively studied because of their likely role in skeletal growth and disease. Mow, V. C., & Ratcliffe, A. *Biomaterials* 13: 67-97 (1992). Proteoglycan breakdown, which is increased in diseased joints, is measured in the assays described herein by quantitating PGs released into the media by articular cartilage explants using the colorimetric DMMB assay. Farndale and Buttle, *Biochem. Biophys. Acta* 883: 173-177 (1985). Incorporation of $^{35}S$-sulfate into proteoglycans is used to measure proteoglycan synthesis.

The evidence linking interleukin-1α, IL-1α, and degenerative cartilaginous disorders is substantial. For example, high levels of IL-1α (Pelletier J P et al., "Cytokines and inflammation in cartilage degradation" in *Osteoarthritic Edition of Rheumatic Disease Clinics of North America*, Eds. R W Moskowitz, Philadelphia, W.D. Saunders Company, 1993, p. 545-568) and IL-1 receptors (Martel-Pelletier et al., *Arthritis Rheum.* 35: 530-540 (1992) have been found in diseased joints, and IL-1α induces cartilage matrix breakdown and inhibits synthesis of new matrix molecules. Baragi et al., *J. Clin. Invest.* 96: 2454-60 (1995); Baragi et al., *Osteoarthritis Cartilage* 5: 275-82 (1997); Evans et al., *J. Leukoc. Biol.* 64: 55-61 (1998); Evans et al., *J. Rheumatol.* 24: 2061-63 (1997); Kang et al., *Biochem. Soc. Trans.* 25: 533-37 (1997); Kang et al., *Osteoarthritis Cartilage* 5: 139-43 (1997). Because of the association of IL-1α with disease, the test compound is also assayed in the presence of IL-1α. The ability of the test compound to not only have positive effects on cartilage, but also to counteract the catabolic effects of IL-1α is strong evidence of the protective effect exhibited by the test compound. In addition, such and activity suggests that the test compound could inhibit the degradation which occurs in arthritic conditions, since catabolic events initiated by IL-1α are also induced by many other cytokines and since antagonism of IL-1α activity has been shown to reduce the progression of osteoarthritis. Arend, W. P. et al., *Ann. Rev. Immunol.* 16: 27-55 (1998).

The production of nitric oxide (NO) can be induced in cartilage by catabolic cytokines such as IL-1. Palmer, R M J et al., *Biochem. Biophys. Res. Commun.* 193: 398-405 (1993). NO has also been implicated in the joint destruction which occurs in arthritic conditions. Ashok et al., *Curr. Opin. Rheum.* 10: 263-268 (1998). Unlike normal (undiseased or uninjured) cartilage, osteoarthritic cartilage produced significant amounts of nitric oxide ex vivo, even in the absence of added stimuli such as interleukin-1 or lipopolysaccharide (LPS). In vivo animal models suggest that inhibition of nitric oxide production reduces progression of arthritis. Pelletier, J P et al., *Arthritis Rheum.* 7: 1275-86 (1998); van de Loo et al., *Arthritis Rheum.* 41: 634-46 (1998); Stichtenoth, D. O. and Frolich J. C., *Br. J. Rheumatol.* 37: 246-57 (1998). In vitro, nitric oxide exerts detrimental effects on chondrocyte function, including inhibition of collagen and proteoglycan synthesis, inhibition of adhesion to the extracellular matrix, and enhancement of cell death (apoptosis). Higher concentrations of nitrite are found in synovial fluid from osteoarthritic patients than in fluid from rheumatoid arthritic patients. Renoux et al., *Osteoarthritis Cartilage* 4: 175-179 (1996). Furthermore, animal models suggest that inhibition of nitric oxide production reduces progression of arthritis. Pelletier, J. P. et al., *Arthritis Rheum.* 7: 1275-86 (1998); van de Loo et al., *Arthritis Rheum.* 41: 634-46 (1998); Stichtenoth, D. O. & Frolich, J. C., *Br. J. Rheumatol.* 37: 246-57 (1998). Since NO also has effects on other cells, the presence of NO within the articular joint could increase vasodilation and permeability, potentiate cytokine release by leukocytes, and stimulate angiogenic activity. Since NO likely play a role in both the erosive and the inflammatory components of joint diseases, a factor which decreases nitric oxide production would likely be beneficial for the treatment of cartilaginous disorders.

The assay to measure nitric oxide production described herein is based on the principle that 2,3-diaminonapthalene (DAN) reacts with nitrite under acidic conditions to form 1-(H)-naphthotriazole, a fluorescent product. As NO is quickly metabolized into nitrite ($NO_2^{-1}$) and nitrate ($NO_3^{-1}$), detection of nitrite is one means of detecting (albeit undercounting) the actual NO produced by cartilage.

The procedures employed are described in greater detail in the examples.

B. Maintenance of Chondrocytes in Serum-free Culture

In this procedure, the ability of the test compound to enhance, promote or maintain the viability of chondrocytes in cultures in the absence of serum or other growth factors is examined. Articular chondrocytes are first prepared by removal of the extracellular matrix and cultured in a monolayer, which is believed to approximate the latter stages of cartilage disorders when the matrix has been depleted.

The assay is a colorimetric assay that measures the metabolic activity of the cultured cells based on the ability of viable cells to cleave the yellow tetrazolium salt MTT to form purple formazan crystals. This cellular reduction reaction involves the pyridine nucleotide cofactors NADH and NADPH. Berridge, M. V. & Tan, A. S., *Arch. Biochem. Biophys.* 303: 474 (1993). The solubilized product is spectrophotometrically quantitated on an ELISA reader. The procedure is described in greater detail in the examples.

C. Mouse Patellae Assay

The experiment examines the effects of the test compounds on proteoglycan synthesis in patellae (kneecaps) of mice. This assay uses intact cartilage (including the underlying bone) and thus tests factors under conditions which approximate the in vivo environment of cartilage. Compounds are either added to patellae in vitro, or are injected into knee joints in vivo prior to analysis of proteoglycan synthesis in patellae ex vivo. As has been shown previously, in vivo treated patellae show distinct changes in PG synthesis ex vivo (Van den Berg et al., *Rheum. Int.* 1: 165-9 (1982); Vershure, P. J. et al., *Ann. Rheum. Dis.* 53: 455-460 (1994); and Van de Loo et al., *Arthrit. Rheum.* 38: 164-172 (1995). In this model, the contralateral joint of each animal can be used as a control. The procedure is better described in the examples.

D. Guinea Pig Model

Figure 8:
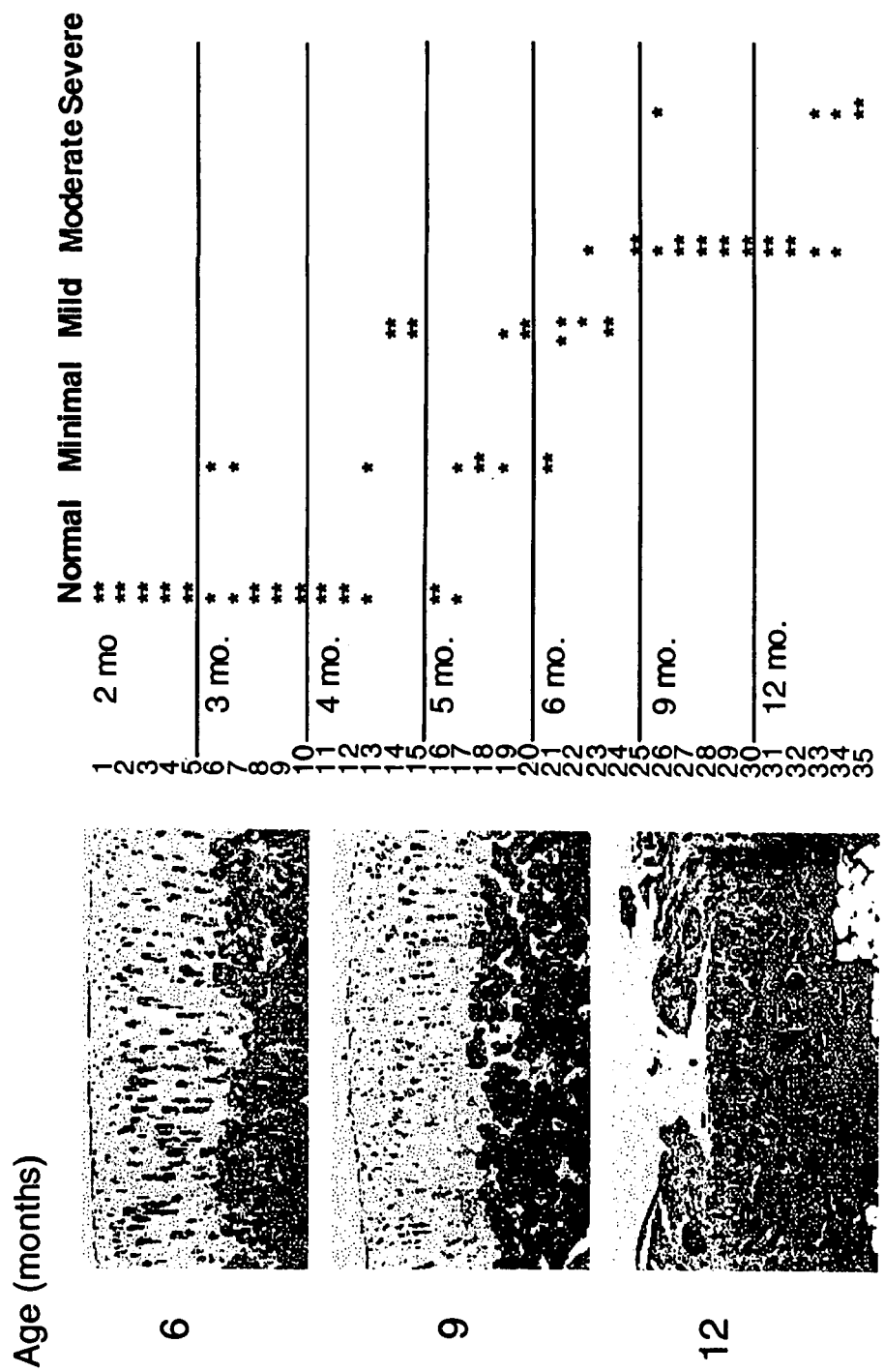
FIG. 8 shows the spontaneous joint degeneration which occurs in Hartley guinea pigs as they age. The degeneration in the femorotibial joint of male Hartley guinea pigs occurs in an age-dependent manner, as shown by histological analysis of articular cartilage at various ages (6, 9 and 12 months, left side FIG. 8A). The histopathologic changes were graded as minimal, moderate or severe (right side, FIG. 8B). Minimal changes include focal chondrocyte degradation, disruption of the superficial layer of cartilage, and decreased toluidine blue matrix staining. Mild lesions were similar, but covered up to one-third of the surface and often affected part of the middle layer. Moderate changes covered most of the surface and included most of the middle layer. Severe changes had extensive deep layer degeneration, osteophytes, chondrocyte cloning, subchondral bone thickening, synovial hyperplasia and fibrosis. Each asterisk (*) represents one knee joint. (Data adapted from Wei, L. et al., *Arthrits Rheum.* 40: 2075-2083 (1997) and Bendele, A., *Lab. Anim. Sci.* 39: 115-121 (1989).

These experiments measure the effects of the test compound on both the stimulation of PG synthesis and inhibition of PG release in articular cartilage explants from a strain of guinea pigs, Dunkin Hartley (DH), which spontaneously develops knee osteoarthritis (OA). Most other animal models which cause rapidly progressing joint breakdown resemble secondary OA more than the slowly evolving human primary OA. In contrast, DH guinea pigs have naturally occurring slowly progressive, non-inflammatory OA-like changes. Because the highly reproducible pattern of cartilage breakdown in these guinea pigs is similar to that seen in the human disorder, the DH guinea pig is a well-accepted animal model for osteoarthritis. Young et al., "Osteoarthrits", Spontaneous animal models of human disease vol. 2, pp. 257-261, Acad. Press, New York. (1979); Bendele et al., *Arthritis Rheum.* 34: 1180-1184; Bendele et al., *Arthritis Rheum.* 31: 561-565 (1988); Jimenez et al., *Laboratory Animal Sciences* 47 (6): 598-601 (1997); Wei et al., *Acta Orthop Scand* 69: 351-357 (1998)). Initially, these animals develop a mild OA that is detectable by the presence of minimal histologic changes. However, the disease progresses, and by 16-18 months of age, moderate to severe cartilage degeneration within the joints is observed (FIG. 8).

As a result, the effect of the test compound on the cartilage matrix of the DH guinea pigs over the progression of the disease would be indicative of the therapeutic effect of the compound in the treatment of OA at different stages of joint destruction.

The procedure is described in better detail in the examples.

E. Diabetic Mouse Model

The metabolic changes associated with diabetes mellitus (diabetes) affect many other organ and musculo-skeletal systems of the afflicted organism. For example, in humans, the incidence of musculoskeletal injuries and disorders is increased with the onset of diabetes, and diabetes is considered a risk factor for the development of arthritis.

A syndrome similar to diabetes can be induced in animals by administration of streptozotocin (STZ). Portha B. et al., *Diabete Metab.* 15: 61-75 (1989). By killing pancreatic cells which produce insulin, STZ decreases the amount of serum insulin in treated animals. STZ-induced diabetes is associated with atrophy and depressed collagen content of connective tissues including skin, bone and cartilage. Craig, R. G. et al., *Biochim. Biophys. Acta* 1402: 250-260 (1998).

In this procedure, the patellae of treated STZ-treated mice are incubated in the presence of the test compound and the resulting matrix synthesis is analyzed. The ability of the test compound to increase or restore the level of PG synthesis to that of untreated controls is indicative of the therapeutic potential. The procedure is better described in the examples.

F. Extended Release Formulation as Polymeric Microspheres

While intermittent injections are generally well-tolerated by patients and once/week injections of therapeutics are currently being tested clinically, an ideal drug would be one in which a limited number of doses was required. However, when the active compound is unstable or is quickly degraded at physiological conditions, a stabilized, slow-release formulation is highly desirable.

These experiments, described in greater detail as Examples 6-8 examine the effectiveness of a slow-release formulation of the tested compound as indicated by (1) the size, protein load and physical integrity; (2) the release profile of the test compound from the slow-release matrix; and (3) the biological activity of the test compound after release from the slow-release matrix.

These procedures are better described in the examples below.

1. Physical Characteristics

Under some circumstances, it may be first necessary or desirable to stabilize the test compound with other complexing or stabilizing agents prior to incorporation into the slow-release form. For example, while the particular compound of the invention human insulin (HI) would appear to be very effective in treating cartilaginous disorders, it is unstable when stored in neutral conditions at low concentrations for extended periods of time. J. Brenge and L. Langkjoer, *Insulin Formulation* and *Delivery in Protein Delivery*, Eds, L M. Sanders and W. Hendren, Plenum Press, 1997. Moreover, HI is quickly degraded in the body, having a half-life of only 5 minutes in the human body. Hadley, ME, *Endocrinology*, Prentice-Hall, Inc. 1988.

One potential solution to the problem of a short life and instability that has been attempted with HI is formulation with zinc. A sparingly soluble zinc acetate:HI formulation has been attempted elsewhere, based on histochemical evidence suggesting that insulin is stored in the pancreas in a complex with zinc. Eli Lilly, Indianapolis, Ind.; J. Brenge and L. Langkjoer, supra.; Hadley, supra. Other evidence indicates that HI complexed with zinc is more resistant to aggregation and has a slower onset and longer duration of activity relative to uncomplexed material. J. Brenge & L. Langkjoer, supra.

The slow-release formulation described in this procedure comprises microencapsulation of a spray-freeze dried compound into a poly lactic-coglycolic acid (PLGA) matrix using the procedure as described by Gombotz et al., U.S. Pat. No. 5,019,400 and Johnson et al., *Nature Med.* 2(7): 795-799 (1996).

In this procedure, the amount of test compound in the slow-release composition was determined by chemical analysis, while the physical and biological integrity of the test material recoverable from the compositions were determined by size-exclusion (SEC) and reverse phase chromatography (RPC).

2. Release Profiles

In this procedure, the insulin-loaded PLGA microspheres were incubated in 3 different conditions and the recovered protein was analyzed for activity at several timepoints. In this slow-release system, test compound is released from the microsphere by treatment with sodium hydroxide and/or histidine buffer. In order to better approximate physiological conditions, the microspheres are also incubated in either synovial fluid or with articular cartilage explants.

The release of the test compound from the microsphere is determinable by any method which is typically used for assaying for the presence and/or activity of the test compound. For example, with HI, a suitable technique is the use of an insulin receptor kinase assay (KIRA) in cells expressing the insulin receptor (e.g., CHO cells).

3. Biological Activity

In this procedure the biological activity of the test compound released from microencapsulation is determined.

Even though the procedure of the last section was a measure of biological activity of the test compound in the generic sense, it is important to confirm that the released test compound still retains a particular desired biological activity on articular cartilage (e.g., stimulation of matrix synthesis and inhibition of matrix breakdown).

G. Human Articular Cartilage Explant Assay

In a manner similar to that described above under articular cartilage explant assay, this procedure measures the anabolic effects of the test molecule, except that the tissue source is human. The procedure is described in greater detail in Example 9.

III. Compositions and Methods of the Invention

A. Full-Length Insulin and/or Variants Thereof

The present invention provides in part a novel method for using insulin and insulin variant polypeptides to treat cartilaginous disorders, including regenerating and/or preventing the degradation of cartilage. In particular, cDNAs encoding insulin and insulin variant polypeptides have been identified, isolated and their use in the treatment of cartilaginous disorders is disclosed herein. Insulin is a well-known molecule and recombinant human insulin is readily available from numerous commercial suppliers including Lilly, Novo-Nordisk, and Sigma. Alternatively the insulin and insulin variant molecules for use with the present invention may be obtained by any known technique from the polypeptide sequence identified as SEQ ID NO:1 & 2 (FIGS. 18A & 18B).

Figure 17A:
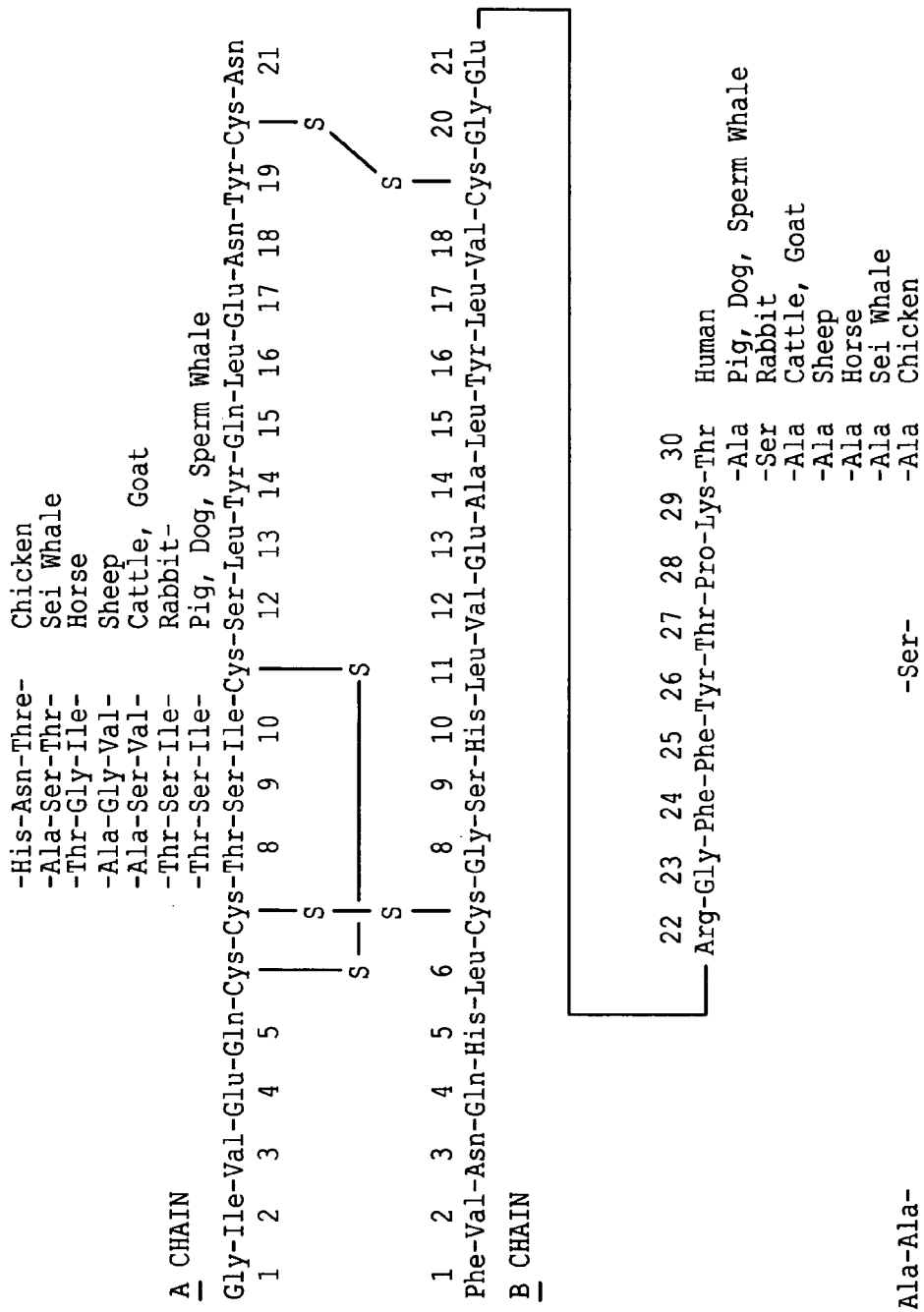
FIGS. 17A and 17B are diagrams representing the primary structure of insulin. Shown are a comparative diagram of the primary structure of selected vertebrate insulin (FIG. 17A), and the primary structure of porcine pro-insulin (FIG. 17B). The data was adapted from Hadley, M. E., *Endrocrinology*, Prentice Hall Inc., 1988.
Figure 17B:
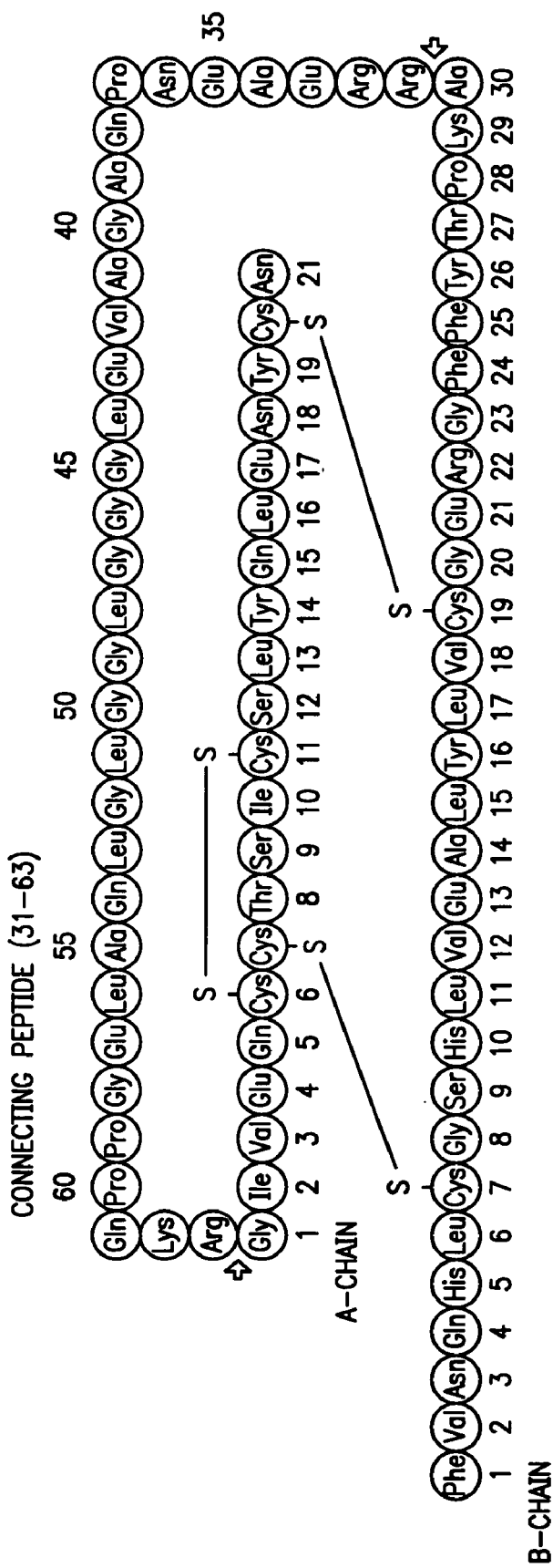

Native human insulin has two peptide chains, an A chain containing 21 amino acids (SEQ ID NO:1) and a B chain containing 30 amino acid residues (SEQ ID NO:2). The two chains contain 3 disulfide bridges, each formed of two cysteinyl residues. Two of the bridges are interchain bridges, between residues A7-B7 and A-20-B-19, and the other is an intrachain bridge between residues A-6-A-11 (FIGS. 17A-B).

Insulin may be produced be the separate expression of the A and B chains, followed by a refolding reaction to form the disulfide bonds. Chance et al., *Diabetes Care* 4: 147-154 (1982). These chains may be expressed in *E. coli* as β-galactosidase fusion proteins. Williams et al., *Science* 215(5): 687-689 (1982). The separate chains (S-sulfonated forms) can be combined to in the presence of mercaptan to obtain the active molecule. Goeddel et al., *Proc. Natl. Acad. Sci. U.S.A.* 76(1): 106-110 (1979). Because of the large size of the β-gal fusion protein (i.e. over 1000 amino acids), premature detachment from the ribosome often occurs, resulting in incomplete insulin translations. Burnett, *Experimental Manipulation of Gene Expression*, Inouye, Ed. Academic Press, New York, pp 259-277 (1983). An improvement in this procedure is the use of the tryptophan (Trp) operon in place of the lac operon in the β-gal expression system. Hall, *Invisible Frontiers—The Race to Synthesize a Human Gene*, Atlantic Monthly Press, New York, 1987). The Trp operon is a series of five bacterial genes which sequentially synthesize the enzymes responsible for the anabolism of tryptophan. The Trp operon offers several advantages: (1) the Trp E only has about 190 amino acid residues as compared to the β-gal enzyme (1000), thus greatly reducing the probability of premature chain termination; (2) the Trp E gene increases expression of the fusion protein, resulting in 10-fold greater expression compared to the lac (i.e., β-gal) system; (3) the Trp operon is activated when the fermentation media is deficient in tryptophan, thus, expression can be turned on when host cell mass is at a maximum by allowing the fermentation media to become depleted in tryptophan.

When the fermentation is complete, the protein is recovered by disruption of the cell walls and recovery of the inclusion bodies, followed by CNBr cleavage to release to A or B chains and purified by ion exchange, size exclusion and reversed-phase high-performance liquid chromatography to obtain the purified recombinant product. Frank and Chase, *Munch Med. Wschr.* 125 (Suppl. 1); 514-520(1983).

Another common method of producing insulin involves the production of proinsulin. Native sequence proinsulin (SEQ ID NO:3)(FIG. 18C) is a single chain polypeptide in which the N-terminus of the insulin A-chain is linked through a connecting peptide with the C-terminus of the insulin B-chain, and the appropriate cysteinyl residues are joined by disulfide bonds. Human native sequence proinsulin has 86 amino acid residues, 35 of which make up the connecting peptide, sometimes known as the C-peptide (SEQ ID NO:4)(FIG. 18D). Yanaihara et al., *Diabetes* 27 (Suppl. 1): 149-160 (1978). The principal importance of the C-peptide is to facilitate the formation of the proper disulfide bridging and/or the trypsin-like processing at the site of two adjacent basic amino acids. Bell et al., *Nature* 284: 26-32 (1980); Thim et al., *PNAS* 83: 6766-6770 (1986). This connecting peptide is removeable through enzymatic digestion. W. Kemmler et al., *J. Biol. Chem.* 246: 6786 (1971).

Production of proinsulin is described in Kroeff et al., *J. Chromatogr.* 481: 45-61 (1989). Expression may be carried in *E. coli* by linking a methionine gene and the proinsulin gene into a bacterial gene in a plasmid vector that is introduced. Proinsulin is then released from the bacterial protein by destruction of the methionine linker, refolded and the C-peptide removed to yield active insulin.

Many proinsulin variants with modifications to the C-peptide have been attempted. For example, EP 704,527 discloses the use of any peptide which contains at least one N-glycosylation site, preferably -Asn-X-Ser-. Additional C-peptide variants contain from 2 to 35 amino acids (DK-A-5284/87), or simply a dipeptide of -Lys-Arg- (EP-A-195-691). Other C-peptide variants Other C-peptides variants have been described as only containing at least one proteolytic cleavage site, preferably -KR-X-KR- (SEQ ID NO:5), -KR-X-M-(SEQ ID NO:6) or -N-X-KR- (SEQ ID NO:7), wherein X is any chain of residues to facilitate cleavage and processing by host yeast cells. The advantage of host processing is that it eliminates or reduces the need for processing the proinsulin through digestion and purification steps in order to arrive at the mature form. Other C-peptide modifications include the deletion of residues Arg32 to Glu35, Arg32 to Asp36, Arg32 to Glu35 or Arg32 to Gly60 to render the precursor susceptible to a site specific protease generated from a mutant *Pseudomonasfragi* (WO 86/01540). Another strategy includes the connecting molecule -X-Y-, wherein X is a moiety joining the α-amino group of A1 and to either the ε-amino group of B-29 or the carboxyl group of B-30, which is enzymatically or chemically cleavable without disruption to either the A or B insulin chains; and Y is Lys-B30, wherein B30 is Ala, Thr or Ser. (U.S. Pat. No. 4,430,266).

Other expression strategies have deleted the C-peptide entirely, and have expressed a variant "proinsulin" as a peptide containing a shortened B-chain (B1-29-carboxyl Ala residue deleted) connected via the C-terminal with the N-terminal end of the complete A chain (A1-21). Alternatively, the C-peptide may be from 1-33 residues so long as there are not two adjacent basic amino acids, for example, -Ser-Lys- or -Ala-Ala-Lys (EP-A-427-296), alternatively -Arg-Arg-Gly-Ser-Lys-Arg- (SEQ ID NO:8) or -Arg-Arg- (EP 055,945), alternatively -Arg- or Lys-Arg- (WO 96/20724).

Various other strategies have been employed to increase the expression levels in prokaryotic hosts, including the insertion of amino acid residues (e.g., Ala, Arg, Gln, Gly, Ile, Leu, Lys, Met, Phe, Ser, Thr, Try or Val) between the methionine and the coding sequence (EP 0 534 705). An alternative production scheme involving the production of GPI-fusion proteins commensurate with deactivation of gas-1 in yeast is described in WO 95/22614, EP 324,274, EP 557,976.

Finally, the art is replete with many mature insulin variants having antidiabetic activity. For example, E.P. 0 544 466 describes variants having residue B3 and A21 independently selected from Ala, Arg, Asn, Cys, Gly, Gln, Glu, His, Ile, Leu, Lys, Met, Phe, Pro, Ser, Thr, Trp, Tyr and Val in combination with B10 being His, Asp or Glu. U.S. Pat. No. 5,514,646 discloses variants which dimerize less readily and are therefore more rapidly active than the unaltered mature molecule. For example, A21 is selected from Ala, Asn, Asp, Gln, Glu, Gly, Thr or Ser; B1 is Phe, Asp or absent; B2 is Val, or absent when B1 is absent; B3 is Asn or Asp; B9 is Ser or Asp; B10 is His or Asn; B28 is any naturally occurring amino acid; B29 is Pro, hydroxypro; B30 is Ala, Thr or absent; and X-Y-Z are C-terminal additions to residue B30 wherein Z is —OH, methoxy or ethoxy, X is Arg, Arg-Arg, Lys, Lys-Lys, Arg-Lys, Lys-Arg or absent and Y is present only when X is present and is Glu or any fragment of the sequence -Glu-Ala-Glu-Asp-Leu-Gln-Val-Gly-Gln-Val- Glu-Leu-Gly-Gly-Gly-Pro-Gly-Ala-Gly-Ser-Leu-Gln-Pro- Leu-Ala-Leu-Gly-Gly-Ser-Leu-Gln-Lys-Arg (SEQ ID NO:9). WO 95/07931 discloses variants in which residues A21 and B3 are independently any natural amino acid other than Lys, Arg and Cys, B1 is Phe or deleted, B30 is deleted or any natural amino acid other than Lys, Arg or Cys having a lipophilic substituent on the α-amino group of B29. B30 may also be replaced by a non-codable lipophilic amino acid having from 10 to 24 carbon atoms having an acyl group with up to 5 carbon atoms bound to the α-amino group of B29. EP 0 214 826 describes insulin variants in which from 1-7 of the following are substituted with the same or different residues so as to give the mature molecule the same charge or a greater negative charge at neutral pH than that of human insulin: A9-10, A13, A21, B1-2, B5, B9-10, B12, B14, B16-18, B20, B26-28. RD 365030 (Research Disclosure, September 1994) discloses the substitution of Asp for Pro at residue 28 and the deletion of B30 in order to permit the conversion of proinsulin into the active form by a lysyl specific endopeptidase from *Achromobacter lyticus* instead of trypsin-activated cleavage. WO 89/10937 discloses insulin variants in which one or more Asp or Gln residues (e.g., A5, A15, B4) have been replaced by another naturally occurring amino acid. EP 0 375 437 discloses insulin variants in which a positively charged amino acid (i.e., Lys or Arg) is substituted at position B28 or alternatively the deletion of one of residues B24, B25, B26, B27 or B28 resulting in a positive charge at the new B28 residue. U.S. Pat. No. 5,656,722 discloses long acting insulin variants in which residue A21 is Gly, Ala, Ser, Thr, Val, Leu, Ile, Asp, Glu, Cys, Met, Arg, Lys, His, Tyr, Phe, Trp, Pro; B1 is absent or is Phe, B10 is any naturally occurring amino acid (preferably Asn or Gln); B30 is a neutral amino acid (e.g., Ala, Ser, Thr); B31 is a basic organic group having up to 50 carbon atoms comprising from 1-3 basic α-amino acids (e.g., Arg, Lys, Hyl, Orn, Cit, His). The delayed onset is believed to be due to the sparing solubility at the isoelectric point caused by the basic groups. These molecule become active upon enzymatic cleavage of the basic groups (e.g., trypsin, carboxypeptidase B, esterase). A further variation of these molecules is described in U.S. Pat. No. 5,506,302 wherein the basic residue arginine is positioned at the N-terminal of the A1 glycine residue. E.P. 0 519 750 discloses insulin variants with Asp substitutions at residue B10 in combination with the deletion of B27-30 or B28-30, optionally including substitution of residue A21 with Asn, Asp, Glu, Gln, Ala, Gly or Ser, residue B1 with Phe or Asp or residue B3 with Asn or Asp.

Finally, the following molecules have been described as having anti-diabetic activity:

(1) GIVEQ(C)$_1$(C)$_2$TSI(C)$_1$SLYQLENY(C)$_3$N (SEQ ID NO:10) FVNQHL(C)$_2$GSHLVEALYLV(C)$_3$GERGFFYTP- KTRREAEDLQVGQVELGGGPGAGSLQPLX (SEQ ID NO:11), wherein the subscripts represent the location of disulfide bonds and X is present or absent, and if present is ALEGSLQ (SEQ ID NO:12) or ALEGSLQKR (SEQ ID NO:13)(EP 0 171,886);

(2) EAEDLQVGQVELGGGGAGSLQPLA- LEGSLQKR-GIVEQ(C)$_1$(C)$_2$TSICSLYQLENY(C)$_3$N (SEQ ID NO:14) FVNQHL(C)$_2$GSHLVEALYLV(C)$_3$GE-RGFFYTPKT- (RR)$_n$, wherein n is 1 (SEQ ID NO:15) or 0 (SEQ ID NO:16)(E.P 171,147), wherein the subscripts represent the location of disulfide bonds; or (3) ALEGSLQKRGIVEQ(C)$_1$(C)$_2$TSI(C)$_1$SLYQLENY (C)$_3$N (SEQ ID NO:17) FVNQHL(C)$_2$GSHLVEALYLV (C)$_3$GERGFFYTPKTX, wherein the subscripts represent the location of disulfide bonds (EP 171,887), and X is present or absent (SEQ ID NO:18), and if present is -R-R or -RREAEDLQVGQVELGGGPGAGSLQPL (SEQ ID NO:19).

In the presence of ionic zinc ($Zn^{2+}$), natural human insulin associates to a hexamer with 2 Zn atoms coordinated octahedrally to HB10 of each monomer and 3 water molecules. Blundell et al., *Adv. Protein Chem.* 26: 279-402 (1972), Baker et al., *Philos. Trans. R. Soc. London B* 319, 369-456 (1988). The $Zn^{2+}$ binding thereby causes allosteric conformational changes.

Phenolic ligands or certain salts are capable of inducing a conformational transition, resulting in the N-terminal 8 amino acids of the B-chain converting from and extended conformation to an α-helix. This conformational change allows two Zn atoms to become tetrahedrally coordinated to HB10 of each monomer and a fourth solvent-accessible site to be occupied by small anionic ligands, i.e., $Cl^{1-}$ ion, Brader & Dunn, TIBS 16: 341-345 (1991). The conformational state induced by phenolic ligands is referred to as the R state while the pre-conformational form as the T state. Monod et al., *J. Mol. Biol.* 12: 88-118 (1965). The R state is more compact, less flexible, and the Zn is more tightly bound compared to the T state. Derewenda et al., *Nature* 338: 594-596 (1989). The conversion of insulin between the T and R allosteric conformations involves the movement of the B(1) alpha carbon a distance greater than 30 Å, a very sizeable distance for an allosteric transformation.

The conformational change instigated by the presence of phenolic ligands has the effect of increasing shelf-life stability. Brange et al., *Pharm. Res.* 9: 715-726 (1992); Brange et al., *Pharm. Res.* 9: 727-734 (1992); Brange & Langkjaer, *Acta Pharm. Nord.* 4: 149-158 (1992). One theory explaining why shelf life is increased is through a thermodynamic model describing the degradation of insulin by the equilibrium constant of unfolding, $K_{eq}$. Brems et al., *Protein Engineering* 5: 519-525 (1992). This equilibrium constant of

[U]/[N] is determined from the reaction N←→U, wherein N is native and U is insulin in unfolded conformation. Since the R state is the conformation more compacted and less flexible, and Zn is more tightly bonded, the R state is also expected to provide the greatest protection from degradation.

The rate of absorption of insulin is directly related to the dissociation constant for self-association. Brange et al., *Diabetes Care* 13: 923-954 (1990). The form of insulin which is actually absorbed is believed to be a monomer and the rate of dissociation is the rate-limiting step. Binder, C., *Artificial Systems for Insulin Delivery*, Brunetti et al., Eds, Raven Press, N.Y., 53-57 (1983). Moreover, monomeric insulin analogs are rapidly absorbed and result in a rapid time action profile. Brange et al., *Curr. Opin. Struct. Biol.* 1: 934-940 (1991); DiMarchi et al., *Peptides: Chemistry and Biology*, Proceedings of the Twelfth American Peptide Symposium, ESCOM, Leiden, pp. 26-28 (1992). Thus the presence of Zn and/or other phenolics has been attempted to postpone the dissociation of the Zn-insulin hexamers and increase shelf life. However, insulin can be induced into a hexamer in the absence of zinc by substituting GluB13 for GlnB13. Gentley, et al., *J. Mol. Biol.* 228: 1163-1176. Moreover, the hexamer may also be induced in the absence of insulin by the substitution of an aspartic acid at position 1 of the B chain and optionally glutamine at position B13 (WO 96/04307).

B. Insulin Variants

In addition to the full-length native sequence insulin polypeptides described herein, it is possible to create insulin variants. Whereas changes in the formulation may be done to effect the desired changes in activity, the term "insulin variants" is explicity intended to cover changes and/or modifications to the polypeptide sequence. Discussion of modifications in the formulation appears under section "E. Pharmaceutical compositions and dosages." Other formulation or sequence changes in insulin could, in theory, alter the processing and/or the intracellular trafficking of an insulin variant, improve binding to the receptor and/or protein stability, etc. Such changes could thus ultimately improve the bioactivity of an insulin variant relative to the native molecule.

Variations in the amino acid sequence of insulin or in various domains of the insulin polypeptide described herein, can be made, for example, using any of the techniques and guidelines for conservative and non-conservative mutations set forth, for instance, in U.S. Pat. No. 5,364,934. Variations may be a substitution, deletion or insertion of one or more nucleotides encoding the insulin polypeptide that results in a change in the amino acid sequence of the polypeptide as compared with the native sequence insulin polypeptide. Optionally the variation results in substitution of at least one amino acid with any other amino acid in one or more of the domains of the insulin polypeptide. Guidance in determining which amino acid residue may be inserted, substituted or deleted without adversely affecting the desired activity may be found by comparing the sequence of the insulin polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Insulin polypeptide fragments of the polypeptides of the invention are also within the scope of the invention. Such fragments may be truncated at the N-terminus or C-terminus, or may lack internal residues, for example, when compared with a full length native protein. Certain fragments lack amino acid residues that are not essential for a desired biological activity of the insulin or insulin variant polypeptide.

Insulin fragments may be prepared by any of a number of conventional techniques. Desired peptide fragments may be chemically synthesized. An alternative approach involves generating insulin fragments by enzymatic digestion, e.g., by treating the protein with an enzyme known to cleave proteins at sites defined by particular amino acid residues, or by digesting the DNA with suitable restriction enzymes and using the desired fragment to generate recombinant protein. Yet another suitable technique involves isolating and amplifying a DNA fragment encoding a desired polypeptide fragment, by polymerase chain reaction (PCR). Oligonucleotides that define the desired termini of the DNA fragment are employed as the 5' and 3' primers in the PCR. Preferably, polypeptide fragments share at least one biological and/or immunological activity with the insulin A-chain and B-chain polypeptide shown in FIGS. 18A & 18B (SEQ ID NO:1-2).

In particular embodiments, conservative substitutions of interest are shown in Table I under the heading of preferred substitutions. If such substitutions result in a change in biological activity, then more substantial changes, called exemplary substitutions in Table 6, or as further described below in reference to amino acid classes, are introduced prior to screening the resultant protein products.

TABLE 6

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the invention polypeptide are accomplished by selecting substitutions that alter the (a) structure of the polypeptide backbone in the area of the substitution, for example, as a sheet or helical conformation, (b) charge or hydrophobicity of the molecule at the target site, or (c) bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis, Carter et al., *Nucl. Acids Res.,* 13:4331 (1986); Zoller et al., *Nucl. Acids Res.,* 10:6487 (1987), cassette mutagenesis, Wells et al., *Gene,* 34:315 (1985), restriction selection mutagenesis, Wells et al., *Philos. Trans. R. Soc. London SerA,* 317:415 (1986) or other known techniques can be performed on the cloned DNA to produce the variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Cunningham and Wells, *Science,* 244: 1081-1085 (1989). Alanine is also typically preferred because it is the most common amino acid. Further, it is frequently found in both buried and exposed positions. Creighton, *The Proteins,* (W.H. Freeman & Co., N.Y.); Chothia, *J. Mol. Biol.,* 150:1 (1976). If alanine substitution does not yield adequate amounts of variant, an isosteric amino acid may be used.

C. Modifications of Insulin and Insulin Variants

Covalent modifications of insulin and/or insulin variants are included within the scope of this invention. One type of covalent modification includes reacting targeted amino acid residues of an insulin or insulin variant polypeptide with an organic derivatizing agent that is capable of reacting with selected side chains or the N- or C-terminal residues of the molecule. Derivatization with bifunctional agents is useful, for instance, for crosslinking the molecule to a water-insoluble support matrix or surface for use in the method for purifying anti-insulin or anti-insulin variant antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains, acetylation of the N-terminal amine, and amidation of any C-terminal carboxyl group. T. E. Creighton, *Proteins: Structure and Molecular Properties,* W.H. Freeman & Co., San Francisco, pp. 79-86 (1983)], Another type of covalent modification of the invention polypeptide included within the scope of this invention comprises altering the native glycosylation pattern of the polypeptide. "Altering the native glycosylation pattern" is intended for purposes herein to mean deleting one or more carbohydrate moieties found in native sequence polypeptide (either by removing the underlying glycosylation site or by deleting the glycosylation by chemical and/or enzymatic means), and/or adding one or more glycosylation sites that are not present in the native sequence. In addition, the phrase includes qualitative changes in the glycosylation of the native proteins, involving a change in the nature and proportions of the various carbohydrate moieties present.

Addition of glycosylation sites to the polypeptide may be accomplished by altering the amino acid sequence. The alteration may be made, for example, by the addition of, or substitution by, one or more serine or threonine residues to the native sequence polypeptide (for O-linked glycosylation sites). The amino acid sequence may optionally be altered through changes at the DNA level, particularly by mutating the DNA encoding the polypeptide at preselected bases such that codons are generated that will translate into the desired amino acids.

Another means of increasing the number of carbohydrate moieties on the polypeptide of the invention is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.,* pp. 259-306 (1981).

Removal of carbohydrate moieties present on the polypeptide of the invention may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification comprises linking the invention polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670, 417; 4,791,192 or 4,179,337.

The insulin and/or insulin variant polypeptides employable with the present invention may also be modified in a way to form a chimeric molecule comprising the invention polypeptide fused to another, heterologous polypeptide or amino acid sequence.

In one embodiment, such a chimeric molecule comprises a fusion of the invention polypeptide with a tag polypeptide which provides an epitope to which an anti-tag antibody can selectively bind. The epitope tag is generally placed at the amino- or carboxyl-terminus of the polypeptide of the invention. The presence of such epitope-tagged forms of the polypeptide of the invention can be detected using an antibody against the tag polypeptide. Also, provision of the epitope tag enables the polypeptide of the invention to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5, Field et al., *Mol. Cell. Biol.,* 8:2159-2165 (1988); the c-myc tag and the 8F9, 3C7, 6E10, G4, B7 and 9E10 antibodies thereto, Evan et al., *Molecular and Cellular Biology*, 5:3610-3616 (1985); and the Herpes Simplex virus glycoprotein D (gD) tag and its antibody, Paborsky et al., *Protein Engineering*, 3(6):547-553 (1990). Other tag polypeptides include the Flag-peptide, Hopp et al., *BioTechnology*, 6:1204-1210 (1988); the KT3 epitope peptide, Martin et al., *Science*, 255:192-194 (1992); an α-tubulin epitope peptide, Skinner et al., *J. Biol. Chem.*, 266:15163-15166 (1991); and the T7 gene 10 protein peptide tag, Lutz-Freyermuth et al., *Proc. Natl. Acad. Sci. USA*, 87:6393-6397 (1990).

In an alternative embodiment, the chimeric molecule may comprise a fusion of the polypeptide of the invention with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an invention polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of Insulin or Insulin Variant Polypeptides

The description below relates primarily to production of insulin and insulin variant polypeptide by culturing cells transformed or transfected with a vector containing insulin or insulin variant nucleic acid. Alternative methods, which are well known in the art, could also be employed to prepare such polypeptides. For instance, the sequence, or portions thereof, may be produced by direct peptide synthesis using solid-phase techniques (see, e.g., Stewart et al., Solid-Phase Peptide Synthesis, W.H. Freeman Co., San Francisco, Calif. (1969); Merrifield, *J. Am. Chem. Soc.* 85: 2149-2154 (1963)). In vitro protein synthesis may be performed using manual techniques or by automation. Automated synthesis may be accomplished, for instance, using an Applied Biosystems Peptide Synthesizer (Foster City, Calif.) using the manufacturer's instructions. Automated synthesis may be accomplished, for instance, using an Applied Biosystems Peptide Synthesizer (Foster City, Calif.) using the manufacturer's instructions. Various portions of the polypeptide may be chemically synthesized separately and combined using chemical or enzymatic methods to produce the full-length insulin or insulin variant polypeptides.

1. Isolation of DNA Encoding the Polypeptide of the Invention

DNA encoding insulin or insulin variant may be obtained from a cDNA library prepared from tissue believed to express the insulin or insulin variant mRNA and to express it at a detectable level. Accordingly, human insulin or insulin variant DNA can be conveniently obtained from a cDNA library prepared from human tissue. The insulin or insulin variant-encoding gene may also be obtained from a genomic library or by oligonucleotide synthesis.

Libraries can be screened with probes (such as antibodies to the polypeptide of the invention or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding the insulin and/or insulin variant polypeptides is to use PCR methodology. Sambrook et al., supra; Dieffenbach et al., *PCR Primer: A Laboratory Manual* (Cold Spring Harbor Laboratory Press, 1995).

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for insulin or insulin variant production and cultured in conventional nutrient media modified as appropriate for inducing promoters, selecting transformants, or amplifying the genes encoding the desired sequences. General principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of transfection include $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transformations have been described in U.S. Pat. No. 4,399,216. Transformations into yeast are typically carried out according to the method of Van Solingen et al., *J. Bact.*, 130: 946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, polycations, e.g., polybrene, polyornithine, or use of recombinant viral vectors, may also be used. For various techniques for transforming mammalian cells, see Keown et al., *Methods in Enzymology*, 185: 527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as Escherichia, e.g., *E. coli* K12 strain MM294 (ATCC 31,446); *E. coli* X1776 (ATCC 31,537); *E. coli* strain W3110 (ATCC 27,325) and K5 772 (ATCC 53,635), *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may readily modified to turn of its endogenous genes in favor of expression of the heterologous sequence. For example, *E. coli* W3110 strain 1A2, which has the complete genotype tonA; *E. coli* W3110 strain 9E4, which has the complete genotype tonA ptr3; *E coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan; *E. coli* W3110 strain 40B4, which is strain 37D6 with a non-kanamycin resistant degP deletion mutation; and an *E. coli* strain having mutant periplasmic protease disclosed in U.S. Pat. No. 4,946,83 issued 7 Aug. 1990.

In addition to prokaryotes, eukaryotic microbes such as filamentous fungi or yeast are suitable cloning or expression hosts for insulin or insulin variant encoding vectors. *Saccharomyces cerevisiae* is a commonly used lower eukaryotic host microorganism. Others include *Schizosaccharomyces pombe* (Beach and Nurse, *Nature* 290: 140 (1981); EP 139,383 published 2 May 1985); Kluveromyces hosts (U.S. Pat. No. 4,943,529; Fleer et al., *Bio/Technology* 9: 968-975 (1991)) such as, e.g., *K. lactis* (MW98-8C, CBS683, CBS4574; Louvencourt et al., *J. Bacteriol.* 154(2): 737 (1983); *K. fragilis* (ATCC 12,424), *K. bulgaricus* (ATCC 16,045), *K. wicheramii* (ATCC 24,178), *K. waltii* (ATCC 56,500), *K. drosophilarum* (ATCC 36,906); Van den Berg et al., *Bio/Technology* 8: 135 (1990)), *K. thermotolerans*, and *K. marxianus; yarrowia* (EP 402,226); *Pichia pastoris* (EP 183,070); Sreekrishna et al., *J. Basic Microbiol.* 28: 265-278 (1988); *Candida; Trichoderma reesia* (EP 244,234); *Neurospora crassa* (Case et al., *Proc. Natl. Acad. Sci. USA*, 76:5259-5263 (1979); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al, *Biochem. Biophys. Res. Commun.* 112: 284-289(1983); Tilburn et al., *Gene*, 26: 205-221 (1983); Yelton et al., *Proc. Natl. Acad. Sci. USA* 81: 1470-1474 (1984)) and *A. niger* (Kelly and Hynes, *EMBO J.* 4: 475-479 (1985)). Methylotropic yeasts are suitable herein and include, but are not limited to, yeast capable of growth on methanol selected from the genera consisting of *Hansenula, Cadida, Kloeckera, Pichia, Saccharomyces, Torulopsis*, and *Rhodotorula*. A list of specific species that are exemplary of this class of yeasts may be found in C. Anthony, *The Biochemistry of Methylotrophs* 269 (1982).

Suitable host cells for the expression of glycosylated insulin and insulin variant polypeptides can be derived from multicellular organisms. Examples of invertebrate cells include insect cells such as Drosophila S2 and Spodoptera Sf9 and high five, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding insulin or insulin variants may be inserted into a replicable vector for cloning (amplification of the DNA) or for expression. Various vectors are publicly available. The vector may, for example, be in the form of a plasmid, cosmid, viral particle, phagemid or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The insulin or insulin variant polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the insulin or insulin variant-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010, 182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli.*

An example of suitable selectable markers for mammalian cells are those that enable the identification of cells competent to take up the nucleic acid encoding the polypeptide of the invention, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7. Stinchcomb et al., *Nature,* 282:39 (1979); Kingsman et al., *Gene,* 7:141 (1979); Tschemper et al, *Gene,* 10:157 (1980). The trp1 gene provides a selection marker for a mutant strain of yeast lacking the ability to grow in tryptophan, for example, ATCC No. 44076 or PEP4-1. Jones, *Genetics,* 85:12 (1977).

Expression and cloning vectors usually contain a promoter operably linked to the insulin-encoding nucleic acid sequence to direct mRNA synthesis. Promoters recognized by a variety of potential host cells are well known. Promoters suitable for use with prokaryotic hosts include the β-lactamase and lactose promoter systems; Chang et al., *Nature,* 275:615 (1978); Goeddel et al., *Nature,* 281:544 (1979); alkaline phosphatase, a tryptophan (trp) promoter system, Goeddel, *Nucleic Acids Res.,* 8:4057 (1980); EP 36,776; and hybrid promoters such as the tac promoter, deBoer et al., *Proc. Natl. Acad. Sci. USA,* 80:21-25 (1983). Promoters for use in bacterial systems also will contain a Shine-Dalgarno (S.D.) sequence operably linked to the DNA encoding the insulin or insulin variant polypeptide of the invention.

Examples of suitable promoting sequences for use with yeast hosts include the promoters for 3-phosphoglycerate kinase, Hitzeman et al., *J. Biol. Chem.,* 255:2073 (1980) or other glycolytic enzymes, Hess et al., *J. Adv. Enzyme Reg.,* 7:149 (1968); Holland, *Biochemistry,* 17:4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Expression from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the polypeptides employable with the invention by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the insulin or insulin variant coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptides of the invention.

Still other methods, vectors, and host cells suitable for adaptation to the synthesis of the polypeptides of the invention in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification or expression may be measured in a sample directly, for example, by conventional Southern blotting or Northern blotting or RT-PCR (Taqman) to quantitate the transcription of mRNA, Thomas, *Proc. Natl. Acad. Sci. USA,* 77:5201-5205 (1980), dot blotting (DNA or RNA analysis), or in situ hybridization, using an appropriately labeled probe, based on the sequences provided herein.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence insulin or insulin variant polypeptide or against a synthetic peptide based on the DNA sequences provided herein or against exogenous sequence fused to insulin or insulin variant DNA encoding the polypeptide of the invention and encoding a specific antibody epitope.

5. Purification of Polypeptide

Forms of the polypeptides employable with the present invention may be recovered from culture medium or from host cell lysates. If membrane-bound, they can be released from the membrane using a suitable detergent solution (e.g. Triton®-X 100) or by enzymatic cleavage. Cells employed in expression of the polypeptide employable with the invention can be disrupted by various physical or chemical means, such as freeze-thaw cycling, sonication, mechanical disruption, or cell lysing agents.

It may be desired to purify insulin or insulin. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the polypeptide of the invention. Various methods of protein purification may be employed and such methods are known in the art and described for example in Deutscher, *Methods in Enzymology,* 182 (1990); Scopes, *Protein Purification: Principles and Practice,* Springer-Verlag, New York (1982). The purification step(s) selected will depend, for example, on the nature of the production process used and the particular insulin or insulin variant produced.

6. Tissue Distribution

The location of tissues expressing the polypeptides employable with the invention can be identified by determining mRNA expression in various human tissues. Such data may help determine which tissues are most likely to be affected by the stimulating and inhibiting activities of the polypeptides of the invention. Tissue which expresses and responds to insulin could in theory be used in the activity blocking assays discussed below.

As noted before, gene expression in various tissues may be measured by conventional Northern blotting, RT-PCR (Taqman), Thomas, *Proc. Natl. Acad. Sci. USA,* 77:5201-5205 [1980], dot blotting, or in situ hybridization, using an appropriately labeled probe, based on the sequences provided herein. Alternatively, gene expression can be measured by immunological methods, such as immunohistochemical staining of tissue sections and assay of cell culture or body fluids, as described above under 4. Detecting Gene Amplification/Expression.

E. Pharmaceutical Compositions and Dosages

The insulin and insulin variant polypeptides employable with the methods of the invention can be administered for the treatment of cartilaginous disorders in the form of pharmaceutical compositions. Additionally, lipofections or liposomes can also be used to deliver the insulin or insulin variant into cells and the target area.

Therapeutic formulations of the active molecules employable with the invention are prepared for storage by mixing the active molecule having the desired degree of purity with optional pharmaceutically acceptable carriers, excipients or stabilizers (*Remington's Pharmaceutical Sciences* 16th edition, Osol, A. Ed. [1980]). Such therapeutic formulations can be in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, dextrins, or hyaluronan; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as TWEEN®, PLURONICS® or polyethylene glycol (PEG).

In order for the formulations to be used in vivo administration, they must be sterile. The formulation may be readily rendered sterile by filtration through sterile filtration membranes, prior to or following lyophilization and reconstitution. The therapeutic compositions herein generally are placed into a container having a sterile access port, for example, an intravenous solution bag or vial having a stopper pierceable by a hypodermic injection needle.

The formulations used herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are present in combinations and amounts that are effective for the intended purpose.

The route of administration is in accordance with known methods, e.g., injection or infusion by intravenous, intraperitoneal, intramuscular, intraarterial, intralesional or intraarticular routes, topical administration, by sustained release or extended-release means. Optionally the active compound or formulation is injected directly into the afflicted cartilaginous region or articular joint.

The insulin or insulin variant molecules by also be prepared by entrapping in microcapsules prepared, for example by coacervation techniques or by interfacial polymerization, for example, hydroxymethylcellulose or gelatin-microcapsules and poly-(methylmethacrylate) microcapsules, respectively. Such preparations can be administered in colloidal drug delivery systems (for example, liposomes, albumin microspheres, microemulsions, nano-particles and nanocapsules) or in macroemulsions. Such techniques are disclosed in *Remington's Pharmaceutical Sciences,* 16th Edition (or newer), Osol A. Ed. (1980).

Where sustained-release or extended-release administration of the insulin or insulin variant polypeptides is desired in a formulation with release characteristics suitable for the treatment of any disease or disorder requiring administration of such polypeptides, microencapsulation is contemplated. Microencapsulation of recombinant proteins for sustained release has been successfully performed with human growth hormone (rhGH), interferon-$\alpha$, -$\beta$, -$\gamma$ (rhIFN-$\alpha$, -$\beta$, -$\gamma$), interleukin-2, and MN rgp120. Johnson et al., *Nat. Med.* 2: 795-799 (1996); Yasuda, *Biomed. Ther.* 27: 1221-1223 (1993); Hora et al., *Bio/Technology* 8: 755-758 (1990); Cleland, "Design and Production of Single Immunization Vaccines Using Polylactide Polyglycolide Microsphere Systems" in *Vaccine Design: The Subunit and Adjuvant Approach,* Powell and Newman, eds., (Plenum Press: New York, 1995), pp. 439-462; WO 97/03692, WO 96/40072, WO 96/07399 and U.S. Pat. No. 5,654,010.

Suitable examples of sustained-release preparations include semipermeable matrices of solid hydrophobic polymers containing the active molecule, which matrices are in the form of shaped articles, e.g. films, or microcapsules. Examples of sustained-release matrices include one or more polyanhydrides (e.g., U.S. Pat. Nos. 4,891,225; 4,767,628), polyesters such as polyglycolides, polylactides and polylactide-co-glycolides (e.g., U.S. Pat. Nos. 3,773,919; 4,767, 628; 4,530,840; Kulkarni et al., *Arch. Surg.* 93: 839 (1966)), polyamino acids such as polylysine, polymers and copolymers of polyethylene oxide, polyethylene oxide acrylates, polyacrylates, ethylene-vinyl acetates, polyamides, polyurethanes, polyorthoesters, polyacetylnitriles, polyphosphazenes, and polyester hydrogels (for example, poly(2- hydroxyethyl-methacrylate), or poly(vinylalcohol)), cellulose, acyl substituted cellulose acetates, non-degradable polyurethanes, polystyrenes, polyvinyl chloride, polyvinyl fluoride, poly(vinylimidazole), chlorosulphonated polyolefins, polyethylene oxide, copolymers of L-glutamic acid and γ-ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. Additional non-biodegradable polymers which may be employed are polyethylene, polyvinyl pyrrolidone, ethylene vinylacetate, polyethylene glycol, cellulose acetate butyrate and cellulose acetate propionate.

Alternatively, sustained release formulations may be composed of degradable biological materials. Biodegradable polymers are attractive drug formulations because of their biocompatibility, high responsibility for specific degradation, and ease of incorporating the active drug into the biological matrix. For example, hyaluronic acid (HA) may be crosslinked and used as a swellable polymeric delivery vehicle for biological materials. U.S. Pat. No. 4,957,744; Valle et al., *Polym. Mater. Sci. Eng.* 62: 731-735 (1991). HA polymer grafted with polyethylene glycol has also been prepared as an improved delivery matrix which reduced both undesired drug leakage and the denaturing associated with long term storage at physiological conditions. Kazuteru, M., *J. Controlled Release* 59:77-86 (1999). Additional biodegradable polymers which may be used are poly(caprolactone), polyanhydrides, polyamino acids, polyorthoesters, polycyanoacrylates, poly(phosphazines), poly(phosphodiesters), polyesteramides, polydioxanones, polyacetals, polyketals, polycarbonates, polyorthocarbonates, degradable and nontoxic polyurethanes, polyhydroxylbutyrates, polyhydroxyvalerates, polyalkylene oxalates, polyalkylene succinates, poly(malic acid), chitin and chitosan.

Alternatively, biodegradable hydrogels may be used as controlled release delivery vehicles for biological materials and drugs. Through the appropriate choice of macromers, membranes can be produced with a range of permeability, pore sizes and degradation rates suitable for a wide variety of biomolecules.

Alternatively, sustained-release delivery systems for biological materials and drugs can be composed of dispersions. Dispersions may further be classified as either suspensions or emulsions. In the context of delivery vehicles for biological materials, suspensions are a mixture of very small solid particles which are dispersed (more or less uniformly) in a liquid medium. The solid particles of a suspension can range in size from a few nanometers to hundreds of microns, and include microspheres, microcapsules and nanospheres. Emulsions, on the other hand, are a mixture of two or more immiscible liquids held in suspension by small quantities of emulsifiers. Emulsifiers form an interfacial film between the immiscible liquids and are also known as surfactants or detergents. Emulsion formulations can be both oil in water (o/w) wherein water is in a continuous phase while the oil or fat is dispersed, as well as water in oil (w/o), wherein the oil is in a continuous phase while the water is dispersed. One example of a suitable sustained-release formulation is disclosed in WO 97/25563. Additionally, emulsions for use with biological materials include multiple emulsions, microemulsions, microdroplets and liposomes. Microdroplets are unilamellar phospholipid vesicles that consist of a spherical lipid layer with an oil phase inside. E.g., U.S. Pats. No. 4,622,219 and 4,725,442. Liposomes are phospholipid vesicles prepared by mixing water-insoluble polar lipids with an aqueous solution.

Alternatively, the sustained-release formulations of insulin or insulin variant polypeptides may be developed using poly-lactic-coglycolic acid (PLGA), a polymer exhibiting a strong degree of biocompatibility and a wide range of biodegradable properties. The degradation products of PLGA, lactic and glycolic acids, are cleared quickly from the human body. Moreover, the degradability of this polymer can be adjusted from months to years depending on its molecular weight and composition. For further information see Lewis, "Controlled Release of Bioactive Agents from Lactide/Glycolide polymer," in *Biogradable Polymers as Drug Delivery Systems* M. Chasin and R. Langeer, editors (Marcel Dekker: New York, 1990), pp. 141.

When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The encapsulated polypeptides or polypeptides in extended-release formulation may be imparted by formulating the polypeptide with a "water-soluble polyvalent metal salts" which are non-toxic at the release concentration and temperature. Exemplary "polyvalent metals" include the following cations: $Ca^{2+}$, $Mg^{2+}$, $Zn^{2+}$, $Fe^{2+}$, $Fe^{3+}$, $Cu^{2+}$, $Sn^{2+}$, $Sn^{4+}$, $Al^{2+}$ and $Al^{3+}$. Exemplary anions which from water soluble salts with the above polyvalent metal cations include those formed by inorganic acids and/or organic acids. Such water-soluble salts have a solubility in water (at 20° C.) of at least about 20 mg/ml, alternatively 100 mg/ml, alternatively 200 mg/ml.

Suitable inorganic acids that can be used to form the "water soluble polyvalent metal salts" include hydrochloric, sulfuric, nitric, thiocyanic and phosphoric acid. Suitable organic acids that can be used include aliphatic carboxylic acid and aromatic acids. Aliphatic acids within this definition may be defined as saturated or unsaturated $C_{2-9}$ carboxylic acids (e.g., aliphatic mono-, di- and tri-carboxylic acids). For example, exemplary monocarboxylic acids within this definition include the saturated $C_{2-9}$ monocarboxylic acids acetic, proprionic, butyric, valeric, caproic, enanthic, caprylic pelargonic and capryonic, and the unsaturated $C_{2-9}$ monocarboxylic acids acrylic, propriolic methacrylic, crotonic and isocrotonic acids. Exemplary dicarboxylic acids include the saturated $C_{2-9}$ dicarboxylic acids malonic, succinic, glutaric, adipic and pimelic, while unsaturated $C_{2-9}$ dicarboxylic acids include maleic, fumaric, citraconic and mesaconic acids. Exemplary tricarboxylic acids include the saturated $C_{2-9}$ tricarboxylic acids tricarballylic and 1,2,3-butanetricarboxylic acid. Additionally, the carboxylic acids of this definition may also contain one or two hydroxyl groups to form hydroxy carboxylic acids. Exemplary hydroxy carboxylic acids include glycolic, lactic, glyceric, tartronic, malic, tartaric and citric acid. Aromatic acids within this definition include benzoic and salicylic acid.

Commonly employed water soluble polyvalent metal salts which may be used to help stabilize the encapsulated polypeptides of this invention include, for example: (1) the inorganic acid metal salts of halides (e.g., zinc chloride, calcium chloride), sulfates, nitrates, phosphates and thiocyanates; (2) the aliphatic carboxylic acid metal salts calcium acetate, zinc acetate, calcium proprionate, zinc glycolate, calcium lactate, zinc lactate and zinc tartrate; and (3) the aromatic carboxylic acid metal salts of benzoates (e.g., zinc benzoate) and salicylates.

Dosages and desired drug concentrations of pharmaceutical compositions employable with the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" in *Toxicokinetics and New Drug Development*, Yacobi et al., Eds., Pergamon Press, New York 1989, pp. 42-96.

When in vivo administration of insulin or insulin variant polypeptides are employed, normal dosage amounts may vary from about 10 ng/kg up to about 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344 or 5,225,212. It is anticipated that different formulations will be effective for different treatments and different disorders, and that administration intended to treat a specific organ or tissue, may necessitate delivery in a manner different from that to another organ or tissue.

F. Methods of Treatment

It is contemplated that the polypeptides, antibodies and other active compounds of the present invention may be used to treat various cartilaginous disorders. Exemplary conditions or disorders to be treated with the polypeptides of the invention, include, but are not limited to systemic lupus erythematosis, rheumatoid arthritis, juvenile chronic arthritis, osteoarthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

In systemic lupus erythematosus, the central mediator of disease is the production of auto-reactive antibodies to self proteins/tissues and the subsequent generation of immune-mediated inflammation. These antibodies either directly or indirectly mediate tissue injury. Although T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that affects the synovial membrane of multiple joints and which results in injury to the articular cartilage. The pathogenesis is T lymphocyte dependent and is associated with the production of rheumatoid factors, auto-antibodies directed against endogenous proteins, with the resultant formation of immune complexes that attain high levels in joint fluid and blood. These complexes may induce infiltration by lymphocytes, monocytes, and neutrophils into the synovial compartment. Tissues affected are primarily the joints, often in symmetrical pattern. However, disease outside the joints occurs in two major forms. In one form, typical lesions are pulmonary fibrosis, vasculitis, and cutaneous ulcers. The second form is the so-called Felty's syndrome which occurs late in the RA disease course, sometimes after joint disease has become quiescent, and involves the presence of neutropenia, thrombocytopenia and splenomegaly. This can be accompanied by vasculitis in multiple organs and occurrence of infarcts, skin ulcers and gangrene. Patients often also develop rheumatoid nodules in the subcutis tissue overlying affected joints; in late stages, the nodules have necrotic centers surrounded by a mixed inflammatory cellular infiltrate. Other manifestations which can occur in RA include: pericarditis, pleuritis, coronary arteritis, intestitial pneumonitis with pulmonary fibrosis, keratoconjunctivitis sicca, and rheumatoid nodules.

Juvenile chronic arthritis is a chronic idiopathic inflammatory disease which begins often at less than 16 years of age and which has some similarities to RA. Some patients which are rheumatoid factor positive are classified as juvenile rheumatoid arthritis. The disease is sub-classified into three major categories: pauciarticular, polyarticular, and systemic. The arthritis can be severe and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing sponylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+T lymphocyte, a cell which targets antigen presented by class I MHC molecules. CD8+T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin which is likely induced by an active inflammatory process. Scleroderma can be localized or systemic. Vascular lesions are common, and endothelial cell injury in the microvasculature is an early and important event in the development of systemic sclerosis. An immunologic basis is implied by the presence of mononuclear cell infiltrates in the cutaneous lesions and the presence of anti-nuclear antibodies in many patients. ICAM-1 is often upregulated on the cell surface of fibroblasts in skin lesions suggesting that T cell interaction with these cells may have a role in the pathogenesis of the disease. Other organs may also be involved. In the gastrointestinal tract, smooth muscle atrophy and fibrosis can result in abnormal peristalsis/motility. In the kidney, concentric subendothelial intimal proliferation affecting small arcuate and interlobular arteries can result in reduced renal cortical blood flow and thus proteinuria, azotemia and hypertension. In skeletal and cardiac muscle, atrophy, interstitial fibrosis/scarring, and necrosis can occur. Finally, the lung can have interstitial pneumonitis and interstitial fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components involved in protein synthesis.

Sjögren's syndrome is the result of immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including biliary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc, particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Diabetes mellitus is a genetic disorder of metabolism of carbohydrate, protein and fat associated with a relative or absolute insufficiency of insulin secretion and with various degrees of insulin resistance. In its fully developed clinical expression, it is characterized by fasting hyperglycemia and in the majority of long-standing patients by atherosclerotic and microangiopathic vascular disease and neuropathy. Differences between various forms of the disease are expressed in terms of cause and pathogenesis, natural history, and response to treatment. Thus, diabetes is not a single disease but a syndrome.

Type I, or insulin-dependent diabetes mellitus (IDDM) occurs in approximately 10 percent of all diabetic patients in the Western world. Type I diabetes mellitus or insulin-dependent diabetes is the autoimmune destruction of pancreatic islet β-cells; this destruction is mediated by autoantibodies and auto-reactive T cells. Antibodies to insulin or the insulin receptor can also produce the phenotype of insulin-non-responsiveness.

Classically, this type of disease occurs most commonly in childhood and adolescence; however, it can be recognized and become symptomatic at any age. In the most common type of IDDM (Type IA), it has been postulated that environmental (acquired) factors such as certain viral infections, and possibly chemical agents, superimposed on genetic factors, may lead to cell-mediated autoimmune destruction of β cells. Thus, genetically determined abnormal immune responses (linked to HLA associations) characterized by cell mediated and humoral autoimmunity are thought to play a pathogenetic role after evocation by an environmental factor. A second type of IDDM (Type IB) is believed to be due to primary autoimmunity. These patients have associated autoimmune endocrine diseases such as Hashimoto's thyroiditis, Graves' disease, Addison's disease, primary gonadal failure, and associated nonendocrine autoimmune diseases such as pernicious anemia, connective tissue diseases, celiac disease and myasthenia gravis. Insulin dependency implies that administration of insulin is essential to prevent spontaneous ketosis, coma, and death. However, even with insulin treatment, diabetic patients can still have many of the additional problems associated with diabetes, i.e. connective tissue disorders, neuropathy, etc.

The second type of diabetes, Type II or non-insulin-dependent diabetes mellitus (NIDDM), present in approximately 90% of all diabetics, also has a genetic basis. Patients with type II diabetes may have a body weight that ranges from normal to excessive. Obesity and pathological insulin resistance are by no means essential in the evolution of NIDDM. In the majority of patients with NIDDM, a diagnosis is made in middle age. Patients with NIDDM are non-insulin-dependent for prevention of ketosis, but they may require insulin for correction of symptomatic or non-symptomatic persistent fasting hyperglycemia if this cannot bye achieved with the use of diet or oral agents. Thus, therapeutic administration of insulin does not distinguish between IDDM and NIDDM. In some NIDDM families, the insulin secretory responses to glucose are so low that they may resemble those of early Type I diabetes at any point in time. Early in its natural history, the insulin secretory defect and insulin resistance may be reversible by treatment (ie. weight reduction) with normalization of glucose tolerance. The typical chronic complications of diabetes, namely macroangiopathy, microangiopathy, neuropathy, and cataracts seen in IDDM are seen in NIDDM as well.

Other types of diabetes include entities secondary to or associated with certain other conditions or syndromes. Diabetes may be secondary to pancreatic disease or removal of pancreatic tissue; endocrine diseases such as acromegaly, Cushing's syndrome, pheochromocytoma, glucagonoma, somatostatinoma, or primary aldosteronism; the administration of hormones, causing hyperglycemia; and the administration of certain drugs (i.e. antihypertensive drugs, thiazide diuretics, preparations containing estrogen, psychoactive drugs, sympathomimetic agents). Diabetes may be associated with a large number of genetic syndromes. Finally, diabetes may be associated with genetic defects of the insulin receptor or due to antibodies to the insulin receptor with or without associated immune disorders.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including multiple sclerosis; idiopathic demyelinating polyneuropathy or Guillain-Barre syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+T lymphocytes are the predominant cell type at lesions. The mechanism of oligodendrocyte cell death and subsequent demyelination is not known but is likely T lymphocyte driven.

Inflammatory and fibrotic lung disease, including eosinophilic pneumonias, idiopathic pulmonary fibrosis, and hypersensitivity pneumonitis may involve a disregulated immune-inflammatory response. Inhibition of that response would be of therapeutic benefit and within the scope of the invention.

Autoimmune or immune-mediated skin disease, including bullous skin diseases, erythema multiforme, and contact dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Transplantation associated diseases, including Graft rejection and Graft-Versus-Host-Disease (GVHD) are T lymphocyte-dependent; inhibition of T lymphocyte function is ameliorative.

Other diseases in which intervention of the immune and/or inflammatory response have benefit are infectious disease including but not limited to viral infection (including but not limited to AIDS, hepatitis A, B, C, D, E and herpes) bacterial infection, fungal infections, and protozoal and parasitic infections (molecules (or derivatives/agonists) which stimulate the MLR can be utilized therapeutically to enhance the immune response to infectious agents), diseases of immunodeficiency (molecules/derivatives/agonists) which stimulate the MLR can be utilized therapeutically to enhance the immune response for conditions of inherited, acquired, infectious induced (as in HIV infection), or iatrogenic (i.e. as from chemotherapy) immunodeficiency, and neoplasia.

Additionally, inhibition of molecules with proinflammatory properties may have therapeutic benefit in reperfusion injury; stroke; myocardial infarction; atherosclerosis; acute lung injury; hemorrhagic shock; burn; sepsis/septic shock; acute tubular necrosis; endometriosis; degenerative joint disease and pancreatis.

The compounds of the present invention, e.g. polypeptides or antibodies, are administered to a mammal, preferably a human, in accord with known methods, such as intravenous administration as a bolus or by continuous infusion over a period of time, by intramuscular, intraperitoneal, intracerebrospinal, subcutaneous, intra-articular, intrasynovial, intrathecal, oral, topical, or inhalation (intranasal, intrapulmonary) routes.

It may be desirable to also administer antibodies against other immune disease associated or tumor associated antigens, such as antibodies which bind to CD20, CD11a, CD 40, CD18, ErbB2, EGFR, ErbB3, ErbB4, or vascular endothelial growth factor (VEGF). Alternatively, or in addition, two or more antibodies binding the same or two or more different antigens disclosed herein may be coadministered to the patient. Sometimes, it may be beneficial to also administer one or more cytokines to the patient. In one embodiment, the polypeptides of the invention are coadministered with a growth inhibitory agent. For example, the growth inhibitory agent may be administered first, followed by a polypeptide of the invention. However, simultaneous administration or administration first is also contemplated. Suitable dosages for the growth inhibitory agent are those presently used and may be lowered due to the combined action (synergy) of the growth inhibitory agent and the polypeptide of the invention.

For the treatment or reduction in the severity of immune related disease, the appropriate dosage of an a compound of the invention will depend on the type of disease to be treated, as defined above, the severity and course of the disease, whether the agent is administered for preventive or therapeutic purposes, previous therapy, the patient's clinical history and response to the compound, and the discretion of the attending physician. The compound is suitably administered to the patient at one time or over a series of treatments.

For example, depending on the type and severity of the disease, about 1 μg/kg to 15 mg/kg (e.g. 0.1-20 mg/kg) of polypeptide or antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

G. Articles of Manufacture

In another embodiment of the invention, an article of manufacture containing materials useful for the diagnosis or treatment of the disorders described above is provided. The article of manufacture comprises a container and an instruction. Suitable containers include, for example, bottles, vials, syringes, and test tubes. The containers may be formed from a variety of materials such as glass or plastic. The container holds a composition which is effective for diagnosing or treating the cartilaginous disorder, and may have a sterile access port (for example the container may be an intravenous solution bag or a vial having a stopper pierceable by a hypodermic injection needle). The active agent in the composition will typically be an insulin or insulin variant polypeptide. The composition can comprise any or multiple ingredients disclosed herein. The instruction on, or associated with, the container indicates that the composition is used for diagnosing or treating the condition of choice. For example, the instruction could indicate that the composition is effective for the treatment of osteoarthritis, rheumatoid arthritis or any other cartilaginous disorder. The article of manufacture may further comprise a second container comprising a pharmaceutically-acceptable buffer, such as phosphate-buffered saline, Ringer's solution and dextrose solution. Alternatively, the composition may contain any of the carriers, excipients and/or stabilizers mentioned herein under section *E. Pharmaceutical Compositions and Dosages*. It may further include other materials desirable from a commercial and user standpoint, including other buffers, diluents, filters, needles, syringes, and package inserts with instructions for use.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., *Molecular Cloning: A Laboratory Manual*, Cold Spring Harbor Press N.Y., 1989; Ausubel et al., *Current Protocols in Molecular Biology*, Green Publishing Associates and Wiley Interscience, N.Y., 1989; Innis et al., *PCR Protocols: A Guide to Methods and Applications*, Academic Press, Inc., N.Y., 1990; Harlow et al., *Antibodies: A Laboratory Manual*, Cold Spring Harbor Press, Cold Spring Harbor, 1988; Gait, M. J., *Oligonucleotide Synthesis*, IRL Press, Oxford, 1984; R. I. Freshney, *Animal Cell Culture*, 1987; Coligan et al., *Current Protocols in Immunology*, 1991.

Example 1

Effect on Insulin on Primary Articular Chondrocytes

Introduction

This experiment shows the effect of various concentrations (0.1-100 nM) of insulin on matrix (proteoglycan) synthesis and on viability of chondrocytes in serum-free culture media. In order to culture chondrocytes, articular cartilage is digested with enzymes which remove the extracellular matrix. Thus, the cellular environment in this culture system may be similar to that found in later stages of cartilage disorders where the matrix has been depleted. Since essentially all of the matrix synthesized by chondrocytes cultured in monolayer is secreted into the media, the amount of proteoglycans in the media of such cells is indicative of matrix synthesis. Proteoglycans are measured in media using the 1,9-dimethylmethylene blue (DMMB) colorimetric assay of Farndale and Buttle, *Biochim. Biophys. Acta* 883: 173-177 (1986). In this assay, the change in color of the DMMB dye which occurs upon its binding to proteoglycans is quantitated spectrophotometrically. Chondrocyte viability was determined using a colorimetric assay that measures the metabolic activity of cultured cells based on the ability of viable cells to cleave the yellow tetrazolium salt MTT to form purple formazan crystals Berridge, M. V. & Tan, A. S., *Arch. Biochem. Biophys.* 303: 474 (1993). The formazan crystals formed are solubilized and spectrophotometrically quantitated using an ELISA reader.

Materials and Methods

Chondrocyte Preparation:

The metacarpophalangeal joints of 4-6 month old female pigs were aseptically dissected, and articular cartilage was removed by free-hand slicing taking care so as to avoid the underlying bone. These cartilage fragments were then digested in 0.05% trypsin in serum-free Ham's F12 for 25 minutes at 37° C. The medium was drained and discarded, and cartilage was digested in 0.3% collagenase B in serum-free Ham's F12 media for thirty minutes at 37° C. The medium was drained and discarded, and the cartilage was digested overnight in 0.06% collagenase B in Ham's F12+

10% fetal bovine serum. The cells were then filtered through a 70 micron nylon filter and seeded in Ham's F12 medium without serum.

Culturing of Chondrocytes:

Chondrocytes (prepared as described above) were grown in microtiter plates (Falcon microtest 96, flat bottom) at a density of 80,000 cells per well in media composed of Ham's F12 with antibiotics (10 µg/ml gentamicin, 250 ng/ml amphotericin B, 100 µg/ml penicillin/streptomycin) in a final volume of 250 µl per well, for 6 days at 37° C. and 5% $CO_2$. Media was removed and used to measure proteoglycans at days 3 and 6.

Measurement of Proteoglycans:

DMMB is a dye that undergoes metachromasia (a change in color, in this case from blue to purple) upon binding to sulfated glycosaminoglycans (GAG), the side-chains of proteoglycans. The addition of sulfated proteoglycans to DMMB causes a decrease in the peak values at 590 and 660 nm with an increase in absorbance at 530 nm. Thus, the amount of proteoglycans in media was determined by adding DMMB dye in a 96 well plate format, and the change in color was quantitated using a spectrophotometer (Spectramax 250). The DMMB assay is a well-accepted method to measure the amount of proteoglycans in cartilage cultures. For this assay, a standard curve was prepared using chondroitin sulfate ranging from 0.0 to 5.0 µg.

MTT Assay:

After 6 days of treatment, 10 ul of the tetrazolium salt, MTT (stock 5 mg/ml), (Boehringer Mannheim, cat. No.1465007) was added to the remaining 100 µl of media in each well. After another 4 hour incubation at 37° C. and 5% $CO_2$, 100 µl solubilization solution (reagent in assay kit from Boehringer Mannheim) was added and the plate was incubated overnight at 37° C. and 5% $CO_2$. The absorbance was then measured at 584 nm (and at 690 nm to determine background absorbance).

Results and Discussion

As show in FIG. 1, insulin increased synthesis of proteoglycans in a dose-dependent manner. In addition, insulin (at concentrations as low as 0.1 nM) inhibited the down-regulation of PG synthesis induced by IL-1α (right side of graph in FIG. 1). Thus, insulin (Intergen, Purchase, New York, cat. no. 450100) was a very potent stimulator of proteoglycan synthesis, and was able overcome the inhibitory effects of IL-1α (R&D Systems, cat. no. 200LA002) on proteoglycan synthesis.

Figure 2:
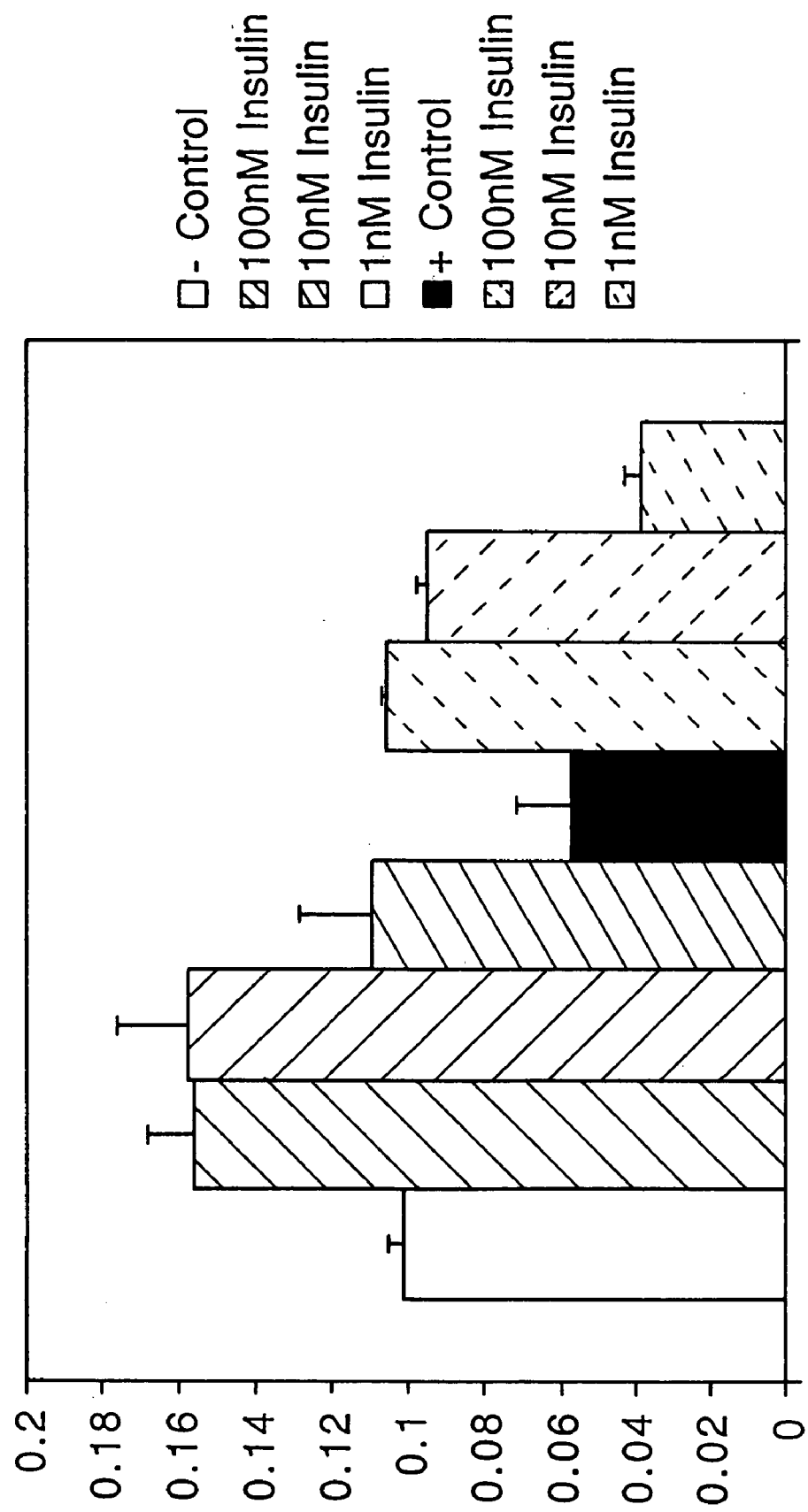
FIG. 2 shows insulin treatment over an extended period of time (6 days) at various concentrations (1-100 nM) in serum-free media resulted in increased metabolism of primary articular chondrocytes as determined by a colorimetric assay which measures metabolic activity of cultured cells based on the ability of viable cells to cleave the yellow tetrazolium salt MTT to form purple formazan crystals.

Unlike most primary cells, chondrocytes are able to survive in serum-free media in the absence of any additional growth factors for at least one week. However, addition of insulin (at 100 nM and 10 nM) increased the metabolic activity of chondrocytes cultured in this way for 6 days (FIG. 2). Insulin also blocked the ability of interleukin 1-α to inhibit the metabolic activity of chondrocytes (right half of graph). Such an activity could be very useful therapeutically, especially in conditions such as arthritis, joint trauma, or aging, where the metabolic activity of chondrocytes is compromised.

The ability of insulin to counteract the detrimental effects of IL1-α makes insulin a very attractive candidate for the treatment of conditions such as arthritis in which high levels of IL-1 are implicated in disease progression.

Example 2

Articular Cartilage Explant Assay

Introduction

The experiments of this example examine both the synthetic and prophylactic potential of the test compound on cartilage matrix turnover. This potential is determined by measuring matrix (i.e proteoglycan) synthesis and breakdown, as well as nitric oxide production, in articular cartilage. These parameters are evaluated in the presence and absence of interleukin 1α, IL-1α. Articular cartilage explants have several advantages over primary cells in culture. First, and perhaps most importantly, cells in explants remain embedded in tissue architecture produced in vivo. Secondly, these explants are phenotypically stable for several weeks ex vivo, during which time they are able to maintain tissue homeostasis. Finally, unlike primary cells, explants can be used to measure matrix breakdown. To set up cartilage explants, articular cartilage must be dissected and minced which results in disruption of the collagen network and release of proteoglycans into the culture media. This system thus mimics degenerative conditions such as arthritis in which the matrix is progressively depleted. Using this system, we have found that the test compound can: (1) stimulate proteoglycan (PG) synthesis; (2) inhibit PG release; (3) inhibit IL-1α-induced PG breakdown; (4) inhibit the IL-1α-induced reduction in PG synthesis; and (5) decrease both basal and IL-1α-induced nitric oxide production.

Il-1α has catabolic effects on cartilage including up-regulation of enzymes which induce matrix breakdown (matrix metalloproteinases and aggrecanases) as well as inhibition of synthesis of new matrix molecules (proteoglycans and collagens). Thus, the ability of the test compound to not only have positive effects on cartilage, but to also counteract the deleterious effects of IL-1α is strong evidence of the protective effect exhibited by the test compound. In addition, such an activity suggests that the test compound could inhibit the degradation which occurs in arthritic conditions, since high levels of IL-1 are found in arthritic joints, and since antagonism of IL-1 function has been shown to reduce the progression of osteoarthritis. Arend W. P. et al., Ann. Rev. Immunol. 16: 27-55 (1998).

The role of nitric oxide (NO) in the breakdown of articular cartilage, especially the destruction associated with osteoarthritis has been described (Ashok et al., Curr. Opin. Rheum. 10: 263-268 (1998)). In vivo animal models suggest that inhibition of nitric oxide production reduces progression of arthritis (Pelletier, J P et al., Arthritis Rheum. 7: 1275-86 (1998); van de Loo et al., Arthritis Rheum. 41: 634-46 (1998); Stichtenoth, DO and Frolich J. C., Br. J. Rheumatol. 37: 246-57 (1998). In humans, many of the drugs used to treat rheumatoid arthritis can decrease nitric oxide production or activity. Since NO also has effects on cell types besides chondrocytes, the presence of NO within the joint may also increase vasodilation and permeability, potentiate cytokine release by leukocytes, and stimulate angiogenic activity. Because production of NO by cartilage correlates with disease state, and since NO appears to play a role in both erosive and inflammatory components of joint diseases, a factor which decreases nitric oxide production would likely be beneficial in the treatment of cartilaginous disorders.

The assay for nitric oxide described herein is based on the principle that 2,3-diaminonapthalene (DAN) reacts with nitrite under acidic conditions to form 1-(H)-naphthotriazole, a fluorescent product. As NO is quickly metabolized into nitrite ($NO_2^{-1}$) and nitrate ($NO_3^{-1}$), detection of nitrite is one means of detecting (albeit undercounting) the actual NO produced in cartilaginous tissue.

Materials and Methods

Articular Cartilage Explants:

The metacarpophalangeal joint of 4-6 month old female pigs was aseptically dissected as described above. The cartilage was minced, washed and cultured in bulk for at least 24 hours at 37° C. and 5% $CO_2$ in explant media, i.e. serum free (SF) LG DMEM/F12 media with 0.1% BSA, 100 U/ml penicillin/streptomycin (Gibco), 2 mM L-Glutamine, 0.1 mM sodium pyruvate (Gibco), 20 µg/ml Gentamicin (Gibco) and 1.25 mg/L Amphotericin B. Articular cartilage was aliquoted into micronics tubes (approximately 55 mg per tube) and incubated for at least 24 hours in the above media. Media was harvested and new media was added (alone or with fresh insulin) at various time points (0, 24, 48 and 72 hours).

Proteoglycan Release:

Media was harvested at various time points was assayed for proteoglycan content using the 1,9-dimethylmethylene blue (DMMB) colorimetric assay of Farndale and Buttle, *Biochim. Biophys. Acta* 883: 173-177 (1985) as described above. PG release at 0 hours was used as a baseline measurement, and any samples with especially high or low PG release were discarded prior to treatment with insulin. For all treatments, results represent the average of 5 independent samples.

Proteoglycan Synthesis:

At 48 hours after the first treatment, $^{35}$S-sulfate was added to cartilage explants at a final concentration of 10 µCi/ml along with fresh media (with or without test compound). After an additional 12-17 hours of incubation at 37° C., the media was removed and saved for subsequent PG and nitric oxide (NO) analysis. The cartilage explants were washed twice with explant media and digested overnight at 50° C. in a 900 mL reaction volume of 10 mM EDTA, 0.1M sodium phosphate and 1 mg/ml proteinase K (Gibco BRL). The digestion reaction was mixed (2:1) with 10% w/v cetylpyridinium chloride (Sigma) to precipitate the proteoglycans and centrifuged at 1000×g for 15 minutes. The supernatant was removed and formic acid (500 ml, Sigma) was added to dissolve the pellets. The samples were then transferred to vials containing 10 ml scintillation fluid (ICN) and read in a scintillation counter.

Remaining Proteoglycan in Cartilage Tissues:

After 72 hours, the remaining articular cartilage explants were digested as described above under Proteoglycan synthesis and assayed for proteoglycan content using the DMMB calorimetric assay (referenced above under Proteoglycan release).

Nitric Oxide Assay:

Articular cartilage media saved from the cartilage explants at various times (24, 48, and 72 hours) was mixed with 10 µl 0.05 mg/ml 2,3-diaminonapthalene (DAN) in 0.62M HCl and incubated at room temperature for 10-20 minutes in the dark. The reaction was terminated with 5 µl of 2.8N NaOH. The amount of fluorescence of 2,3-diaminonaphthotriazole was measured with a Cytoflor fluorescent plate reader at 365 nm excitation at 409 nm emission.

Results and Discussion

Figure 3A:
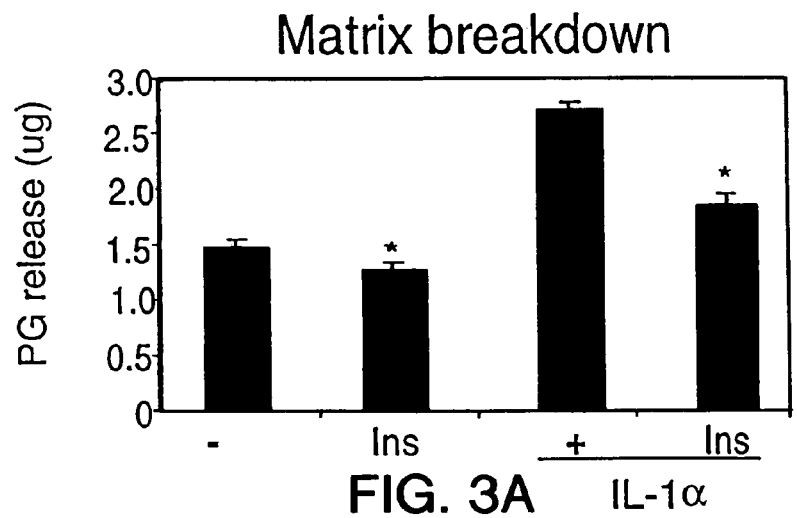
FIG. 3 shows the anabolic effects of insulin on articular cartilage explants. Insulin treatment of porcine articular cartilage explants every day for 3 days resulted in a decrease in basal and IL-1α-induced matrix breakdown, as determined by measuring the amount of proteoglycans in the media using the DMMB assay (top panel, FIG. 3A). The treatment also significantly increased matrix synthesis and partially overcame the inhibition of matrix synthesis induced by IL-1α (bottom panel, FIG. 3B).
Figure 3B:
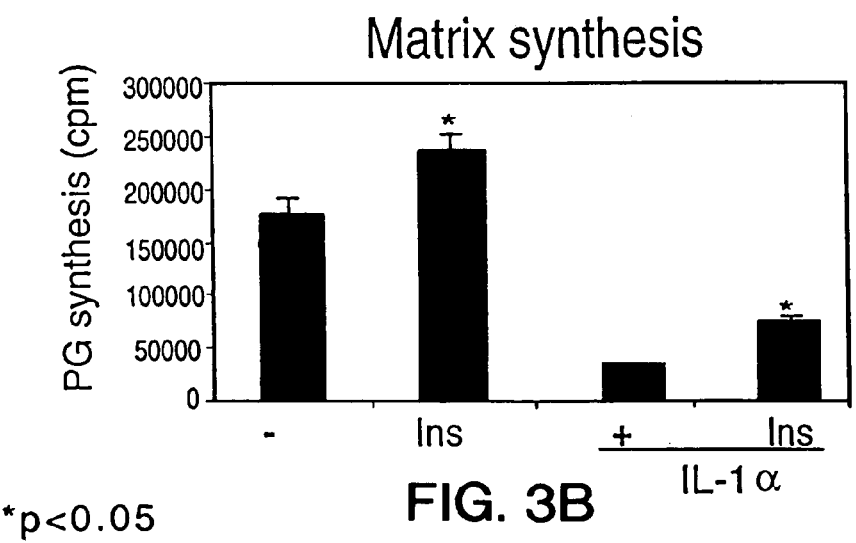
Figure 4:
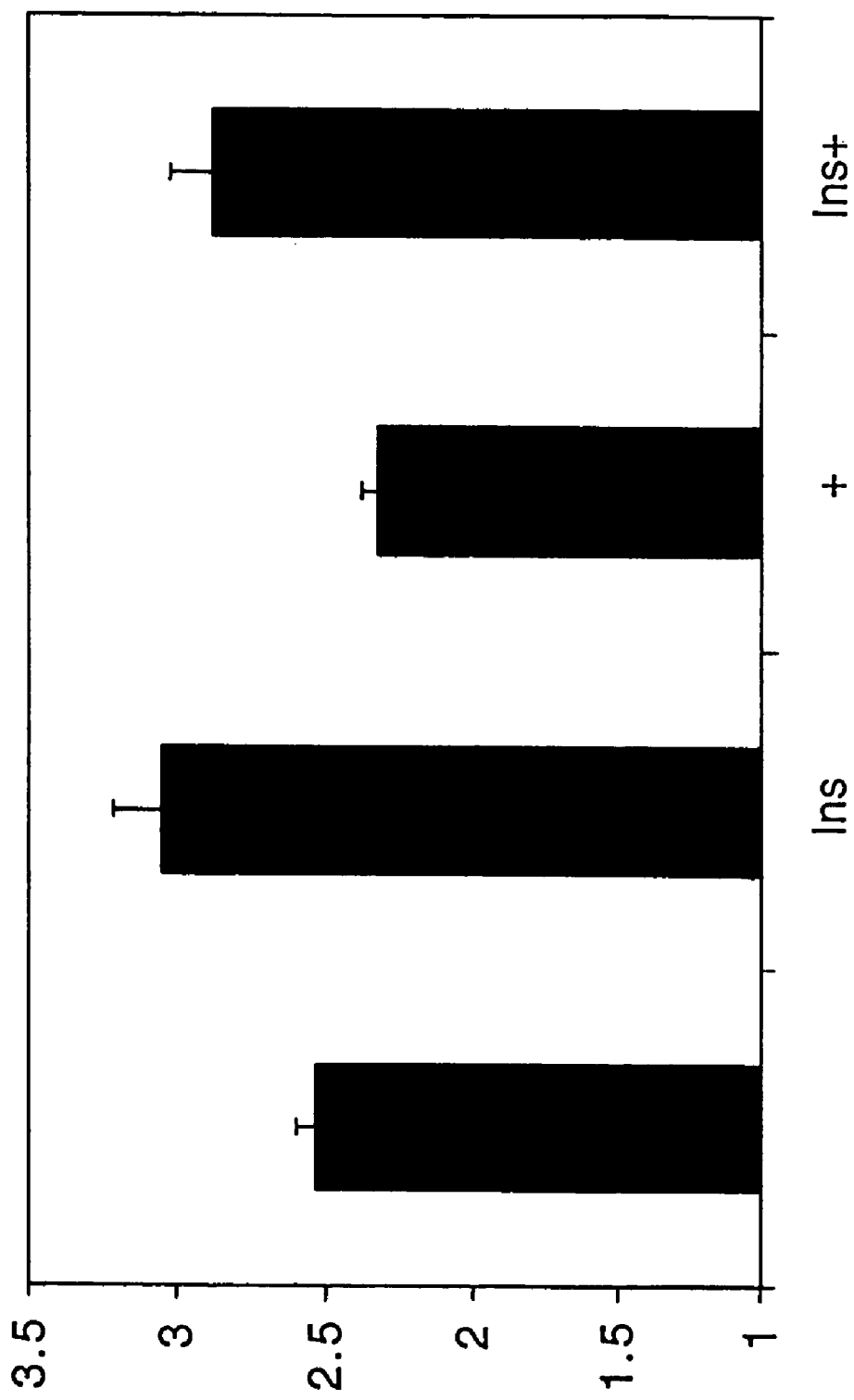
FIG. 4 shows the effects of insulin on retention of cartilage matrix proteins. The inhibition of matrix breakdown and induction of matrix synthesis by insulin (as shown above in FIG. 3) resulted in an increase in the amount of matrix remaining in the cartilage tissue at the end of the 3 day treatment. Insulin was also able to overcome the decrease in cartilage matrix content induced by IL-1α (+vs. Ins+).

Similar to its effects on primary articular chondrocytes (FIG. 1), insulin (Intergen, Purchase, New York, cat. no. #450100) induced proteoglycan synthesis in articular cartilage explants and could at least partially block the inhibitory effects of IL-1α (R&D Systems, cat. no. 200LA002)(FIG. 3B). In addition, insulin decreased the breakdown of matrix which occurs in absence or presence of IL-1α (FIG. 3A). Since matrix breakdown is one of the earliest and most destructive features of arthritis, inhibition of this process and stimulation of new matrix molecules should promote tissue and joint repair. Most importantly, this decrease in matrix breakdown and increase in synthesis induced by insulin resulted in an increase in the total amount of proteoglycans in the articular cartilage explants relative to that of untreated tissues (FIG. 4). By increasing the amount of matrix retained in cartilage, insulin treatment in vivo would lead to retention of articular cartilage matrix, and thus inhibition of subsequent joint destruction and deformity.

Figure 5A:
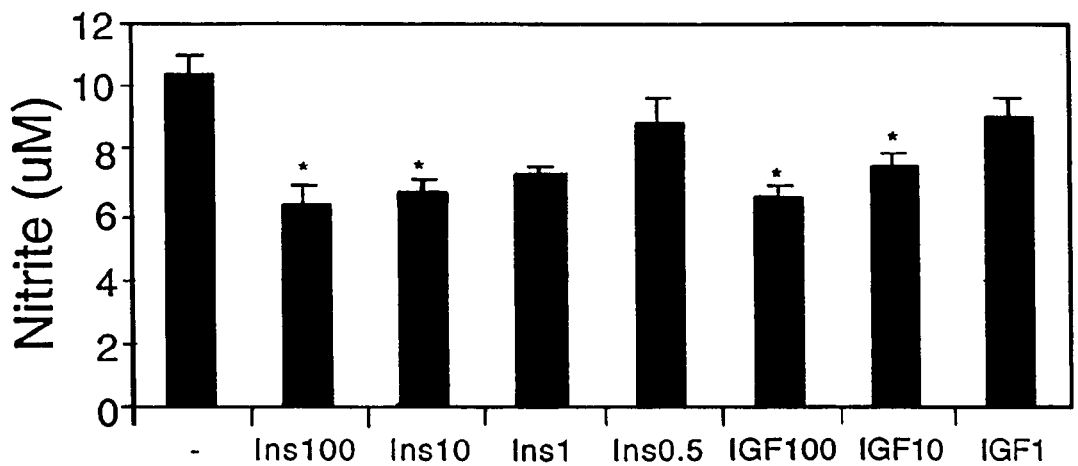
FIG. 5 shows that insulin and IGF-1 decreased nitric oxide release by AC explants. Media was harvested from articular cartilage explants which were treated with insulin (0.5-100 nM), IGF-1 (1-100 ng/ml) or media alone (−) in the absence (top panel, 5A (−)) or presence (bottom panel, 5B (+)) of IL-1α. The amount of nitrite in the media was measured using 2,3-diaminonapthalene (DAN) which reacts with nitrite under acidic conditions to form 1-(H)-naphthotriazole, a fluorescent product.
Figure 5B:
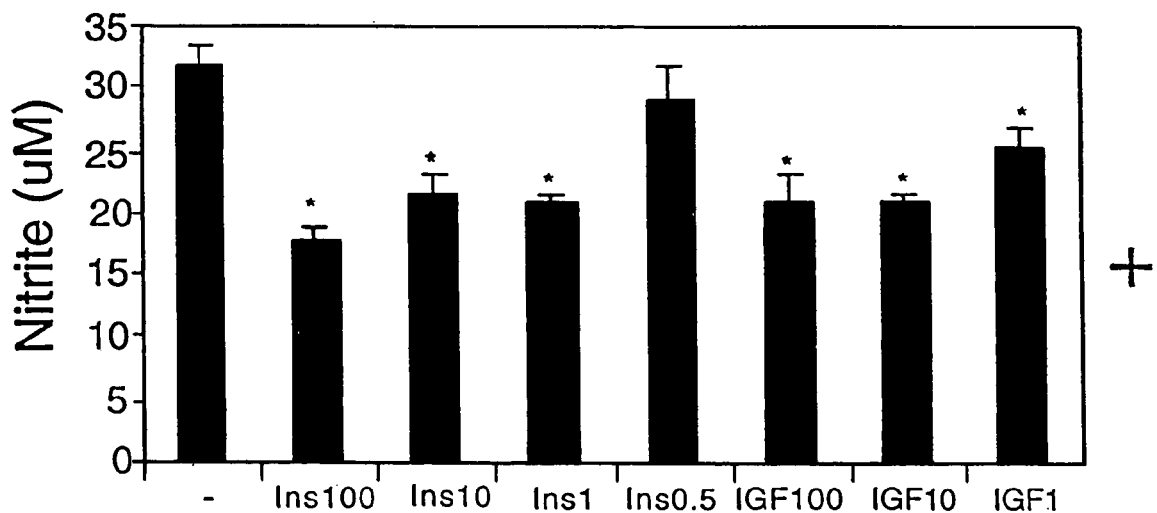

In addition to its ability to decrease matrix breakdown and increase matrix synthesis, insulin also inhibited nitric oxide (NO) production by either untreated or IL-1α-treated articular cartilage explants (FIG. 5). This effect was seen at concentrations as low as 1 nM and was also seen with IGF-treated explants. As described above, nitric oxide has detrimental effects on chondrocytes as well as other cell types within the joint. Since inhibition of nitric oxide has been shown to inhibit progression of arthritis in animals, the effect of insulin on NO further suggests that insulin would be protective for joint tissues in vivo.

Example 3

Mouse Patellae Assay

Introduction

This assay determines the in vitro and in vivo effect of the tested compound on proteoglycan synthesis in the patellae of mice. The patella is a very useful model to study the effects of the test compound because it permits the evaluation on cartilage which has not been removed from the underlying bone. Moreover, since each animal has one patellae in each leg, experiments can be performed using the contralateral joint as a control. This assay involves injection of a protein into the intra-articular space of a (mouse) knee joint, and subsequent harvest (within a few days after injection) of the patella (kneecap) for measurement of matrix synthesis (FIG. 6). The procedure performed herein, and outlined in FIG. 6, has been previously used to measure effects of cytokines in vitro and in vivo (Van den Berg et al., *Rheum. Int.* 1: 165-9 (1982); Vershure P. J. et al., *Ann. Rheum. Dis.* 53: 455-460 (1994); and Van de Loo et al., *Arthit. Rheum.* 38: 164-172 (1995)).

Materials and Methods

In Vitro Treatment of Patellae

Patellae of 2 month old C57B1-6J mice (Jackson Laboratories) were dissected away from surrounding soft tissue and incubated overnight in explant media (see above, example 2) with no additional factors or with 100 ng/ml IL1α or 100 nM insulin. Patellae were labelled with $^{35}$S-sulfur (30 µCi/ml) during the last 3 hours of the 18 hour incubation, and then washed three times with phosphate buffered saline (PBS). Samples were fixed overnight in 10% formalin followed by decalcification of the underlying bone in 5% formic acid. Cartilage was dissected away from the underlying bone, placed in 500 µl of a tissue and gel solubilizer (Solvable, Packard Instrument Company) and incubated at 60° C. for 1.5 hours. Scintillation fluid designed for concentrated alkaline and salt solutions (HIONIC-fluor, Packard Instrument Company) was added (10 mL) to each tube and mixed thoroughly. $^{35}$S uptake was then measured using a scintillation counter. The levels of PG synthesis are reported as cpm and show the average of patellae from 4 different mice/group.

In Vivo Treatment of Patellae

Figure 7A:
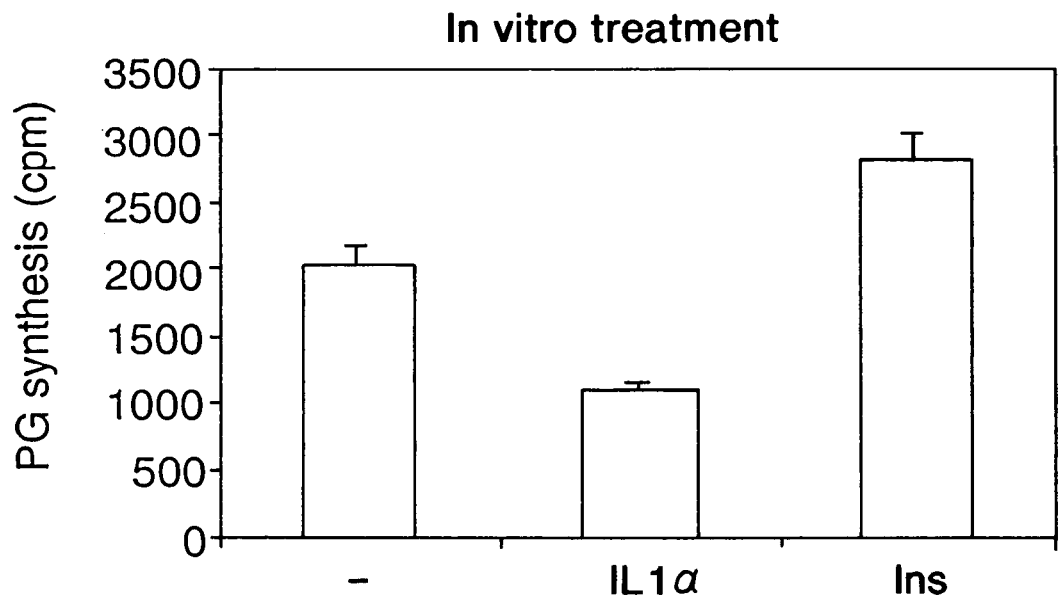
FIG. 7 shows the effect of insulin on mouse patellae. Patellae were harvested from mice and incubated with either IL-1α or insulin (Ins) for 24 hours. During the last three hours, patellae were labelled with $^{35}$S-sulfate. Patellae were then processed as described in FIG. 6. In this model, IL-1α decreased and insulin increased matrix synthesis in this intact articular cartilage assay (upper panel, FIG. 7A—in vitro treatment). For in vivo analyses, mice were injected in one knee with insulin, and in the other knee with buffer alone (PBS+0.1% BSA) every day for three days, and patellae were harvested and analyzed in the patella assay. Shown (bottom panel, FIG. 7B) are two separate experiments. In the first experiment (left side), mice were injected with 6 μl of a 10 mg/ml insulin stock solution daily, and patellae were harvested 3 hours after the third injection. In the second one (right side), mice were injected with 31 μl of 10 mg/ml stock solution daily, and patellae were harvested 24 hours after the third injection. Results are expressed as the amount of radioactive incorporation relative to control (contralateral knee) so that anything over 1.0 indicates an induction of synthesis in the insulin-injected knee.
Figure 7B:
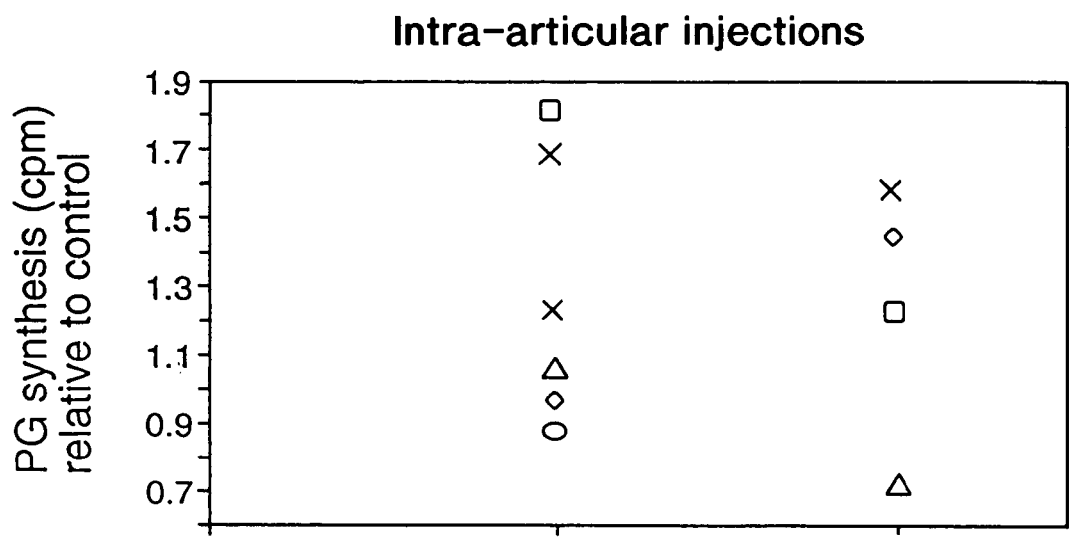

Mice were separated into two subgroups and injected and either a high dose (6 µl) or a low dose (3 µl) of the test compound (e.g., insulin @10 mg/ml) was injected intra-articularly into the right knee daily for three consecutive days. The patellae were then harvested, labelled for 3 hours in explant media without any additional factors, and processed as described above. FIG. 7B displays the data as a ratio of the incorporation into the treated versus untreated knee. Datapoints representing a treated/untreated ratio of greater than 1 (above the line) indicate that treatment of the tested compound resulted in increased proteoglycan synthesis. PG synthesis as a result of application of the high dose (6 µl) is indicated by the left datapoints, while the low dose (3 µl) is indicated by the right datapoints. Each point represents results from an individual mouse.

Results and Discussion

Similar to its induction of proteoglycan (PG) synthesis in vitro in the dissected cartilage explants (example 2), insulin stimulated PG synthesis in intact cartilage both in vitro (FIG. 7A) and in vivo (FIG. 7B). More specifically, injection of insulin (Intergen, Purchase, New York, cat. no. 450100) into normal mouse knee joints resulted in an approximately 25% increase in PG synthesis in 3 days (FIG. 7B). Such an increase would likely have a beneficial effect on diseased tissues where cartilage matrix, lost through degradation, can not be replaced. Furthermore, this percentage increase may under-estimate the beneficial effects of insulin on cartilage matrix in vivo, since the ability of insulin to decrease cartilage breakdown (see example 2) would not have been detected by this assay and thus not be included in this calculation. The decrease in breakdown induced by insulin would further increase the amount of matrix retained in insulin-treated knee joints. Finally, these experiments represent initial attempts to determine safety in an animal model. Rather surprisingly, no adverse effects were seen upon intra-articular injection of very high doses (30 µg) of insulin once/day for 3 days.

Thus, the test compound insulin had positive effects on cartilage within in the joint space, and intra-articular injection of purified insulin protein into knee joints appears to be a tenable treatment strategy.

Example 4

Guinea Pig Model

Introduction

These experiments measure the effect of the test compound on proteoglycan (PG) synthesis and breakdown in the cartilage of Dunkin Hartley (DH) Guinea Pigs, an accepted animal model for osteoarthritis (Young et al., "Osteoarthrits", *Spontaneous animal models of human disease* vol. 2, pp. 257-261, Acad. Press, New York. (1979); Bendele et al., *Arthritis Rheum*. 34: 1180-1184; Bendele et al., *Arthritis Rheum*. 31: 561-565 (1988); Jimenez et al., *Laboratory Animal Sciences* vol 47(6): 598-601 (1997). Unlike most other animal models which have rapidly progressing tissue breakdown in their joints, DH guinea pigs have naturally occurring, slowly progressive, non-inflammatory OA-like changes in their joints.

The highly reproducible pattern of cartilage breakdown in these guinea pigs is similar to that seen in the human disorder (FIG. 8). While joints appear normal in 2 month old DH guinea pigs, as the animals age, the course and severity of the disease progresses in a manner similar to that of human OA. Thus, early histologic change include focal chondrocyte degeneration and death and loss of matrix in the superficial layer of articular cartilage. While surviving chondrocytes adjacent to the hypocellular fibrillated area may synthesize proteoglycans, these cells can not maintain normal matrix content and structure. These chondrocytes do not migrate into and distribute themselves normally within the hypocellular area—instead, they stay in clusters surrounded by proteoglycan. As a result, this cartilage matrix devoid of normally distributed chondrocytes undergoes further degeneration, ultimately resulting in destruction of the articular surface (Bendele and Hulman, *Arthritis Rheum*. 31: 561-565 (1988)). Thus, over time, chondrocyte and matrix loss become more extensive. A transient increase in chondrocyte proliferation leads to the formation of peripheral chondrophytes, which subsequently undergo endochondral ossification to form osteophytes. Thereafter, moderate to severe cartilage degeneration occurs, with extensive deep cartilage degeneration, osteophyte formation, subchondral bone thickening and synovial hyperplasia and fibrosis. Thus, the joints of DH guinea pigs over 1 year old are severely affected with marginal osteophytes of the tibia and femur, sclerosis of the subchondral bone of the tibial plateau, femoral condyle cysts, and calcification of the collateral ligaments. (Jimenez et al., supra).

Materials and Methods

Male Dunkin Hartley guinea pigs, obtained from Charles River Laboratories (Wilmington, Mass.) were separated into treatment groups for sacrifice at 1-2, 6 and 11 months of age. At sacrifice, the metacarpophalangeal joints were aseptically dissected, and articular cartilage was removed by free-hand slicing taking care so as to avoid the underlying bone. Cartilage was minced, washed and cultured in bulk for at least 24 hours in a humidified atmosphere of 37° C. and 5% $CO_2$ in serum free (SF) LG DMEMIF12 media with 0.1% BSA, 100 U/ml penicillin/streptomycin (Gibco), 2 mM L-Glutamine, 0.1 mM sodium pyruvate (Gibco), 20 µg/ml Genamicin (Gibco) and 1.25 mg/L Amphotericin B. Articular cartilage was aliquoted into Micronics tubes (approximately 35 mg per tube) and incubated for at least 24 hours in the above media. Media was harvested and fresh media was added alone or with insulin at various time points (0, 24, 48 and 72 hours).

Proteoglycan Release:

Media harvested at various time points was assayed for proteoglycan content using the 1,9-dimethylmethylene blue (DMMB) colorimetric assay of Farndale and Buttle, *Biochem. Bhiophys. Acta* 883: 173-177 (1985) as described above (example 2, articular cartilage explant assay). PG release at 0 hours was used as a baseline measurement, and any samples with especially high or low PG release were discarded prior to treatment.

Proteoglycan Synthesis:

After the media change at 48 hours, $^{35}$S-sulfate (final concentration of 10 µCi/ml) was added to the cartilage explant cultures, and tissues were processed as above under Example 2, Articular Cartilage Explant Assay).

Remaining Proteoglycan in Cartilage Tissues:

After 72 hours, the remaining articular cartilage explants were digested as described above under Proteoglycan synthesis and assayed for proteoglycan content using the DMMB colorimetric assay (referenced above under Proteoglycan release).

Results and Discussion

Figure 9A:
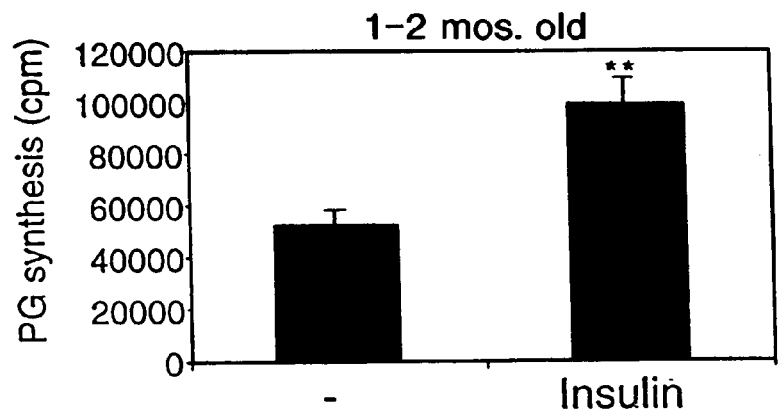
FIG. 9 shows that insulin has an anabolic effect on normal and diseased cartilage. Articular cartilage was harvested from male Hartley guinea pigs and cultured as explants in serum-free media without (−) or with insulin (Insulin) at 100 nM. Incorporation of $^{35}$S-sulfate was used an indication of proteoglycan synthesis. Note that at all ages (e.g., 1-2 months—FIG. 9A, 6 months—FIG. 9B, and 11 months—FIG. 9C) insulin significantly stimulated proteoglycan synthesis.
Figure 9B:
Figure 9C:
Figure 10:
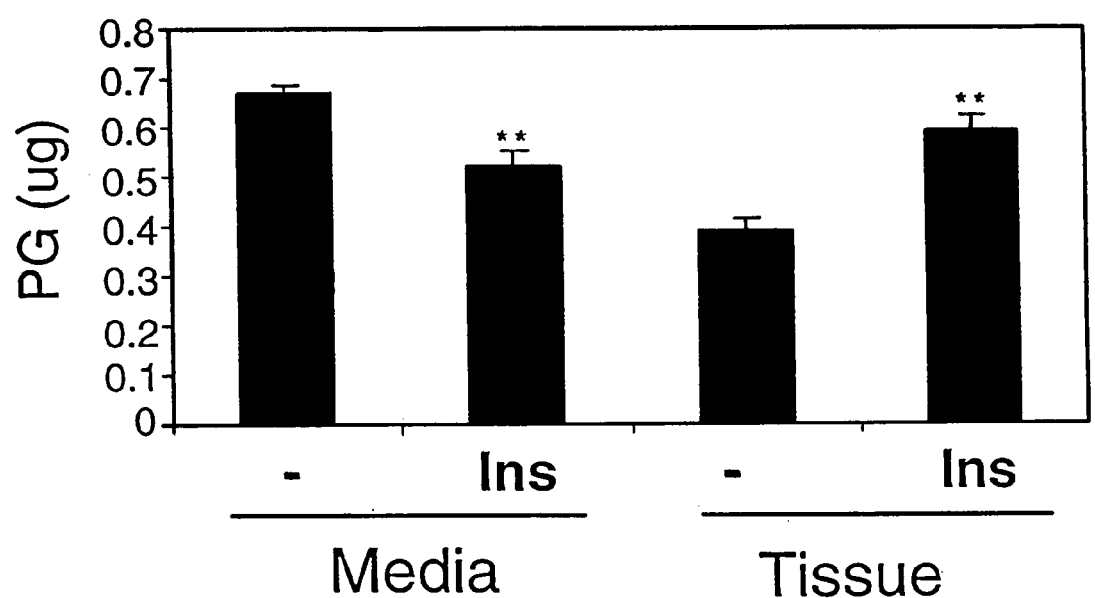
FIG. 10 shows that insulin decreased catabolism of guinea pig articular cartilage. Insulin (Ins) decreased the amount of matrix breakdown as determined by measuring the amount of proteoglycans released from articular cartilage explants from 11 month old male Hartley guinea pigs (left side "media"). After three days of treatment, cartilage explants were digested overnight, and the amount of proteoglycans remaining in the tissue was determined using the DMMB assay (right side "tissue"). The decrease in matrix breakdown (media), and the increase in matrix synthesis (FIG. 9) resulted in an increase in the amount of matrix remaining in the tissue at the end of the 3 day treatment (tissue).

One factor which is known to affect cartilage matrix metabolism is age. Not only does the rate of biosynthesis and the ability to repair tissue decrease with age, but responsiveness to a number of growth factors, including insulin-like growth factor (IGF-1), is compromised as well (Schafer et al. *Arch. Biochem and Biophys.* 302:431-438 (1993). Disease is also associated with a decrease in growth factor sensitivity, as evidenced by the finding that the response of arthritic cartilage to IGF-1 is significantly blunted relative to age-matched controls (Chevalier and Tyler 1996, *Br. J. Rheum* 35: 515-522; J. Posever et al., *J. Orthopaedic Res.* 13: 832-827 (1995)). For this reason, we tested the effect of insulin on tissue from guinea pigs at various ages, and thus various stages of degeneration. As shown in FIG. 9, insulin increased proteoglycan (PG) synthesis to approximately the same extent (two-fold) in articular cartilage from 1-2, 6, or 11 month old DH guinea pigs. Thus, DH guinea pig cartilage responded to insulin at various ages and stages of disease. Besides increasing PG synthesis, insulin also decreased matrix breakdown, as shown by a decrease in the amount of PGs in the media of insulin-treated explants (FIG. 10, left side, "Media"). Most importantly, this insulin-induced decrease in breakdown and increase in synthesis resulted in a significant net gain in the amount of proteoglycans remaining in insulin-treated cartilage, even in tissue from 11 month old animals treated for only 3 days (FIG. 10, right side "Tissue"). This data, which shows an increase in the amount of PGs maintained in the matrix of insulin treated cartilage, strongly suggests that insulin would be a very effective and potent stimulator of cartilage repair, since loss of matrix occurs early and continuously through-out the disease process.

Example 5

Diabetic Mouse Model

Metabolic changes in patients with diabetes mellitus (DM) affect many organ systems. For example, patients with diabetes have an increased number of musculoskeletal injuries and disorders relative to patients without diabetes. In fact, diabetes is one of the known risk factors for developing arthritis. Changes in proteoglycans have been found in the intervertebral disc of diabetic patients, and articular cartilage samples from patients with diabetes mellitus have compromised structural integrity (Robinson et al. *Spine* 23:849-55 (1998); Athanasiou et al., *Clin Orthop* 368, 182-9 (1999). The mechanism underlying these changes in articular cartilage in diabetic patients is not yet known.

Syndromes resembling human diabetes occur naturally in many animals or can be induced surgically by removal of pancreata or by treatment with drugs, viruses, or a specific diet. Among these models, diabetes induced by streptozotocin (STZ) administration is accompanied by defects in insulin secretion and action which in many ways resemble those found in human non-insulin dependent diabetes (Portha, B. et al. *Diabetes Metab.* 15:61-75, 1989). Streptozotocin (STZ)-induced diabetes in animal models is associated with atrophy and depressed collagen content of connective tissues including skin, bone, and cartilage (Craig, R. G. et al. *Biochim. Biophys. Acta* 1402: 250-260.1998). Importantly, cartilage from STZ-induced rats was found to be resistant to the anabolic action of IGF-I, as measured by $^{35}SO_4$ incorporation in vitro (Kelley, K. M. et al. 1993. *Diabetes* 42: 463-469). In order to better understand the effects of diabetes on cartilage matrix metabolism and to test the effects of insulin in another model of diseased, potentially growth-factor resistant cartilage, we measured matrix synthesis in articular cartilage from STZ-induced diabetic mice cultured alone or in the presence of insulin.

Materials and Methods

Induction of Diabetes:

8 week old female CD-1 mice were injected with 40 mg/kg STZ for 5 consecutive days. Patellae were harvested at 2, 3, or 5 months after treatment. Blood was also collected from the tail at these same timepoints, and blood glucose levels were measured using a glucose meter (One-Touch, Lifescan).

Patella Assay:

Patellae were incubated in the absence of presence of insulin (100 nM, Intergen, Purchase, New York, cat. no. 450100) and $^{35}S$-sulfate (final concentration 15 µCi/ml) for 18 hours. Patellae were dissected as processed as above (example 3).

Results and Discussion

Figure 11:
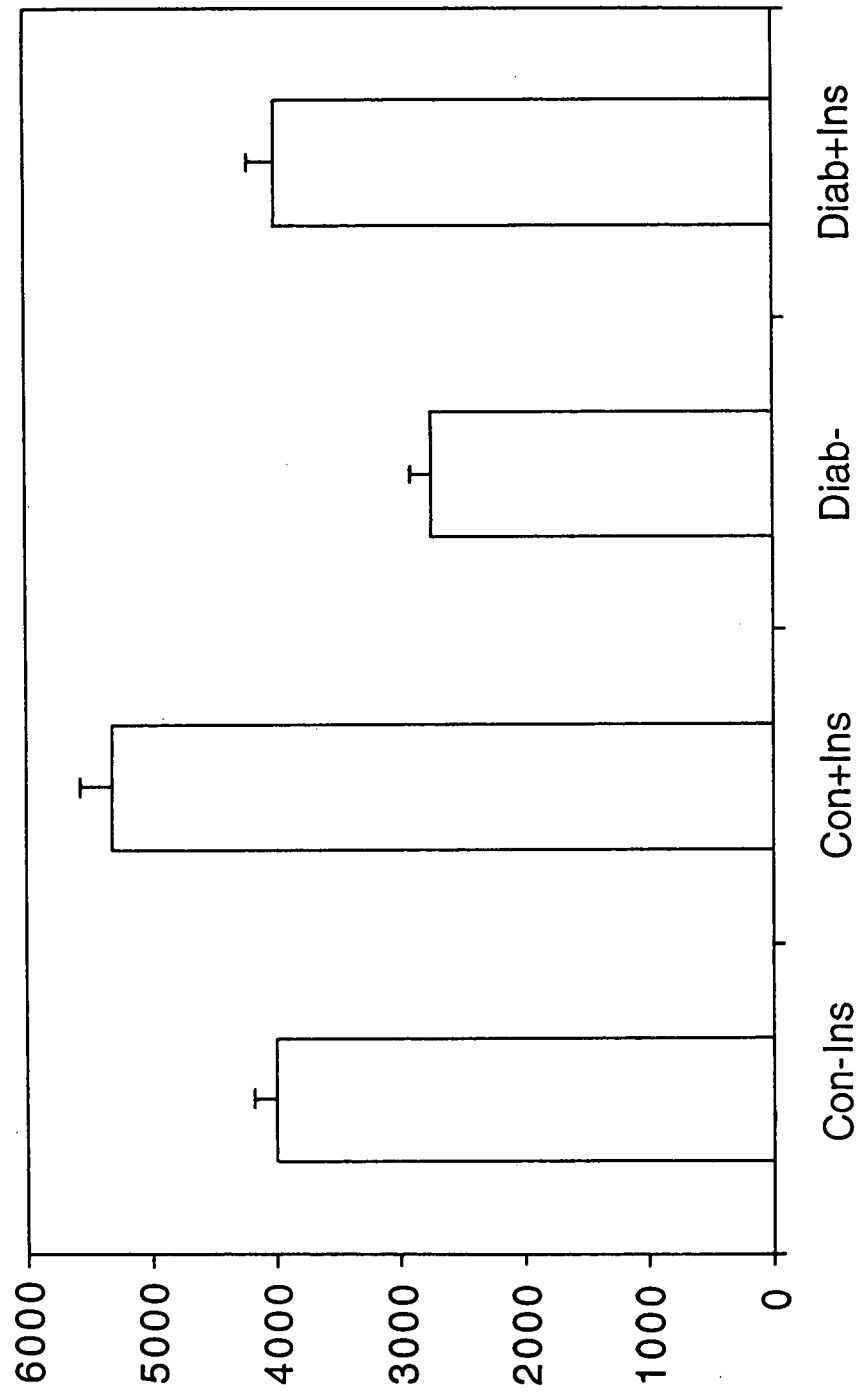

At all timepoints tested (2, 3 and 5 months), articular cartilage from STZ-treated mice had lower basal levels of proteoglycan synthesis (FIG. 11). This decrease in synthesis could be due to the fact that STZ-treatment results in low serum insulin levels due to destruction of pancreatic cells which produce insulin (Portha, B et al. *Diabetes Metab.* 15:61-75, 1989; Craig, R. G. et al. *Biochim. Biophys. Acta* 1402: 250-260.1998; Kelley, K. M. et al. *Diabetes* 42: 463-469 (1993). Most importantly, insulin induced matrix synthesis in cartilage from STZ-treated mice to the same extent as in cartilage from normal mice. In fact, insulin was able to restore matrix synthesis in cartilage of STZ-treated mice to levels comparable to that of untreated, normal mice. In contrast, IGF-1 was not able to increase proteoglycan synthesis in cartilage from STZ-treated animals (Kelley, K. M. et al. *Diabetes* 42: 463-469 (1993). Therefore, diseased tissue is not equally responsive to anabolic factors, and insulin may prove to be more effective than IGF-1 in diabetic animals.

Our data supports the hypothesis that insulin-deficiency in STZ-treated mice leads to decreased matrix synthesis in cartilage. Furthermore, regardless of the mechanism whereby synthesis is lower in STZ-treated mice, insulin treatment was able to restore synthesis to normal levels. These results suggest that insulin would be an effective treatment for disorders (other than primary arthritis) in which cartilage tissue has defects in matrix synthesis and/or breakdown.

Example 6

Preparation and Analysis of Polymeric Microspheres Containing Recombinant Human Insulin Introduction While intra-articular injections are generally well-tolerated by patients and once/week injections of therapeutics are currently being tested clinically, an ideal drug would be one in which a limited number of doses was required. Unfortunately, human insulin (HI) is unstable when stored in neutral solutions at low concentration for extended periods of time. J. Brenge and L. Langkjoer, *Insulin Formulation and Delivery in Protein Delivery* Eds. L. M. Sanders and W. Hendren. Furthermore, insulin has a half-life of about 5 minutes in the human body. Hadley, M. E. *Endocrinology*, Prentice-Hall, Inc. 1988. Thus, a stabilized, slow-release formulation of HI is highly desirable. Human insulin (Eli Lilly, Indianapolis, Ind.) has also been formulated with zinc acetate to produce a sparingly soluble Zn:H1 complex. The Zn:H1 complex is believed to result in a longer-acting formulation of insulin. In fact, histochemical evidence indicates that HI is stored in the pancreas as a zinc complex. J. Brenge and L. Langkjoer, *Insulin Formulation and Delivery in Protein Delivery* Eds. L. M. Sanders and W. Hendren, Plenum Press, 1997; Hadley, M. E. *Endocrinology*, Prentice-Hall, Inc. 1988. In addition, HI complexed with zinc is known to be more resistant to aggregation than uncomplexed HI. J. Brenge and L. Langkjoer, supra. Finally, insulin complexed with zinc has been shown to have a slower onset and a longer duration of activity (up to 24 hours) in humans relative to regular insulin. J. Brenge and L. Langkjoer, supra.

The microsphere formulations were analyzed to determine size, protein load, physical and biological integrity. The amount of human insulin (HI) encapsulated (w/w) was determined by chemical analysis as per Cleland, J. C. and Jones, A. J. S., *Pharm. Res.* 13(10): 1464-1475 (1996)]. The physical and biological integrity of the HI recovered from the microspheres was analyzed by size exclusion (SEC) and reverse-phase chromatography (RPC). SEC and RPC were used to detect aggregated and deamidated HI, respectively.

Material and Methods

Microsphere Formulation:

In the microsphere formulations prepared, both the Zn:HI hexamer ratio (e.g., formulation I-2:1 and formulation II-4:1) while the protein loading remained constant (approximately 5.0%). The molar ratio of lactide to glycolide in all polymers was kept constant at 50:50. All microsphere formulations were prepared using D,L-PLGA obtained from Boehringer Ingelheim (Ingelheim, Germany; RG502H; 0.2 dL/g, 8 kD). Recombinant human insulin (HI) was encapsulated into PLGA microspheres using a cryogenic, non-aqueous process described by Gombotz et al., U.S. Pat. No. 5,019,400, issued May 28, 1991 and Johnson et. al. *Nature Med* 2 (7):795-799 (1996).

In preparation for insertion into the microspheres, the above HI formulations were first spray-freeze dried. This process was accomplished by atomizing the above formulations through an ultrasonic nozzle (Sono-Tek, Milton N.Y.) into liquid nitrogen, followed by lyophilization as previously described (Johnson et al. supra). For example, the dried Zn—HI powder (100 mg) was added to 5.8 ml of a 0.17 mg/ml solution of the D,L-PLGA described above in ethylacetate solvent and homogenized for 2 minutes at 8000 rpm with a shear homogenizer (Vitrius Inc. Giandiner, N.Y.) in order to form a uniform suspension of Zn—HI and polymer. The polymer and Zn—HI suspension was sprayed through a sonicating nozzle (Sono-Tek, Milton N.Y.) into a vessel containing 300 ml of frozen ethanol. The vessel was then placed in a −70° C. freezer (to raise the temperature to −70° C.) whereupon the frozen ethanol melted and the micropheres slowly hardened as the ethylacetate solvent was extracted by the ethanol. After 3 days, the hardened microspheres were harvested by filtration through a 20 µm screen then dried under nitrogen gas for 4 days and finally sieved through a 60 µm screen.

Chromatography:

Size exclusion (SEC) and reverse-phase chromatography (RPC) procedures were performed as per published methods (Pietta, P. G. et al., *J. Chromatogr.* 549:367:373 (1991); Klyushnichenko V. E. et al., *J. Chromatogr.* 661:83-92 (1994). Briefly, the SEC was performed on a Zorbax® Column with phosphate buffer as the mobile phase. HI was detected by UV absorption at 214 nm. Reverse-phased chromatography was carried out on a C-18 reversed-phase column using sulfate buffer with acetonitrile as the mobile phase at 40° C., HI was detected by UV absorption at 214 nm as previously described (Pietta, P. G. et al., *J. Chromatogr.* 549:367-373 (1991); Klyushnichenko, V. E. et al., *J. Chromatogr.* 661:83-92 (1994).

Protein Analysis:

Encapsulated HI was recovered form the microspheres by dissolving them in 1.0 N sodium hydroxide (NaOH) and the soluble protein was recovered and analyzed by UV absorbances using the experimentally determined absorbance A (1 mg/mL, 291 nm, 1 cm)=1.94.

Results and Discussion

The mean particle diameter distribution of the microspheres was measured on a Malvern Masterisizer X and were found to be about 30 microns (Table I). Protein loading of formulation I and formulation II was found to be 5.56% and 5.59% respectively (Table I). The analysis of HI integrity indicated that there were no significant differences between the protein before and after encapsulation as determined by an insulin receptor kinase assay KIRA (see Example 7 below for procedure).

TABLE I

Physical properties of PLGA insulin microsphere formulations

| Formulation | Loading (% w/w) | Diameter (nm) | Insulin Zn Ratio[a] |
|---|---|---|---|
| Formulation I | 5.56 | 30.2 ± 12 | 1:2 |
| Formulation II | 5.59 | 36.6 ± 11 | 1:4 |

[a]Ratio defined as moles insulin hexamer/moles of zinc

Example 7

Release of Insulin From HI Microspheres

Introduction

In order to determine the amount of insulin released, insulin-loaded microspheres were incubated under 3 different conditions, and the recovered protein was analyzed for activity at several timepoints. Initially, microspheres were incubated in 10 mM histidine buffer at pH 7.4 at 37° C. In order to measure release under conditions similar to that of the joint, microspheres were also incubated in either synovial fluid or with articular cartilage explants. In all cases, samples were taken at several timepoints and analyzed by measuring induction of insulin receptor phosphorylation in cells expressing the human insulin receptor.

Materials and Methods

Release of Insulin in Buffer:

To evaluate the in vitro release profile for HI microsphere formulations, 20 mg of each HI microsphere formulation was placed in 500 μL of release buffer (10 mM Histidine, 10 mM NaCl, 0.02% Polysorbate 20, 0.02% NaN3, pH 7.2) and incubated at 37° C. The entire release medium was replaced at each sampling interval and the resulting release samples stored at 5° C. prior to analysis.

Release of Insulin in Synovial Fluid:

Synovial fluid was harvested from 7-8 week old male Sprague-Dawley rats and diluted 1:2 with phosphate buffered saline (PBS). The entire release medium was replaced at each sampling interval and the resulting samples stored at 5° C. prior to analysis.

Release of Insulin in Explant Cultures:

Media from articular cartilage explants, incubated with insulin (10 nM) or PLGA-Insulin microspheres was harvested at various timepoints and tested for activity in the insulin kinase receptor assay. PLGA-Ins beads were resuspended in 500 ul of explant media, and 3 ul of this mixture was added to each explant sample in 260 ul of explant media.

Insulin Kinase Receptor Assay (KIRA):

Cell stimulation: Chinese Hamster Ovary (CHO) cells transfected with the human insulin receptor were plated (100 μl of $5\times10^5$ cells/mL) in flat bottom-96-well sterile tissue culture plates (Falcon 1270) in media (PS/20 with 5% diafiltered FBS and antibiotics 1×glutamine, 1× penn/strep, 10 μg/mL puromycin) and incubated overnight in humidified atmosphere of 37° C., 95% air and 5% $CO_2$. Cells were then treated with 100 μl of sample in media (PS/20 with 0.5% BSA) and incubated for 15 minutes at 37° C. 130 μl of Lysis Buffer (150 mM NaCl with 50 mM HEPES and 0.5% Triton-X 100) with protease (AEBSF, 1 mM, Aprotinin, Leupeptin 0.05 mM) and phosphatase (Sodium orthovanidate, 20 mM) inhibitors was added to each well. Samples were then used for ELISA analysis.

Enzyme-linked immuno-specific assay (ELISA): Plates (Nunc Maxisorp immunoplate 4-39454) were coated with 100 μl of 1° monoclonal antibody (final concentration 2 μg/ml in PBS pH 7.0) at 4° C. overnight. After removal of this solution, plates were incubated with 150 μl of blocking buffer (PBS with 0.5% BSA) for 1 hour. Plates were then washed three times with wash buffer (PBS with 0.05% tween 20 pH 7.4) (Skatron Scan Washer 300). 80 μL of lysis buffer (150 mM NaCl with 50 mM HEPES and 0.5% Triton-X 100) and 20 μl sample (from above) were added to the prepared ELISA plates. Plates were incubated at room temperature for 2 hrs with gentle agitation. After washing wells six times with wash buffer, samples were incubed with 100 μl of biotinylated 2° antibody (4G10, final concentration 0.1 μg/ml in assay buffer, PBS with 0.5% BSA, 0.05% tween 20 and 5 mM EDTA, pH 7.4) (UBI) for 2 hours with gentle agitation. Plates were then washed six times in wash buffer, and samples were incubed with 100 μl of Streptavidin/HRP (diluted 1:50,000 in assay buffer) (Amdex) at room temp. for 1 hour with gentle agitation. Plates were then washed with wash buffer six times and incubated with 100 μl of substrate solution (1 volume of K&P TMB substrate+1 volume of K&P TMB peroxide solution in TMB, substrate kit from Kirkegard and Perry). After color development (10-15 minutes), the reaction was quenched with 100 μl of 1.0 N H3PO4. The O.D. at 450 nm was then read.

Results and Discussion

Figure 12:
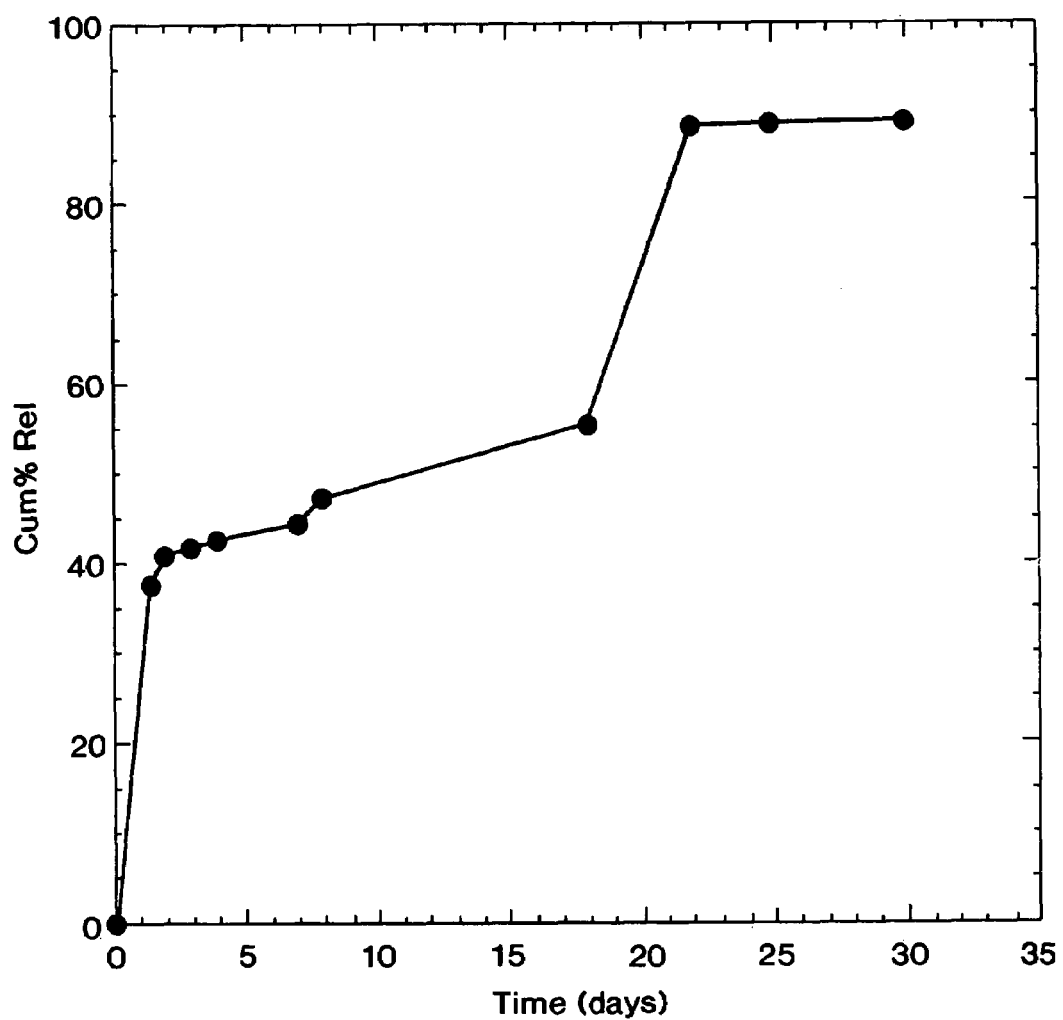
FIG. 12 shows the cumulative release of HI from PLGA microspheres. Formulation II (see example 7) of PLGA encapsulated microspheres were placed in 10 mM histidine, 10 mM NaCl, 0.02% polysorbate 20, 0.02% NaN$_3$, pH 7.2 and incubated at 37° C. The entire release medium was replaced at each sampling interval and the resulting release samples analyzed for bioactive insulin in an insulin kinase receptor assay (KIRA).
Figure 13A:
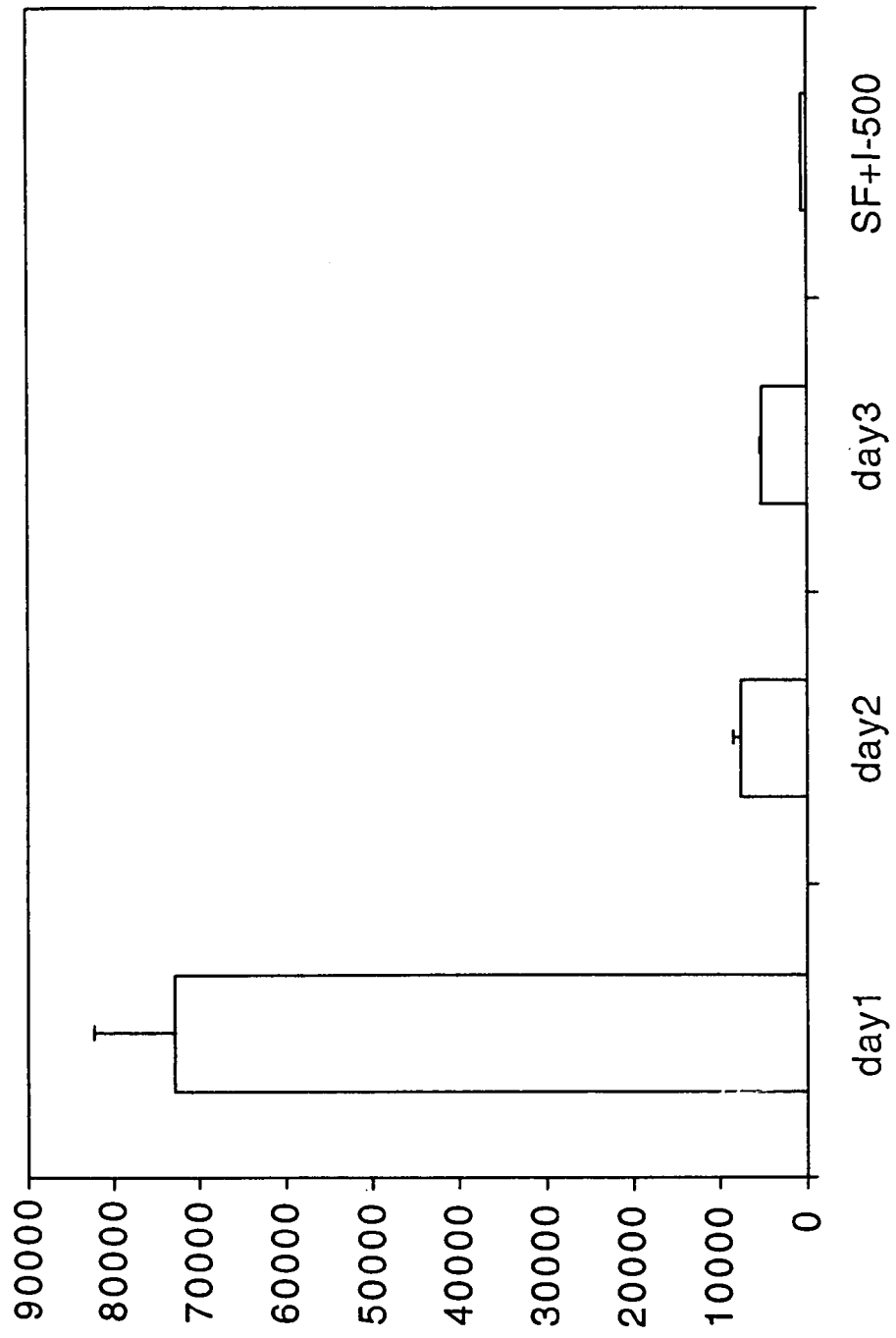
FIGS. 13A-13B show the release of insulin from PLGA encapsulation in synovial fluid. PLGA-Ins was incubated in synovial fluid harvested from rat knee joints, and samples were taken daily to test for insulin activity in an insulin kinase receptor assay (KIRA). As a control, synovial fluid spiked with insulin at 500 nM (SF+I-500) just before KIRA was also tested. Synovial fluid itself had no detectable insulin activity (data not shown).
Figure 13B:
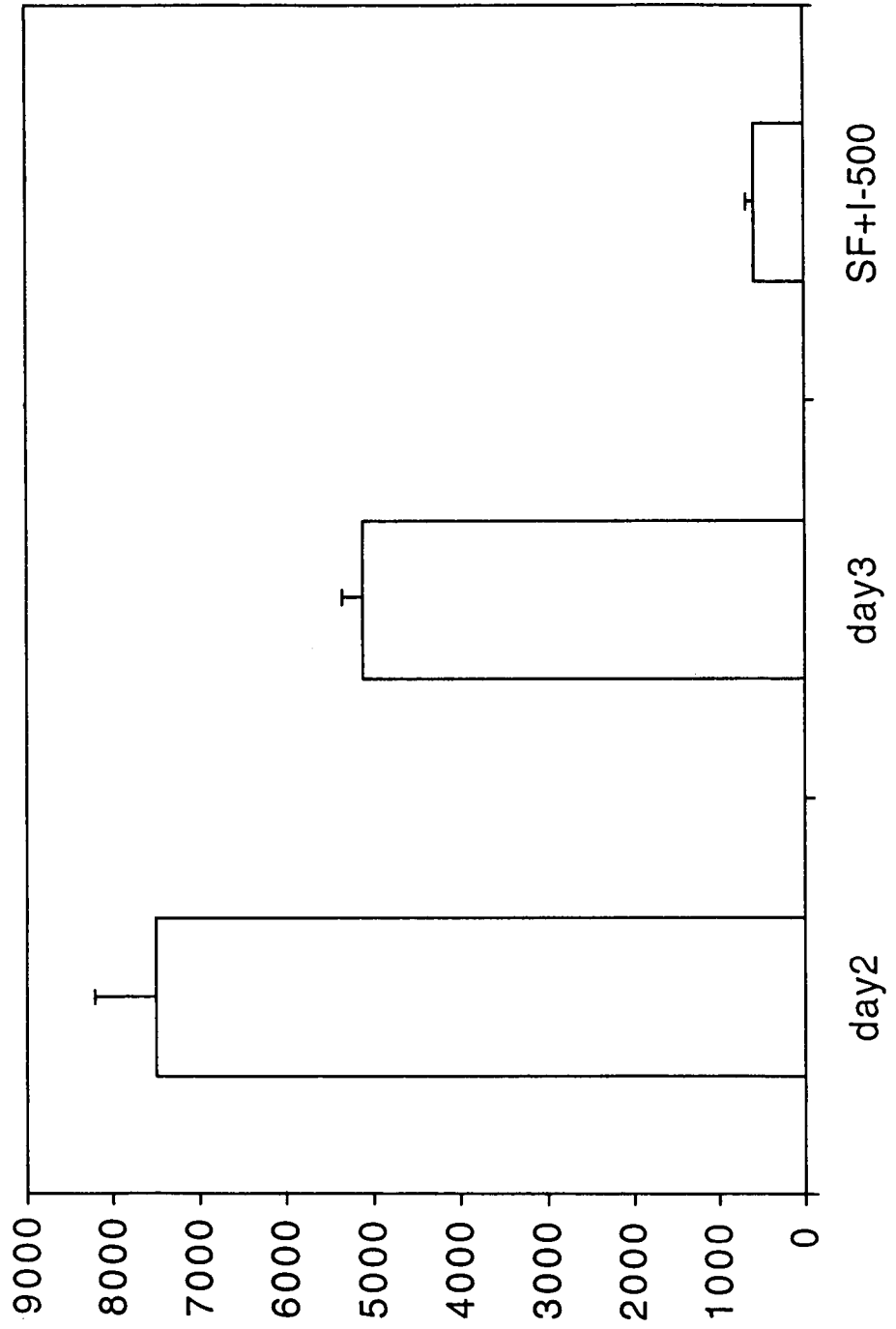

The insulin kinase receptor assay (KIRA) is a very sensitive assay which measures active insulin. An initial burst of release (at day 1) of protein was seen in both buffer (FIG. 12) and in synovial fluid (FIG. 13A). The release profiles of HI from formulation II (PLGA-Zn) indicated a biphasic release where almost 40% of the total loaded protein was released in the first 24 hours, followed by a lag phase (<1% daily release) and a second release phase (2-5% daily release) over the next 15 days at which point 89% of the total protein loaded had been released (FIG. 12). After incubation in synovial fluid for 3 days, microspheres from formulation II continued to release active insulin with a concentration of approximately 5 μM (1.67 mg/ml total). Thus, these results indicated that active insulin was released from the loaded microspheres and that the formulation process did not seem to be detrimental to protein quality.

Figure 14A:
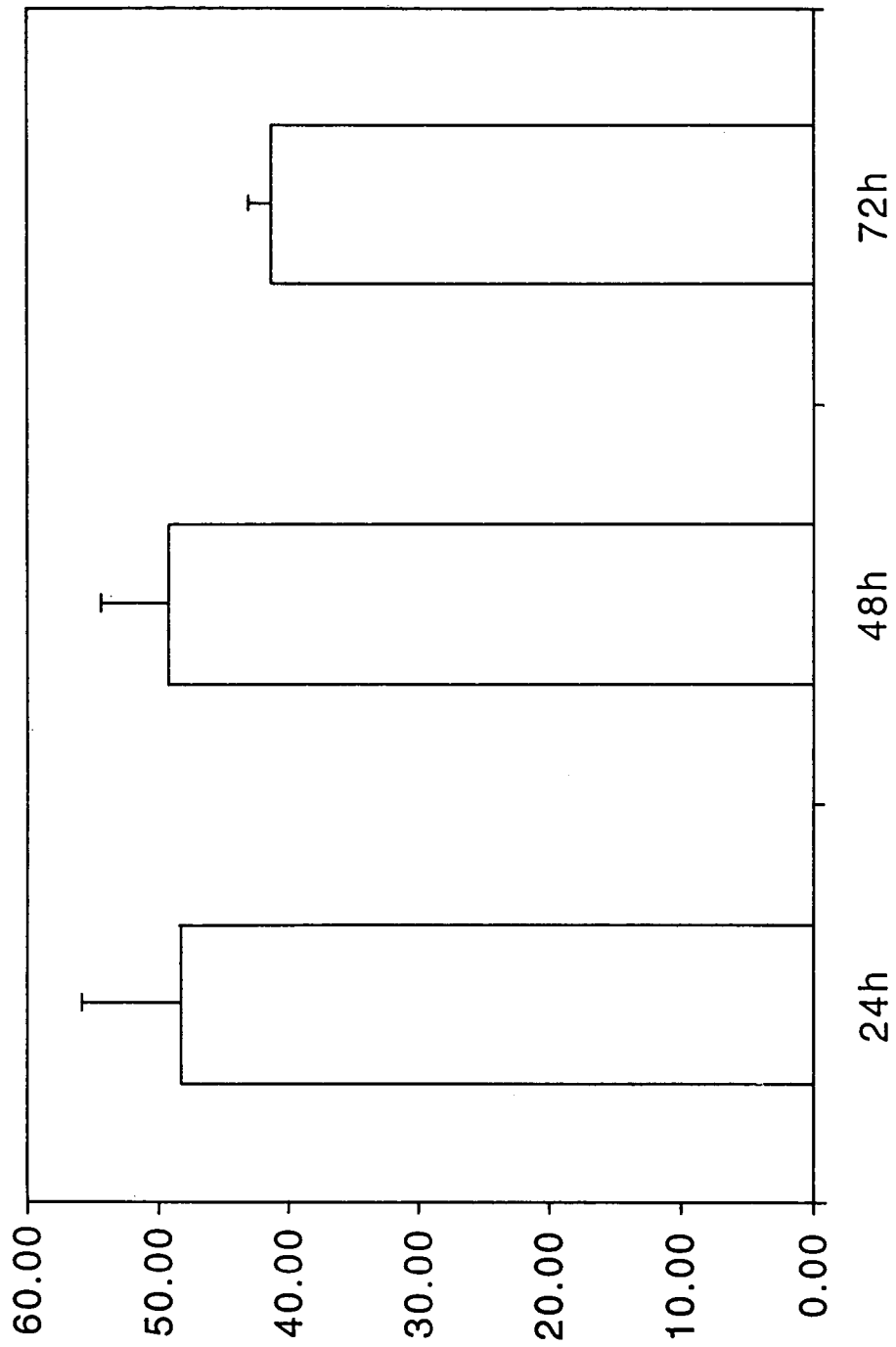
In FIG. 14A, samples were from insulin which was incubated in serum-free explant media at 37° C. and 5% $CO_2$.
Figure 14B:
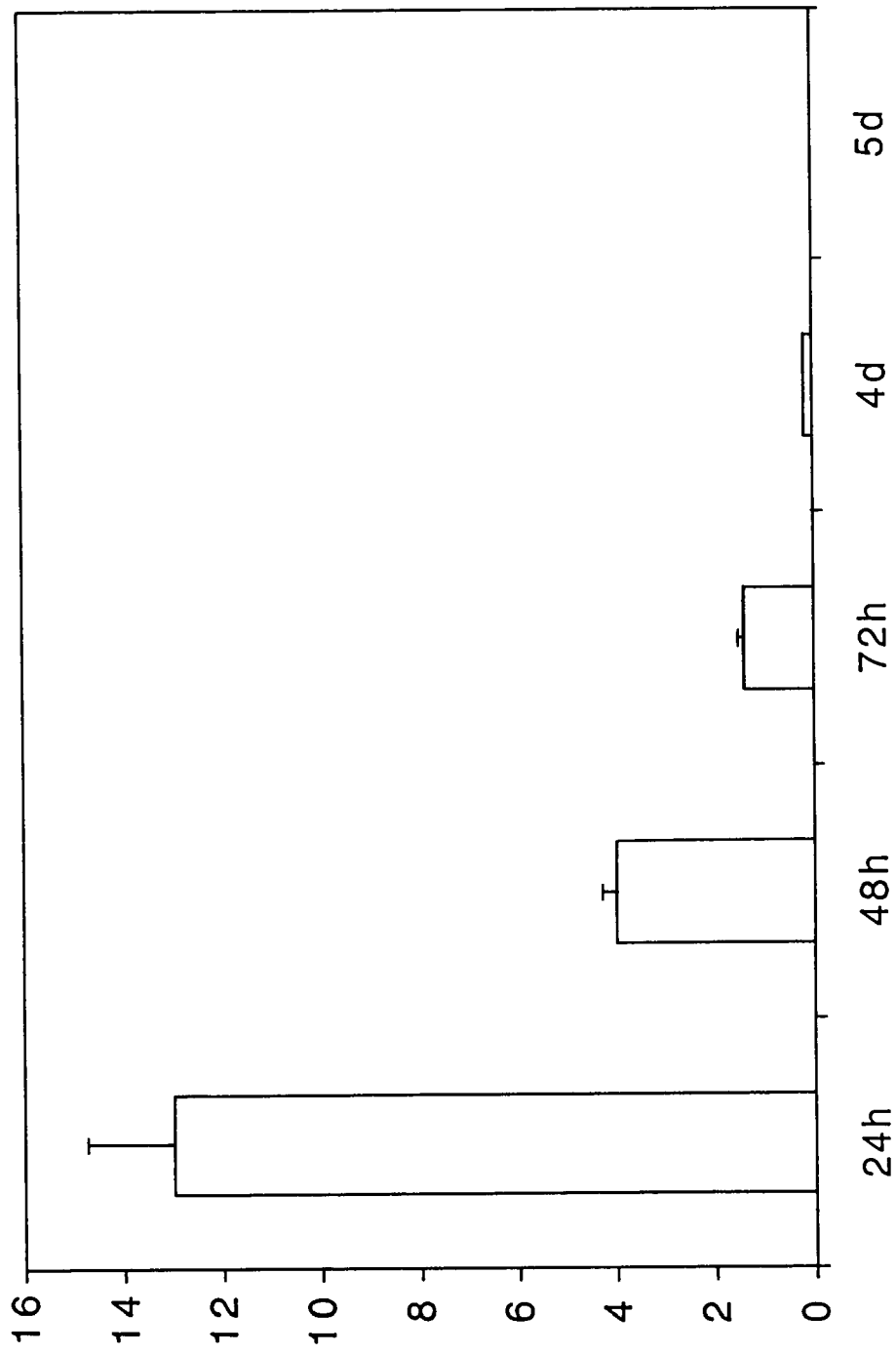
In FIG. 14B, the same insulin-media solution as in FIG. 14A was added to porcine articular cartilage explants.
Figure 14D:
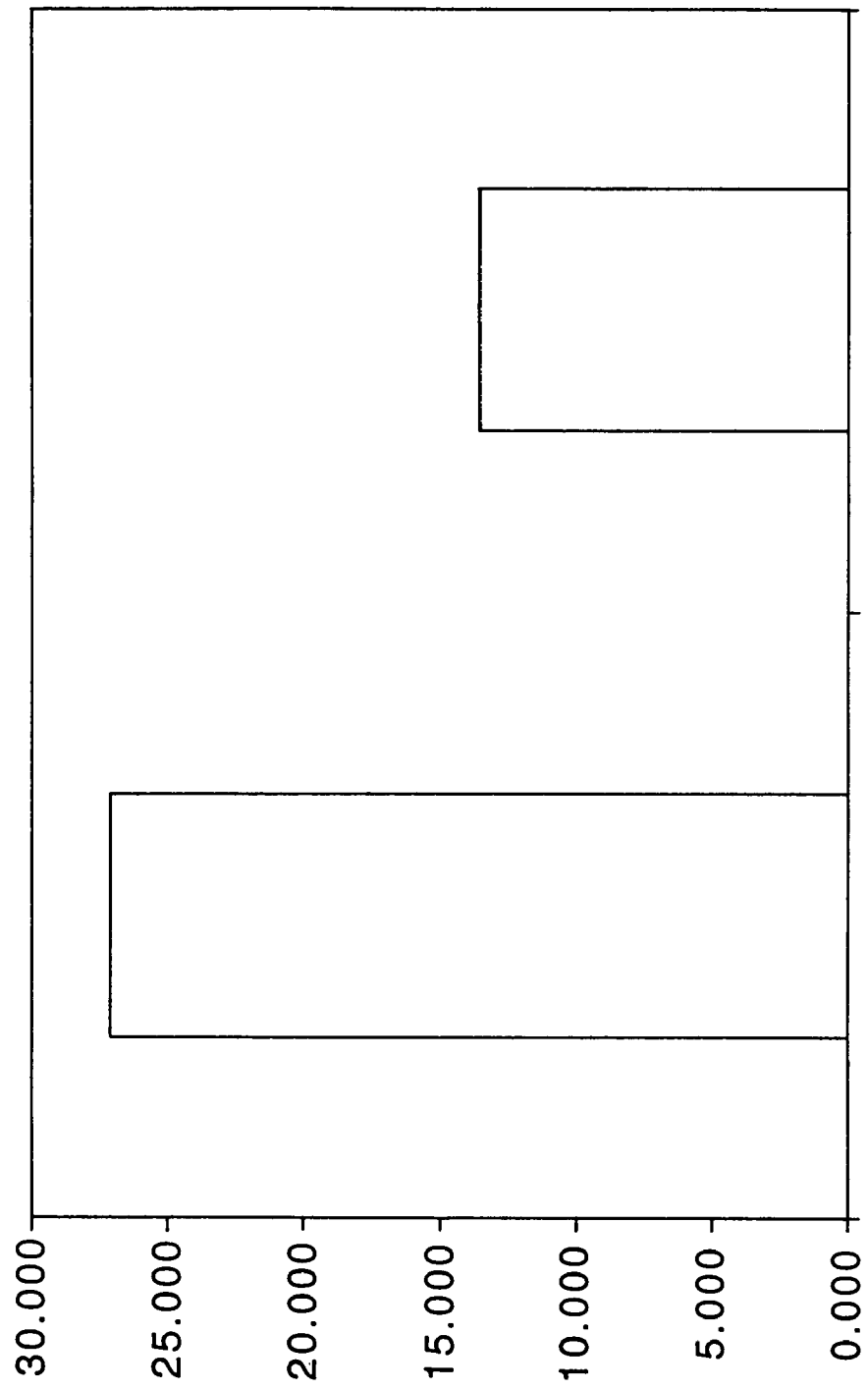
FIG. 14 shows the activity of insulin (by KIRA) in samples harvested daily from samples incubated at 37° C. and 5% $CO_2$ under various culture conditions. Each day media was harvested and tested for insulin activity in the insulin kinase receptor assay (KIRA). The results are expressed as nM concentration of active insulin.
In FIG. 14C, PLGA-microencapsulated insulin (PLGA-Ins) was added to explants, and in FIG. 14D, this PLGA-Ins solution was diluted 1:10 and added to explants.

The advantage such a slow-release system might have in vivo is illustrated by experiments testing insulin and insulin-loaded microspheres after incubation with articular cartilage explants. In this system, samples are treated only once, media is harvested on subsequent days, and cells are metabolically active during the course of the experiment. In this way, the stability of insulin in a biologically relevant system could be determined. While insulin remained fairly stable when cultured in media without tissue (at 37° C.) (FIG. 14A), in the presence of articular cartilage, the amount of active insulin decreased dramatically. In fact, within 24 hours after incubation with cartilage, the amount of active insulin had decreased by as much as 70%, and by 4 days of culture, little active insulin was detected (FIG. 14B). In contrast, significant levels of active insulin were found as late as 3 days after treatment with PLGA-Ins (14C). Furthermore, even when diluted PLGA-Ins microspheres were incubated with tissue, the amount of active insulin in the PLGA-Ins samples at 3 days was almost 14 times higher than that in the insulin samples at 3 days (FIG. 14D).

In conclusion, we have shown that PLGA-Ins microspheres continue to release active insulin over time in the presence of articular cartilage. Thus, insulin remains active and apparently unaltered after release from microspheres incubated in a biologically relevant system for several days. Taken together, our results suggest that PLGA-Ins which would be useful for local, slow-release delivery of insulin to the joint.

Example 8

Biological Activity of PLGA-Ins

Introduction

To verify that the insulin released from the PLGA-Ins microspheres was active on articular cartilage, we added these microspheres to articular cartilage explants and harvested and changed the media (without adding more PLGA-Ins) every day for three days. Activity was determined by measuring proteoglycan breakdown and synthesis as described above for articular cartilage explants (Example 2). As a control, we treated some explant samples with fresh insulin (10 nM) at each media change (i.e. at 0, 24, and 48 hr timepoints).

Data from explants cultures can be used to predict the effect of specific proteins on articular cartilage in vivo. However, within the joint several types of tissue besides cartilage are present. In addition, proteins can be rapidly cleared from the synovial fluid. Therefore, to determine whether or not insulin released from PLGA-Ins microspheres had an effect on cartilage in vivo, we injected mouse knee joints with PLGA-Ins microspheres and measured proteoglycan synthesis.

Materials and Methods

Effect of PLGA-Ins Microspheres on Proteoglycan Release and Synthesis:

Explants were treated with PLGA-Ins microspheres (3 μl of a solution of microspheres resuspended in 0.5 ml of explant media were added to explants in 260 ul of media) on day 0, and media was harvested and replaced (without microspheres) on subsequent days. Proteoglycan breakdown and synthesis were measured as described above (example 2, articular cartilage explants). Some explant samples were treated with fresh insulin (10 nM) at each media change (i.e. at 0, 24, and 48 hr timepoints).

Intra-Articular Injections:

PLGA-Ins microspheres were resuspended in 500 μl of buffer (0.1% hyaluronic acid in phosphate-buffered saline), and 3 μl of this solution was injected intra-articularly into mousejoints. As a control, 3 μl of buffer was injected into the contralateral knee. Three days later, patellae were harvested and proteoglycan synthesis was determined as above (example 3, patella assay).

Results and Discussion

Figure 15A:
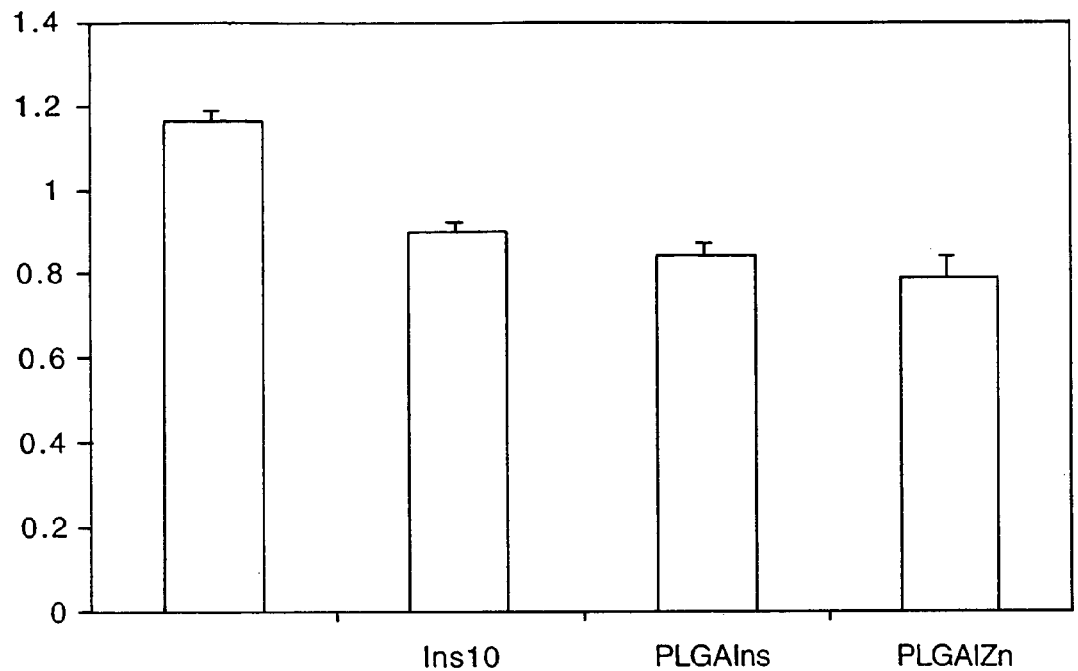
FIGS. 15A-F shows the effect of PLGA-Ins on cartilage explants.
Figure 15B:
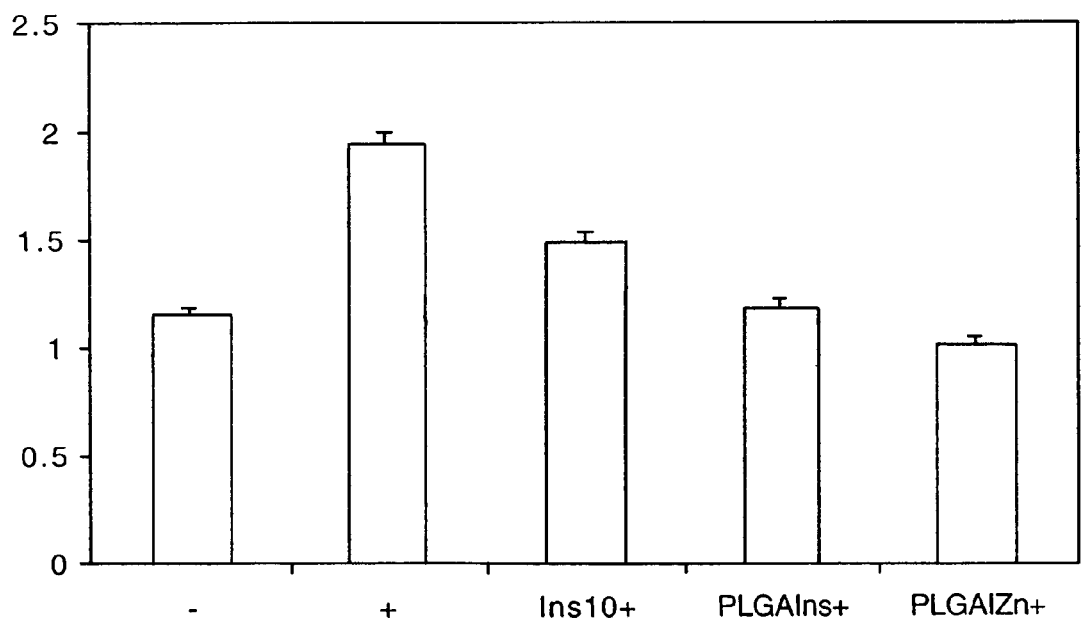
Figure 15C:
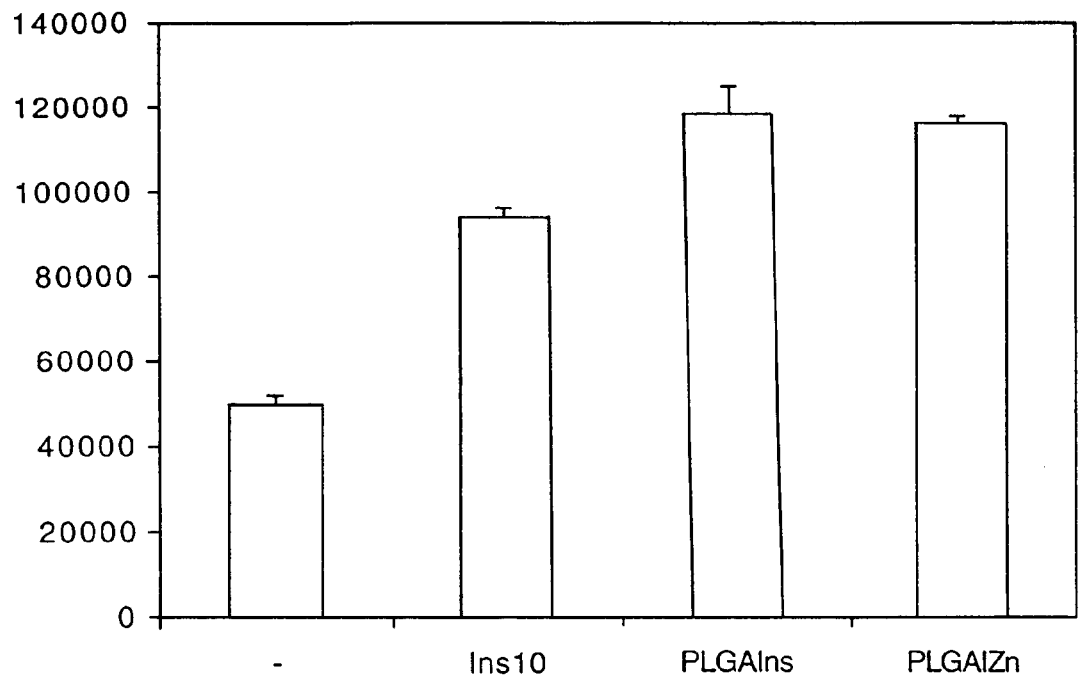
Figure 15D:
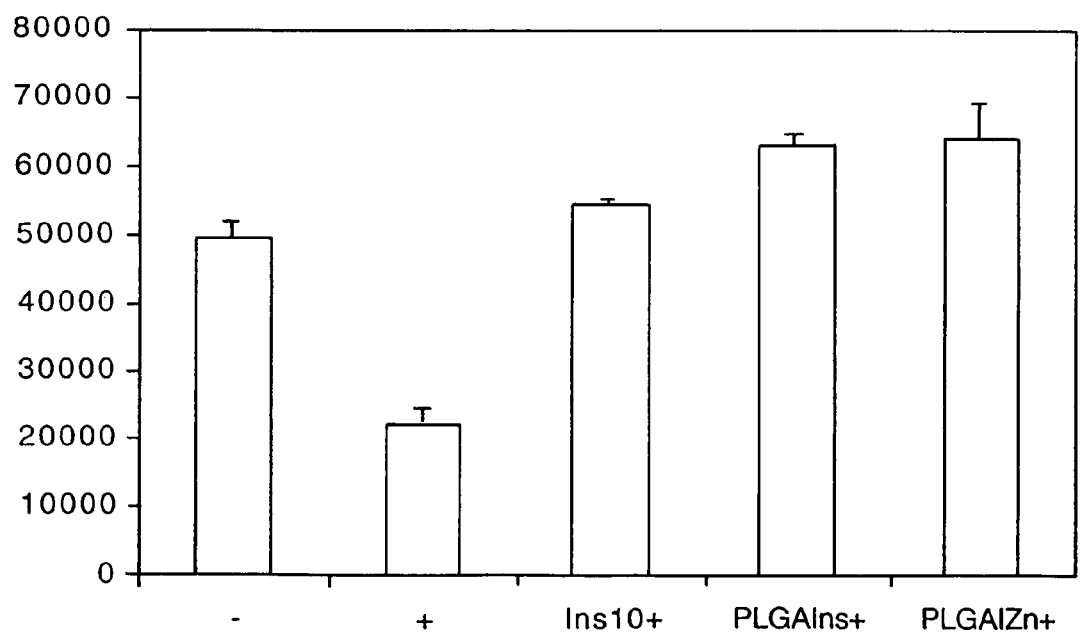
Figure 15E:
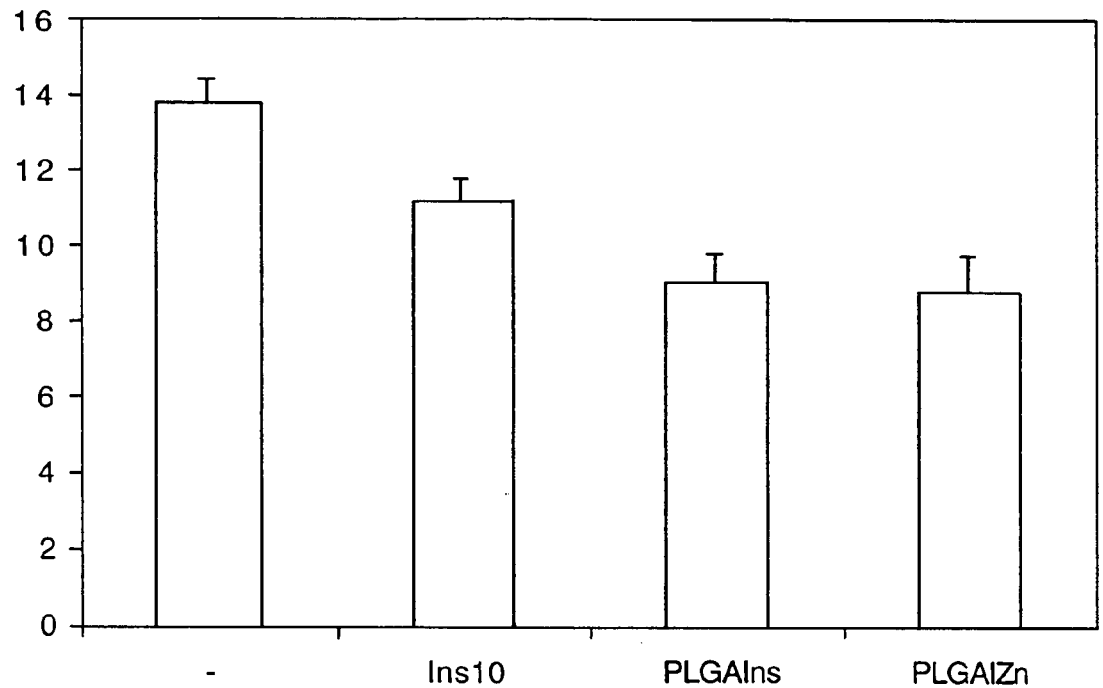
Figure 15F:
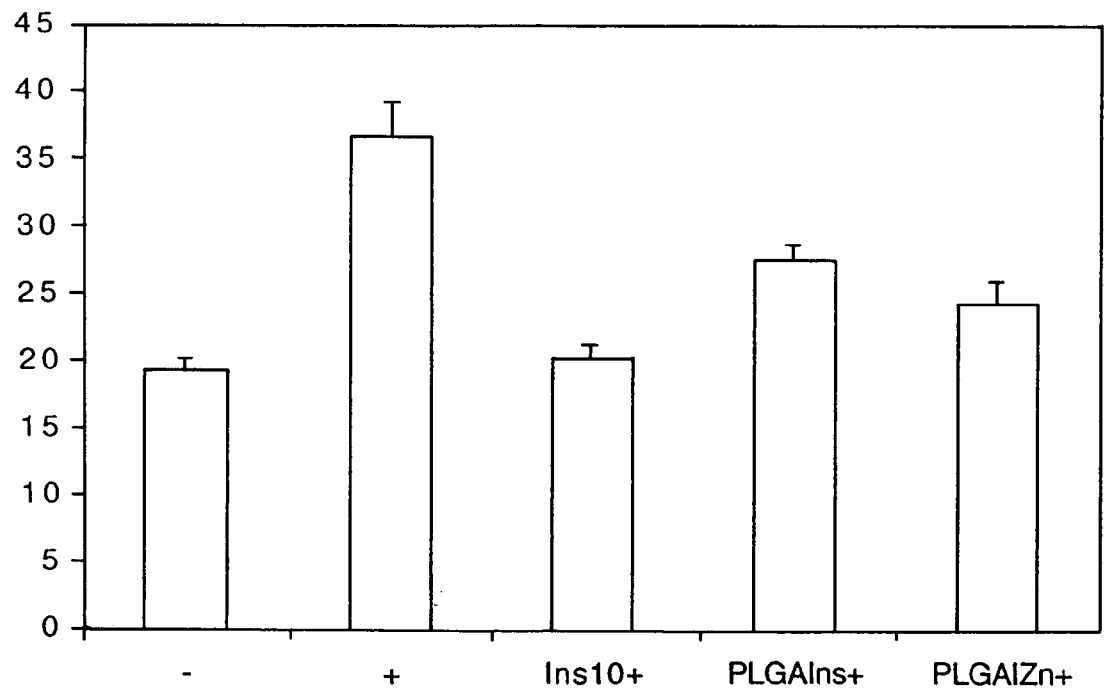

Explants treated with PLGA-Ins microspheres showed decreased matrix breakdown (FIG. 15A) and increased matrix synthesis (FIG. 15C). In addition, the ability of IL-1α to induce breakdown down (FIG. 15B) and inhibit matrix synthesis (FIG. 15D) were prevented by co-treatment with PLGA-Ins (FIGS. 15A-B). Finally, PLGA-Ins inhibited both basal (FIG. 15E) and IL-1α induced (FIG. 15F) nitric oxide production. These results suggest that PLGA-Ins could inhibit the cartilage catabolism and loss which occurs in cartilage disorders such as arthritis.

Figure 16:
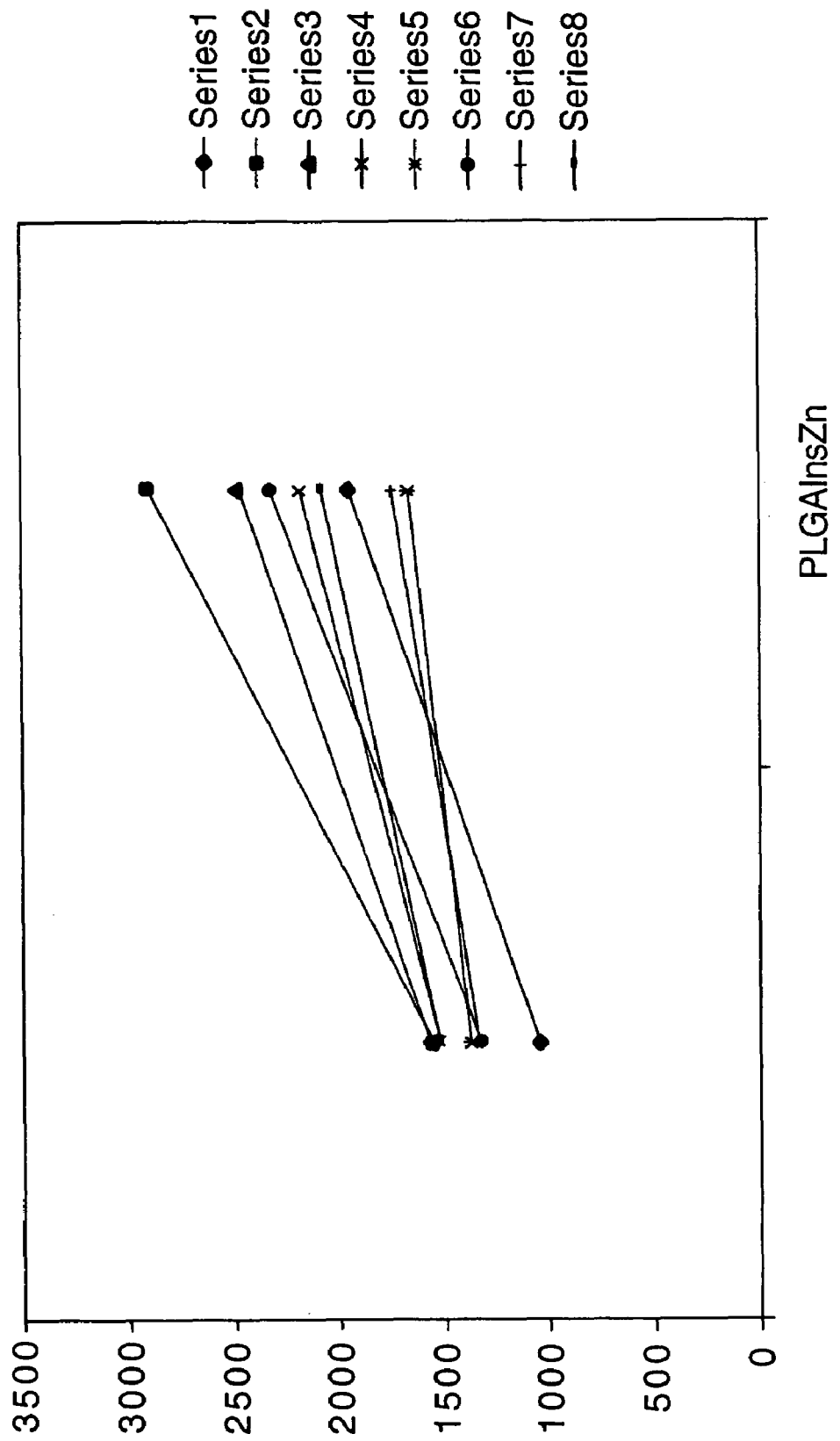
FIG. 16 shows the in vivo effect of PLGA-insulin. PLGA-Ins was injected into the articular space of the hind leg of mice. Buffer (PBS+0.1% BSA) was injected into the contralateral knee as a control (−). Results are expressed as amount of radioactivity (cpm)/patella. Each line represents a single mouse.

Three days after injection of PLGA-Ins into mouse knee joints, matrix synthesis was significantly ($p<0.05$) stimulated relative to the contralateral, buffer-injected joint FIG. 16). Thus, even under conditions in which insulin could be cleared from the synovial fluid and/or taken up by surrounding tissues and cells, articular cartilage has an anabolic response to the insulin released by the PLGA-Ins microspheres.

Taken together, our results clearly demonstrate that insulin mitigated loss of matrix molecules such as proteoglycans as well as stimulated synthesis of new molecules to replace those lost. The net effect was to increase the total amount of proteoglycans within a given amount of cartilage tissue. This effect of insulin was shown in vitro and in vivo. Finally, we have created a slow-release formulation of insulin using PLGA as a carrier. These PLGA-Ins microspheres appear to have superior stability and activity relative to that of insulin alone.

Example 9

Human Cartilage Explants

It has been well established that the GH/IGF/IGFBP system is involved in the regulation of anabolic and metabolic homeostasis and that defects in this system may adversely affect growth, physiology, and glycemic control (Jones et al., *Endocr. Rev.*, 16: 3-34 (1995); Davidson, *Endocr. Rev.*, 8: 115-131 (1987); Moses, *Curr. Opin. Endo. Diab.*, 4: 16-25 (1997)).

IGF-1 has been proposed for the treatment or prevention of osteoarthritis, because of its ability to stimulate both matrix synthesis and cell proliferation in culture (Osborn, *J. Orthop. Res.*, 7: 35-42 (1989)). IGF-1 has been administered with sodium pentosan polysulfate (PPS) (a chondrocyte catabolic activity inhibitor) to severely osteoarthritic canines with the effect of reducing the severity of the disease by lowering the levels of active neutral metalloproteinase in the cartilage. In the model of mildly osteoarthritic canines, therapeutic intervention with IGF-1 and PPS together appeared to successfully maintain cartilage structure and biochemistry, while IGF alone was ineffective, as described in Rogachefsky, *Osteoarthritis and Cartilage*, 1: 105-114 (1993); Rogachefsky et al., *Ann. NY Acad. Sci.*, 732: 889-895 (1994). The use of IGF-1 either alone or as an adjuvant with other growth factors to stimulate cartilage regeneration has been described in WO 91/19510, WO 92/13565, U.S. Pat. No. 5,444,047, and EP 434,652.

IGF-1 has also been found useful in the treatment of osteoporosis in mammals exhibiting decrease bone mineral density and those exposed to drugs or environmental conditions that result in bone density reduction and potentially osteoporosis, as described in EP 560,723 and EP 436,469.

IGF-1 insufficiency may have an etiologic role in the development of osteoarthritis (Coutts et al., "Effect of growth factors on cartilage repair," *Instructional Course Lect.*, 47: 487-494 (Amer. Acad. Orthop. Surg.: Rosemont, Ill. 1997)). Some studies indicate that serum IGF-1 concentrations are lower in osteoarthritc patients than control groups, while other studies have found no difference. Nevertheless, it has been shown that both serum IGF-1 levels and chrondrocyte responsiveness to IGF-1 decrease with age, with the latter likely due to high levels of IGF-BPs (Florini and Roberts, *J. Gerontol.*, 35: 23-30 (1980); Martin et al., *J. Orthop. Res.*, 15: 491-498 (1997); Fernihough et al., *Arthr. Rheum.* 39: 1556-1565 (1996)). Thus, both the decreased availability of IGF-1 as well as diminished chondrocyte responsiveness/disregulation of IGFBPs thereto may contribute to the impaired cartilage matrix homeostasis and tissue degeneration that occurs with advancing age and disease.

The biological function of IGF binding proteins (IGFBPs) is not known. Of the IGFBPs, IGFBP-3 appears to be the IGFBP most responsible for regulating the total levels of IGF-1 and IGF-2 in plasma. IGFBP-3 is a GH-dependent protein and is reduced in cases of GH-deficiency or resistance (Jones et al., supra; Rosenfield et al., "IGF-1 treatment of syndromes of growth hormone insensitivity" In: *The insulin-like growth factors and their regulatory proteins*, Eds Baxter R C, Gluckman P D, Rosenfield R G. Excerpta Medica, Amsterdam, 1994), pp 357-464; Scharf et al., *J. Hepatology*, 25: 689-699 (1996)). IGFBPs are able to enhance of inhibit IGF activity, depending largely on their post-translational modifications and tissue localization (reviewed in Jones and Clemmons, *Endocr. Rev.* 16:3-34 (1995); Collet-Solberg and Cohen, *Endocrinol. Metabol. Clin. North Am.* 25:591-614 (1996)). In addition, disregulation in IGFBPs (3,4 and/or 5) may play a key role in arthritic disorders (Chevalier and Tyler, *Brit. J. Rheum.* 35: 515-522 (1996); Olney et al., *J. Clin. Endocrinol. Metab.* 81: 1096-1103 (1996); Martel-Pelletier et al., *Inflamm. Res.*, 47: 90-100 (1998)). It has been reported that IGF-1 analogs with very low binding affinity for IGF-BPs were more effective than wild-type IGF-1 in stimulating proteoglycan synthesis (Morales, *Arch Biochem. Biophys.* 324, 173-188 (1997)). More recent data, however, suggest that IGFBPs contribute to IGF binding to and transport through cartilage tissue, and IGFBPs may thus regulate bioavailability of IGF-1 within the joint (Bhatka et al. *J. Biol. Chem.* 275: 5860-5866 (2000)).

WO 94/04569 discloses a specific binding molecule, other than a natural IGFBP, that is capable of binding to IGF-1 and can enhance the biological activity of IGF-1. WO 98/45427 published Oct. 15, 1998; Lowman et al., *Biochemistry,* 37: 8870-8878 (1998); and Dubaquie and Lowman, *Biochemistry,* 38: 6386 (1999) disclose IGF-1 agonists identified by phage display. Also, WO 97/39032 discloses ligand inhibitors of IGFBP's and methods for their use. Further, U.S. Pat. No. 5,891,722 discloses antibodies having binding affinity for free IGFBP-1 and devices and methods for detecting free IGFBP-1 and a rupture in a fetal membrane based on the presence of amniotic fluid in a vaginal secretion, as indicated by the presence of free IGFBP-1 in the vaginal secretion.

Figure 19A:
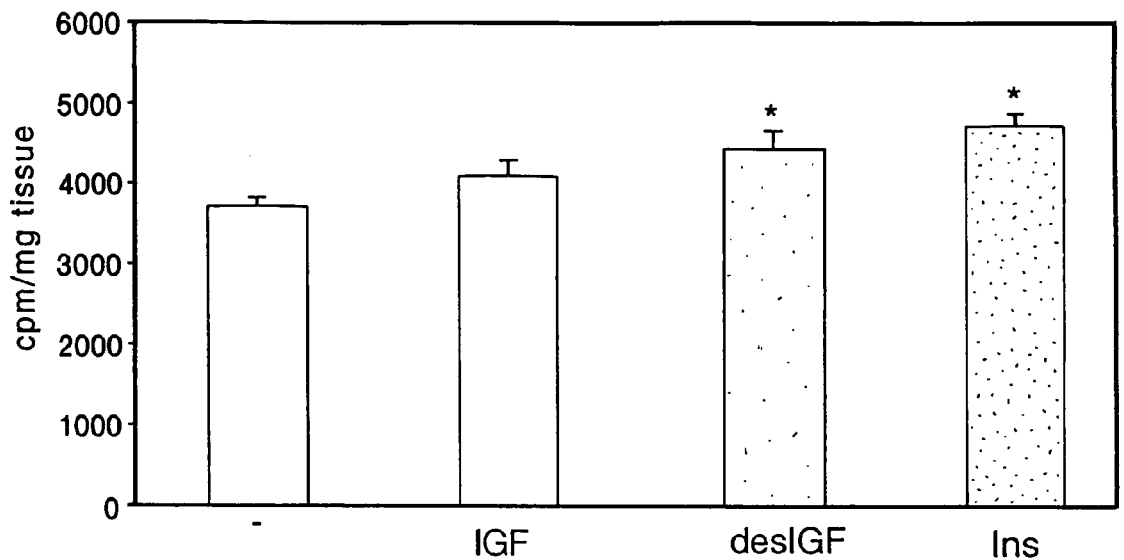
FIGS. 19A and 19B show the effect on matrix synthesis on human articular cartilage of IGF, IGF mutant which does not bind to IGF BPs and insulin. Shown is that insulin (Ins), but not IGF-1 (IGF) induces cartilage matrix synthesis in articular cartilage. Tissues were treated with the indicated agents for 24 hours during which proteoglycan synthesis was measured by labeling cartilage with $^{35}$S-sulphate.
Figure 19B:
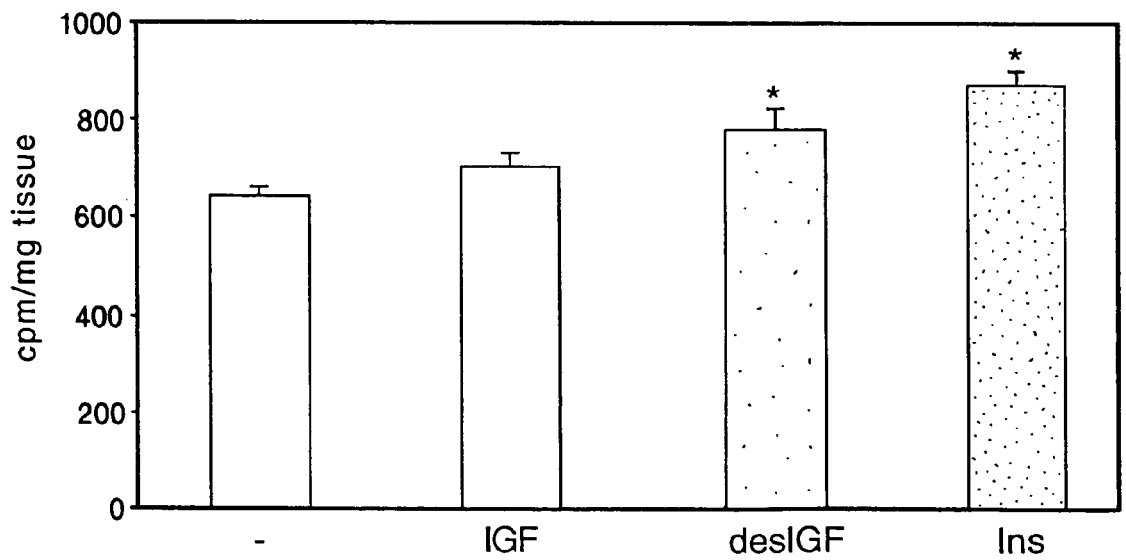

Results and Discussion:

IGF-1 is a key regulator of matrix homeostasis in articular cartilage. The metabolic imbalance in osteoarthritis that favors matrix breakdown over new matrix synthesis may be due, at least in part, to insensitivity of chondrocytes to IGF-1 stimulation. While the mechanism underlying this IGF-1 resistance is not known, without being limited to any one theory, it is believed that IGF-binding proteins (IGFBPs), which are elevated in many OA patients, play a role. In these patients, proteins with IGF-1-like activity, which do not bind to, and are thus not inhibited by, IGFBPs would likely stimulate cartilage repair in tissue that is otherwise IGF-1 resistant. As exemplified by FIG. 19, we have found that at least 20% of patients undergoing joint replacement have articular cartilage which is not responsive to IGF-I. However, the cartilage of these patients does respond to insulin, which does not bind to IGFBPs, by inducing significant synthesis of new cartilage matrix molecules (FIGS. 19A,B). The fact that an IGF-I mutant, desIGF, which does not bind to IGFBPs, induces cartilage matrix synthesis in these IGF-I resistant tissues (FIGS. 19A,B), suggests that the mechanism underlying IGF-1 resistance in this system is increased production of inhibitory IGF-BPs. Thus, human, diseased cartilage remains responsive to the anabolic effects of insulin, and as such, insulin is likely to have beneficial effects on cartilage within diseased joints. In addition, insulin is expected to have anabolic effects on tissues, such as arthritic cartilage, which are otherwise IGF-1 resistant.

Example 10

Expression of Insulin or Insulin Variants in *E. coli*

This example illustrates preparation of an unglycosylated form of insulin or insulin variants by recombinant expression in *E. coli*.

The DNA sequence encoding the insulin or insulin variant is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene,* 2:95 (1977)) which contains genes for ampicillin and tetracycline resistance. The vector is digested with restriction enzyme and dephosphorylated.

The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the insulin/insulin variant coding region, lambda transcriptional terminator, and an argu gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized insulin or insulin variant protein can then be purified using a metal chelating column under conditions that allow tight binding of the protein.

Insulin or insulin variant may also be expressed in *E. coli* in a poly-His tagged form, using the following procedure. The DNA encoding insulin or insulin variant is initially amplified using selected PCR primers. The primers contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate $2H_2$ O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. Depending on condition, the clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein were pooled and stored at 4° C. Protein concentration is estimated by its absorbance at 280 nm using the calculated extinction coefficient based on its amino acid sequence.

The proteins are refolded by diluting sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded insulin or insulin variant proteins, respectively, are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 11

Expression of Insulin or Insulin Variants in Mammalian Cells

This example illustrates preparation of a potentially glycosylated form of insulin or insulin variants by recombinant expression in mammalian cells.

The vector, pRK5 (see EP 307,247, published Mar. 15, 1989), is employed as the expression vector. Optionally, the insulin or insulin variant DNA is ligated into pRK5 with selected restriction enzymes to allow insertion of the insulin or insulin variant DNA using ligation methods such as described in Sambrook et al., supra. The resulting vector is called, for example, pRK5-ins.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-ins DNA is mixed with about 1 µg DNA encoding the VA RNA gene [Thimmappaya et al., Cell, 31:543 (1982)] and dissolved in 500 µL of 1 mM Tris-HCl, 0.1 mM EDTA, 0.227 M $CaCl_2$. To this mixture is added, dropwise, 500 µL of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 uCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of insulin or insulin variant polypeptide. The cultures containing transfected cells may undergo further incubation (in serum free medium) and the medium is tested in selected bioassays.

In an alternative technique, insulin or insulin variant may be introduced into 293 cells transiently using the dextran sulfate method described by Somparyrac et al., Proc. Natl. Acad. Sci., 12:7575 (1981). 293 cells are grown to maximal density in a spinner flask and 700 µg pRK5-ins DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed insulin or insulin variant can then be concentrated and purified by any selected method, such as dialysis and/or column chromatography.

In another embodiment, insulin or insulin variant can be expressed in CHO cells. The pRK5-ins can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of insulin or insulin variant, the culture medium may be replaced with serum free medium. Preferably, the cultures are incubated for about 6 days, and then the conditioned medium is harvested. The medium containing the expressed insulin or insulin variant can then be concentrated and purified by any selected method.

Epitope-tagged insulin or insulin variant may also be expressed in host CHO cells. The insulin or insulin variant may be subcloned out of the pRK5 vector. The subclone insert can undergo PCR to fuse in frame with a selected epitope tag such as a poly-his tag into a Baculovirus expression vector. The poly-his tagged insulin or insulin variant insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged insulin or insulin variant can then be concentrated and purified by any selected method, such as by $Ni^{2+}$-chelate affinity chromatography.

Insulin or insulin variant may also be expressed in CHO and/or COS cells by a transient expression procedure or in CHO cells by another stable expression procedure.

Stable expression in CHO cells may be performed using the procedure outlined below. The proteins may be expressed, for example, either (1) as an IgG construct (immunoadhesion), in which the coding sequences for the soluble forms (e.g., extracellular domains) of the respective proteins are fused to an IgG constant region sequence containing the hinge CH2 domain and/or (2) a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNAs. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately $3 \times 10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2 \times 10^6$ cells/mL. On day 0, the cell number pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at –80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 12

Expression of Insulin or Insulin Variant in Yeast

The following method describes recombinant expression of insulin or insulin variant in yeast.

First, yeast expression vectors are constructed for intracellular production or secretion of insulin or insulin variant from the ADH2/GAPDH promoter. DNA encoding insulin or insulin variant and the promoter is inserted into suitable restriction enzyme sites in the selected plasmid to direct intracellular expression of the insert. For secretion, DNA encoding the insert can be cloned into the selected plasmid, together with DNA encoding the ADH2/GAPDH promoter, a native signal peptide or other heterologous mammalian signal peptide, or, for example, a yeast alpha-factor or invertase secretory signal/leader sequence, and linker sequences (if needed) for expression of the insert.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant insulin or insulin variant can subsequently be isolated and purified by removing the yeast cells from the fermentation medium by centrifugation and then concentrating the medium using selected cartridge filters. The concentrate containing the crude polypeptide may further be purified using selected column chromatography resins.

Example 13

Expression of Insulin or Insulin Variant in Baculovirus-Infected Insect Cells

The following method describes recombinant expression of insulin or insulin variant in Baculovirus-infected insect cells.

The sequence coding for insulin or insulin variant is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding insulin or insulin variant or the desired portion of the coding sequence of this polypeptide [such as the sequence encoding the extracellular domain of a transmembrane protein or the sequence encoding the mature protein if the protein is extracellular] is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold® virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged insulin or insulin variant can then be purified, for example, by $Ni^{2+}$-chelate affinity chromatography as follows. Extracts are prepared from recombinant virus-infected Sf9 cells as described by Rupert et al., *Nature*, 362: 175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged insulin or insulin variant are pooled and dialyzed against loading buffer.

Alternatively, purification of the IgG tagged (or Fc tagged) insulin or insulin variant can be performed using known chromatography techniques, including for instance, Protein A or Protein G column chromatography.

Alternatively still, the insulin or insulin variant molecules of the invention may be expressed using a modified baculovirus procedure employing Hi-5 cells. In this procedure, the DNA encoding the desired sequence was amplified with suitable systems, such as Pfu (Stratagene), or fused upstream (5'-of) an epitope tag contained within a baculovirus expression vector. Such epitope tags include poly-His tags and immunoglobulin tags (like Fc regions of IgG). A variety of plasmids may be employed, including plasmids derived from commercially available plasmids such as pIE-1 (Novagen). The pIE1-1 and pIE1-2 vectors are designed for constitutive expression of recombinant proteins from the baculovirus ie1 promoter in stably transformed insect cells. The plasmids differ only in the orientation of the multiple cloning sites and contain all promoter sequences known to be important for ie1-mediated gene expression in uninfected insect cells as well as the hr5 enhancer element. pIE1-1 and pIE1-2 include the ie1translation initiation site and can be used to produce fusion proteins. Briefly, the desired sequence or the desired portion of the sequence (such as the sequence encoding the extracellular domain of the transmembrane protein) is amplified by PCR with primers complementary to the 5' and 3' regions. The 5' primer may incorporate flanking (selected) restriction enzyme sites. The product was then digested with those selected restriction enzymes and subcloned into the expression vector. For example, derivatives of pIE1-1 can include the Fc region of human IgG (pb.PH.IgG) or an 8 histidine (pb.PH.His) tag downstream (3'-of) the desired sequence. Preferably, the vector construct is sequenced for confirmation.

Hi5 cells are grown to a confluency of 50% under the conditions of 27° C., no $CO_2$, no pen/strep. For each 150 mm plate, 30 µg of pIE based vector containing the sequence was mixed with 1 ml Ex-Cell medium (Media: Ex-Cell 401+1/ 100 L-Glu JRH Biosciences #14401-78P (note: this media is light sensitive)). Separately, 100 µl of Cell Fectin (CellFECTIN, Gibco BRL +10362-010, pre-vortexed) is mixed with 1 ml of Ex-Cell medium. The two solutions are combined and incubated at room temperature for 15 minutes. 8 ml of Ex-Cell media is added to the 2 ml of DNA/CellFECTIN mix and this is layered on Hi5 cells that have been washed once with Ex-Cell media. The plate is then incubated in darkness for 1 hour at room temperature. The DNA/CellFECTIN mix is then aspirated, and the cells are washed once with Ex-Cell to remove excess Cell FECTIN. 30 ml of fresh Ex-Cell media is added and the cells are incubated for 3 days at 28° C. The supernatant is harvested and the expression of the sequence in the baculovirus expression vector is determined by batch binding of 1 ml of supernatant to 25 ml of Ni-NTA beads (QIAGEN) for histidine tagged proteins or Protein-A Sepharose CL-4B beads (Pharmacia) for IgG tagged proteins followed by SDS-PAGE analysis comparing to a known concentration of protein standard by Coomassie blue staining.

The conditioned media from the transfected cells (0.5 to 3 L) was harvested by centrifugation to remove the cells and filtered through 0.22 micron filters. For the poly-His tagged constructs, the protein comprising the sequence is purified using a Ni-NTA column (Qiagen). Before purification, imidazole at a flow rate of 4-5 ml/min. at 48° C. After loading, the column is washed with additional equilibrium buffer and the protein eluted with equilibrium buffer containing 0.25M imidazole. The highly purified protein was then subsequently desalted into a storage buffer containing 10 mM Hepes, 0.14 M NaCl and 4% mannitol, pH 6.8 with a 25 ml G25 Superfine (Pharmacia) column and stored at −80° C.

Immunoadhesion (Fc-containing) constructs may also be purified from the conditioned media as follows: The conditioned media is pumped onto a 5 ml Protein A column (Pharmacia) which had been previously equilibrated in 20 mM sodium phosphate buffer, pH 6.8. After loading, the column is washed extensively with equilibrium buffer before elution with 100 mM citric acid, pH 3.5. The eluted protein is immediately neutralized by collecting 1 ml fractions into tubes containing 275 µl of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 14

Preparation of Antibodies that Bind Insulin or Insulin Variants

This example illustrates preparation of monoclonal antibodies which can specifically bind insulin or insulin variants.

Techniques for producing the monoclonal antibodies are known in the art and are described, for instance, in Goding, supra. Immunogens that may be employed include purified insulin or insulin variants, fusion proteins containing insulin or insulin variants, and cells expressing recombinant insulin or insulin variant on the cell surface. Selection of the immunogen can be made by the skilled artisan without undue experimentation.

Mice, such as Balb/c, are immunized with the insulin or insulin variant immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-insulin or anti-insulin variant antibodies.

After a suitable antibody titer has been detected, the animals "positive" for antibodies can be injected with a final intravenous injection of insulin or insulin variant. Three to four days later, the mice are sacrificed and the spleen cells are harvested. The spleen cells are then fused (using 35% polyethylene glycol) to a selected murine myeloma cell line such as P3X63AgU1, available from ATCC, No. CRL 1597.

The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells are screened in an ELISA for reactivity against insulin or insulin variant. Determination of "positive" hybridoma cells secreting the desired monoclonal antibodies against insulin or insulin variant is within the skill in the art.

The positive hybridoma cells can be injected intraperitoneally into syngeneic Balb/c mice to produce ascites containing the anti-insulin or anti-insulin variant monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 15

Purification of Insulin or Insulin Variant Polypeptides Using Specific Antibodies Native or recombinant insulin or insulin variant polypeptides may be purified by a variety of standard techniques in the art of protein purification. For example, pro-insulin or pro-insulin variant polypeptide, mature insulin or insulin variant polypeptide, or pre-insulin/pre-insulin variant polypeptide can be purified by immunoaffinity chromatography using antibodies specific for the polypeptide of interest. In general, an immunoaffinity column is constructed by covalently coupling the anti-insulin or anti-insulin variant polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared form mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of insulin or insulin variant polypeptide by preparing a fraction from cells containing insulin or insulin variant polypeptide in a soluble form. This preparation is derived by solubilization of the whole cell or of a subcellular fraction obtained via differential centrifugation by the addition of detergent or by other methods well known in the art. Alternatively, soluble insulin or insulin variant polypeptide containing a signal sequence may be secreted in useful quantity into the medium in which the cells are grown.

A soluble insulin or insulin variant polypeptide-containing preparation is passed over the immunoaffinity column, and the column is washed under conditions that allow the preferential absorbance of insulin or insulin variant polypeptide (e.g., high ionic strength buffers in the presence of detergent). Then, the column is eluted under conditions that disrupt antibody/antigen binding (e.g., a low pH buffer such as approximately pH 2-3, or a high concentration of a chaotrope such as urea or thiocyanate ion), and insulin or insulin variant polypeptide is collected.

Example 16

Rational Drug Design

The goal of rational drug design is to produce structural analogs of biologically active polypeptide of interest (i.e., an insulin or insulin variant polypeptide) or of small molecules with which they interact, e.g., agonists, antagonists, or inhibitors. Any of these examples can be used to fashion drugs which are more active or stable forms of the insulin or insulin variant polypeptide or which enhance or interfere with the function of this polypeptide in vivo (c.f., Hodgson, *Bio/Technology* 9: 19-21 (1991)).

Insulin consists of an A (21 amino acids) and B (30 amino acids) chain which are linked through a pair of disulfide bonds. Across different vertebrate species, minor differences in the primary structure of insulin exist (see diagram 1, reprinted from body [Hadley, M. E. *Endocrinology*, Prentice-Hall, Inc., 1988]. In mammals these difference are usually in the 8, 9 and 10 positions within the intrachain disulfide bond of the A chain and position 30 of the B chain. Although these differences do not appear to affect biological potency, they can be sufficient to make insulin antigenic in some patients [Hadley, M. E., supra]. Insulin variants can be created which vary in time of action. For example, a rapid-acting form of insulin is created by reversing amino acids 28 and 29 on the insulin B-chain (Humalog, insulin lispro injection, Eli Lilly). Alternatively, an intermediate-acting insulin with a slower onset and a longer duration of activity (up to 24 hours) results when insulin is formulated as an amorphous and crystalline suspension with zinc. (humulin L, Lente, Eli Lilly). The wealth of information about the primary amino acid sequence of insulin as well as clinical data about immune reactions in humans to exogenous insulin could help in the design of insulin variants.

In one approach, the three-dimensional structure of the insulin or insulin variant polypeptide, or of this polypeptide-inhibitor complex, is determined by x-ray crystallography, by computer modeling, or most typically, by a combination of these approaches. Both the shape and charges of the insulin or insulin variant polypeptide must be ascertained to elucidate the structure and to determine active site(s) of the molecule. Less often, useful information regarding the structure of the insulin or insulin variant polypeptide may be gained by modeling based on the structure of homologous proteins. In both cases, relevant structural information is used to design analogous insulin or insulin variant polypeptide-like molecules or to identify efficient inhibitors. Useful examples of rational drug design may include molecules which have improved activity or stability as shown by Braxton and Wells, Biochemistry 31: 7796-7801 (1992) or which act as inhibitors, agonists, or antagonists of native peptides as shown by Athauda et al., J. Biochem. 113: 742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the insulin or insulin variant polypeptide may be made available to perform such analytical studies as X-ray crystallography. In addition, knowledge of the insulin or insulin variant polypeptide amino acid sequence provided herein will provide guidance to those employing computer modeling techniques in place of or in addition to x-ray crystallography.

REFERENCES

Athanasiou, K A, Fleischli, J G, Bosma, J., Laughlin, T. J., Zhu C F, Agrawal, C M, Layery, L A. 1999. Effffects of diabetes mellitus on the biomechanical properties of human ankle cartilage. Clin Orthop 368: 182-9.

Chevalier, X. and Tyler, J. A. 1996. Production of binding proteins and role of the insulin-like growth factor I binding protein 3 in human articular cartilage explants. Br. J. Rheum. 35: 515-522.

Cohen, M. P., and Foglia, V. G. 1969. Sulfate35 uptake and incorporation into aortic mucopolysaccharides in experimental diabetes. Proc. Soc. Exp. Biol. Med. 132: 376-78.

Cohen, M. P., and Foglia, V. G. 1970a. Effect of pancreatectomy, hypophysectomy, and pancreatectomy-hypophysectomy on sulfate uptake in rat aortas. Proc. Soc. Exp. Biol. Med. 133: 1275-1278.

Cohen, M. P., and Foglia, V. G. 1970b. Effect of insulin in vitro on 14C-acetate and $^{35}$S-sulfate uptake into aortic mucopolysaccharides in normal and diabetic rats. Proc. Soc. Exp. Biol. Med. 135: 113-115.

Craig, R. G., Yu, Z., Xu, L., Barr, R., Ramamurthy, N., Boland, J., Schneir, M., Golub, L. M. 1998. A chemically modified tetracycline inhibits streptozotocin-induced diabetic depression of skin collagen synthesis and steady-state type I procollagen mRNA. Biochim. Biophys. Acta 1402 (3): 250-260.

Gey, G. O., and Thalhimer, W. 1924. Observations of the effect of insulin introduced into the medium of tissue cultures. J. Amer. Med. Assoc. 82: 1609.

Hadley, M. E. Endocrinology. 1998. Published by Prentice Hall Inc. of Simon & Schuster.

Hajek, A. S., and Solursh. 1975. Stimulation of growth and mucopolysaccharide synthesis by insulin treatment of chick embryo chondrocytes in cell culture. Gen. And Comp. Endocrinology 25: 432-446.

Joosten, L A. B., Helsen, M. M. A., Saxne, T., van de Loo, F. A. J., Heinegard, D., and van den Berg, W. B. 1999. IL1αβ blockade prevents cartilage and bone destruction in murine type II collagen-induced arthritis, whereas TNF-α blockage only ameliorates joint inflammation. J. Immunol. 163: 5049-5055.

Kelley, K. M. et al. 1993. An Insulinlike growth factor-1-resistant state in cartilage of diabetic rats is ameliorated by hypophysectomy. Diabetes 42: 463-469.

Lieberman, I., and Ove, P. 1959. Growth factors for mammalain cells in culture. J. Biol. Chem. 234: 2754-2758.

Paul, J., and Pearson, E. S. 1960. The action of insulin on the metabolism of cell cultures. J. Endocrinol. 21: 287-294.

Portha B, Blondel O, Serradas P, McEvoy R, Giroix M H, Kergoat M, Bailbe D. 1989. The rat models of non-insulin dependent diabetes induced by neonatal streptozotocin. Diabete Metab 15:61-75.

Prasad, G. C., and Rajan, K. T. 1970. Effect of insulin on bone in tissue culture. Acta Orthop. Scand. 41: 44-56.

Radin, E. L., Martin R. B., Burr, D. B., Caterson, B., Boyd, R. D. Goodwin, C. 1984. Effects of mechanical loading on the tissues of the rabbit knee. J. Orthop Res. 2: 221-234.

Radin, E. L., Burr, D. B., Caterson, B., Fyhrie D., Brown, T. D., Boyd, R. D. 1991. Mechanical determinants of osteoarthrosis. Semin Arthritis Rheum (suppl.2) 21:12-21.

Robinson, D., Mirovsky, Y., Halperin, N., Evron Z., and Nevo, Z. 1998. Changes in proteoglycans of intervertebral disc in diabetic patients. A possible cause of increased back pain. Spine 23: 849-55.

Roszkowski-Sliz, W. 1973. Effect of the somatotropic hormone, insulin and durabolin on postadjuvant polyarthritis in rats. Acta Physiol. Pol. XXIV 2371-376.

Salmon, W. D., Jr., and Daughaday, W H. 1957. A hormonally controlled serum factor which stimulates sulfate incorporation by cartilage. J. Lab Clin Med 49: 825-836

Salmon, W. D., Jr. 1960. Importance of amino acids in the action of insulin and serum sulfation factor to stimulate sulfate uptake by cartilage cells from hypophysectomized rats. J. Lab. Clin. Med. 56: 673-681.

Salmon, W. D., Jr., DuVall, M. R., and Thompson, E. Y. 1968. Stimulation by insulin in vitro of incorporation of [$^{35}$S) sulfate and [14C]leucine into protein-polysaccharide complexes, [3H]-uridine into RNA, and [3H]thymidine into DNA of costal cartilage from hypophysectomized rats. Endocrinol. 82, 493-499.

Schafer, S. J, Luyten F. P., Yanagishita, M. and Reddi, A. H. 1993. Proteoglycan metablism is age related and modulated by isoforms of platelet-derived growth factor in bovine articular cartilage explant cultures. Arch. Biochem. Biophys. 302:431-438.

Schwartz, A. G., and Amos, H. 1968. Insulin dependence of cells in primary culture: influence of ribosome integrity. Nature 219: 1366-1367.

Schiller and Dorfman 1957. The metabolism of mucopolysaccharides in animals. IV. The influence of insulin. *J. Biol. Chem.* 227, 625-632.

Schneir, M., Bowersox., J. Ramamurthy, N., Yavelow, J., Murrray, J., Golub, L. 1979. Response of rat connective tissues to streptozotocin diabetes. Tissue specific effects on collagen metabolism. *Biochim. Biophys. Acta* 583: 95-102.

Spanheimer, R. G. Correlation between decreased collagen production in diabetic animals and in cells exposed to diabetic serum: response to Insulin. Matrix 12: 101-107.

Stevens, R. L. and Hascall, V. C. 1981. Characterization of proteoglycans synthesized by rat chondrosarcoma chondrocytes treated with multiplication-stimulating activity and insulin. *J. Biol. Chem.* 256: 2053-2058.

Wei, L., de Bri, E., Lundberg, A., and Svensson, O. 1998. Mechanical load and primary guinea pig osteoarthrosis. *Acta Orthop Scand* 69: 351-357.

Younger L. R., King, J., and Steiner, O. F. 1966. Hepatic proliferative response to insulin in severe alloxan diabetes. *Cancer Res.* 26 (7): 1408-1414.

The invention claimed is:

1. A method of treating damaged cartilage comprising contacting the cartilage by local administration through direct injection with insulin or insulin variant in an amount effective to (a) retain proteoglycans in the matrix, (b) inhibit proteoglycan release from the matrix, or (c) stimulate proteoglycan synthesis.

2. The method of claim 1, wherein the cartilage is articular cartilage.

3. The method of claim 1, wherein the cartilage is contained in a mammal and the amount administered is a therapeutically effective amount.

4. The method of claim 1, wherein the cartilage is damaged as a result of a degenerative disorder.

5. The method of claim 4, wherein the degenerative cartilaginous disorder is rheumatoid arthritis.

6. The method of claim 4, wherein the degenerative cartilaginous disorder is osteoarthritis.

7. The method of claim 1, wherein the cartilage damage results from an injury.

8. The method of claim 7, wherein the type of injury is a microdamage or blunt trauma, a chondral fracture, an osteochondral fracture or damage to meniscus, tendon or ligament.

9. The method of claim 7, wherein the injury is the result of excessive mechanical stress or other biomechanical instability resulting from a sports injury or obesity.

10. The method of claim 1, wherein the insulin or insulin variant is present in the form of a composition further comprising a carrier, excipient or stabilizer.

11. The method of claim 10, wherein the cartilage is present in a mammal, and the amount administered is a therapeutically effective amount.

12. The method of claim 11, wherein the composition is an extended- or sustained-release formulation.

13. The method of claim 12, wherein the composition further comprises poly-lactic-co-glycolic acid.

14. The method of claim 12, wherein the composition further comprises a polyvalent metal salt.

15. The method of claim 14, wherein the polyvalent metal salt is zinc acetate.

16. The method of claim 1, wherein the cartilage is present in a mammal and the amount administered of insulin or insulin variant and cartilage agent is a therapeutically effective amount.

17. The method of claim 16, wherein the treatment further comprises contacting the cartilage with a therapeutically effective amount of a peptide growth factor selected from a family member from the group consisting of: IGF (1,2), PDGF (AA, AB, BB), BMPs, FGF (1-20), TGF-β (1-3) and EGF.

18. The method of claim 16, wherein the treatment further comprises contacting the cartilage with a therapeutically effective amount of a catabolism antagonist selected from the group consisting of IL-1ra, NO inhibitors, ICE inhibitor, agents which inhibit activity of IL-6, IL-8, LIF, IFN-γ, TNFα activity, tetracyclines and variants thereof, inhibitors of apoptosis, MMP inhibitors, aggrecanase inhibitors and inhibitors of serine and cysteine proteinases (such as cathepsins and urokinase or tissue plasminogen activator (uPA or tPA)).

19. The method of claim 16, wherein the treatment further comprises contacting the cartilage with a therapeutically effective amount of a osteo-factor selected from the group consisting of bisphosphonates, osteoprotegerin.

20. The method of claim 16, wherein the comprises contacting the cartilage with a therapeutically effective amount of a anti-inflammatory factor is selected from the group consisting of anti-TNFα, soluble TNF receptors, IL1ra, soluble IL1 receptors, IL4, IL-10 and IL-13.

21. The method of claim 1, wherein the treatment further comprises a standard surgical technique selected from the group consisting of: cartilage shaving, abrasion chondroplasty, laser repair, debridement, chondroplasty, microfracture with or without subchondral bone penetration, mosaicplasty, cartilage cell allografts, stem cell autografts, coastal cartilage grafts, perichondral autografts, periosteal autografts, cartilage scaffolds, shell (osteoarticular) autografts or albografts and osteotomy.

22. The method of claim 1, wherein the treatment further comprises chemical stimulation.

23. The method of claim 1, wherein the treatment further comprises electrical stimulation.

24. A method of reducing damage to cartilage in a patient with a cartilaginous disorder comprising contacting the cartilage by local administration through direct injection or extended release means with insulin or insulin variant in an amount effective to (a) retain proteoglycans in the matrix, (b) inhibit proteoglycan release from the matrix, or (c) stimulate proteoglycan synthesis.

25. The method of claim 24, wherein the cartilage is articular cartilage.

26. The method of claim 24, wherein the patient is a mammal and the amount administered is a therapeutically effective amount.

27. The method of claim 26, wherein the cartilage damage results from an injury.

28. The method of claim 27, wherein the type of injury is a microdamage or blunt trauma, a chondral fracture, an osteochondral fracture or damage to meniscus, tendon or ligament.

29. The method of claim 27, wherein the injury is the result of excessive mechanical stress or other biomechanical instability resulting from a sports injury or obesity.

30. The method of claim 24, wherein the cartilage is damaged as a result of a degenerative cartilaginous disorder.

31. The method of claim 30, wherein the degenerative cartilaginous disorder is rheumatoid arthritis.

32. The method of claim 30, wherein the degenerative cartilaginous disorder is osteoarthritis.

33. The method of claim 24, wherein the insulin or insulin variant is present in the form of a composition further comprising a carrier, excipient or stabilizer.

34. The method of claim 33, wherein the cartilage is present in a mammal, and the amount administered is a therapeutically effective amount.

35. The method of claim 33, wherein the composition is an extended- or sustained- release formulation.

36. The method of claim 35, wherein the composition further comprises poly-lactic-co-glycolic acid.

37. The method of claim 36, wherein the composition further comprises a polyvalent metal salt.

38. The method of claim 37, wherein the polyvalent metal salt is zinc acetate.

39. The method of claim 24, wherein the cartilage is present in a mammal and the amount administered of insulin or insulin variant and cartilage agent is a therapeutically effective amount.

40. The method of claim 39, wherein the method further comprises contacting the cartilage with an effective amount of a catabolism antagonist, selected from the group consisting of IL-1ra, NO inhibitors, ICE inhibitor, agents which inhibit activity of IL-6, IL-8, LIF, IFN-γ, TNFα activity, tetracyclines and variants thereof, inhibitors of apoptosis, MMP inhibitors, aggrecanase inhibitors and inhibitors of serine and cysteine proteinases (e.g. cathepsins, urokinase or tissue plasminogen activator (uPA or tPA)).

41. The method of claim 39, wherein the method further comprises contacting the cartilage with an effective amount of a peptide growth factor selected from a family member from the group consisting of: IGF (1,2), PDGF (AA, AB, BB), BMPs, FGF (1-20), TGF-β (1-3) and EGF.

42. The method of claim 39, wherein the method further comprises contacting the cartilage with an effective amount of a osteo-factor selected from the group consisting of bisphosphonates, osteoprotegerin.

43. The method of claim 39, wherein the method further comprises contacting the cartilage with an effective amount of an anti-inflammatory factor selected from the group consisting of anti-TNFα, soluble TNF receptors, IL1ra, soluble IL1 receptors, IL4, IL-10 and IL-13.

* * * * *